US006423709B1

(12) United States Patent
Panetta et al.

(10) Patent No.: US 6,423,709 B1
(45) Date of Patent: Jul. 23, 2002

(54) METHODS OF USING NOVEL COMPOUNDS AS NEURO-PROTECTIVE AGENTS

(75) Inventors: Jill Ann Panetta, Zionsville; John Kevin Shadle, Fishers; Lawrence Joseph Heinz, Pittsboro; Michael LeRoy Phillips; John Robert Rizzo, both of Indianapolis; Benjamin Alan Anderson, Zionsville; John Allan Rieck, III; David Lee Varie, both of Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/996,005

(22) Filed: Nov. 28, 2001

Related U.S. Application Data

(62) Division of application No. 09/715,987, filed on Nov. 17, 2000, which is a division of application No. 09/368,236, filed on Aug. 4, 1999, now Pat. No. 6,166,216, which is a division of application No. 08/944,468, filed on Oct. 6, 1997, now Pat. No. 6,156,748.

(60) Provisional application No. 60/027,560, filed on Oct. 7, 1996.

(51) Int. Cl.[7] .................... A61K 31/425; A61K 31/42; A61K 31/415; A61P 25/00

(52) U.S. Cl. .............................. 514/227.8; 514/236.8; 514/255; 514/307; 514/309; 514/312; 514/314; 514/340; 514/343; 514/365; 514/374

(58) Field of Search .......................... 514/227.8, 236.8, 514/255, 307, 309, 312, 314, 340, 343, 365, 375

(56) References Cited

U.S. PATENT DOCUMENTS

| | | | |
|---|---|---|---|
| 4,636,516 | A | 1/1987 | Kubo et al. |
| 4,966,855 | A | 10/1990 | Deneke et al. |
| 5,061,705 | A | 10/1991 | Wuest et al. |
| 5,428,048 | A | 6/1995 | Malamas et al. |
| 5,604,225 | A | 2/1997 | Reiffan et al. |
| 5,614,520 | A | 3/1997 | Kondo et al. |
| 5,633,271 | A | 5/1997 | Amoo et al. |
| 5,747,517 | A | 5/1998 | Panetta et al. |

FOREIGN PATENT DOCUMENTS

| | | |
|---|---|---|
| EP | 0 382 199 | 8/1990 |
| WO | WO 87/03807 | 7/1987 |
| WO | WO 94/18180 | 8/1994 |
| WO | WO 99/09829 | 3/1999 |
| WO | WO 99/09979 | 3/1999 |
| WO | WO 99/09980 | 3/1999 |
| WO | WO 99/18091 | 4/1999 |

OTHER PUBLICATIONS

Hulin et al., *Chem Abstract* 116:255519 (1992).

*Primary Examiner*—Floyd D. Higel
*Assistant Examiner*—Andrea D. Small
(74) *Attorney, Agent, or Firm*—Janet A. Gongola

(57) ABSTRACT

This invention relates to novel phenyl oxazoles, thiazoles, oxazolines, oxadiazoles and benzoxazoles useful as neuro-protective agents.

4 Claims, No Drawings

METHODS OF USING NOVEL COMPOUNDS AS NEURO-PROTECTIVE AGENTS

This is a division of application Ser. No. 09/715,987 filed on Nov. 17, 2000 which is a division of application Ser. No. 09/368,236 filed on Aug. 4, 1999, now U.S. Pat. No. 6,166,216, which is a division of application Ser. No. 08/944,468 filed Oct. 6, 1997, now U.S. Pat. No. 6,156,748 granted Dec. 5, 2000, which claims priority to U.S. Provisional Application No. 60/027,560 filed Oct. 7, 1996.

FIELD OF THE INVENTION

This invention relates to novel phenyl oxazoles, thiazoles, oxazolines, oxadiazoles and benzoxazoles useful as neuro-protective agents.

BACKGROUND OF THE INVENTION

Neurodegenerative processes can involve diverse areas of the Central Nervous System (CNS). Neurodegeneration appears clinically as a breakdown of functionally connected neuronal circuits with corresponding alterations in the neurotransmitter system and morphological organization of the affected cell system.

The normal functioning of the CNS presupposes a well-balanced interaction between different biochemical and structurally linked neuronal systems. When one member of a neuronal circuit is altered in its structural or biochemical entity, an imbalance in the functional system results and a compensatory mechanism must be activated in order to maintain physiological equilibrium.

Perhaps the most severe form of neurodegeneration is that seen after stroke. This form of cerebral ischemia results in the death of neurons, as well as glial cells and vascular elements of the brain. Quite often a stroke results in paralysis, memory loss, inability to communicate, and even death. Reactive oxygen intermediates are believed to play a role in causing brain death in stroke victims. Another form of cerebral ischemia that can be quite devastating to important groups of selectively vulnerable neurons, is global ischemia. Global cerebral ischemia is commonly seen in victims of cardiac arrest during the period of time the heart is undergoing fibrillation. Neuronal death from global ischemia is a common occurrence in heart attack victims that undergo cardiac arrest and cardiac arrest is a common occurrence in heart attack patients. Reactive oxygen species are also believed to be one of the causative factors in neuronal death during the reperfusion phase after global ischemia. Ischemia-reperfusion injury caused by global or local ischemia or during transplantation can also affect other major organs of the body such as the kidney, liver and heart. Reactive oxygen intermediates that are generated during the reperfusion phase in these organs are thought to cause significant injury.

Other degenerative diseases of the central nervous system are believed to be exacerbated or initiated by processes that result in the generation of reactive oxygen intermediates. Parkinson's disease (PD) is characterized by reduced size and velocity of movements. In Alzheimer's disease (AD), cognitive impairment is the cardinal clinical symptom. In motoreuron disease, (for example, amyotrophic lateral sclerosis, ALS), a degeneration of the central pyramidal, the peripheral motor system or both is the reason for the clinical picture.

Idiopathic PD is a movement disorder in which symptomatology is defined by three cardinal symptoms: tremor at rest, rigidity and akinesia (Fahn, 1989). The course of the disease is a progressive one. For a long time, anticholinergic drugs were the only effective treatment of parkinsonian symptoms. The beneficial effect of L-3,4-dihydrophenylalanine (L-DOPA) therapy has increased, patient's life expectancy to a significant degree. However, the advanced stage of the disease is dominated by the complications of L-DOPA therapy and lack of L-DOPA responsiveness. A limiting factor in PD therapy is the psychotic potential of many anti-parkinsonian drugs.

ALS is a chronic progressive degenerative disorder, which, in its classical form, appears sporadically. The most prominent pathological change in ALS patients is a loss of large motoreurons in the motor cortex, brain stem and spinal cord.

Cognitive decline is the essential clinical criteria for AD manifested by memory loss, disorientation and the concomitant loss of enjoyment of life associated therewith. Only after death can the diagnosis be confirmed pathologically by the presence of numerous amyloid and neuritic plaques in the brain.

At present, the pharmacological therapy of neurodegenerative disorders is limited to symptomatic treatments that do not alter the course of the underlying disease.

Meanwhile, because of the current dissatisfaction with the currently marketed treatments for the above-described indications within the affected population, the need continues for safer, better-calibrated drugs which will either slow the process of neurodegeneration associated with focal or global ischemia, ALS, Alzheimer's and Parkinson's disease or even prevent such neurodegeneration altogether.

The present invention provides new phenyl oxazole and phenyl thiazole compounds useful for treating neurodegeneration and reperfusion injury of peripheral organs. The compounds of the invention inhibit the formation of reactive oxygen species in a mammal and are thereby useful for treating conditions and diseases which are believed to be induced by increased free radical production such as global and cerebral ischemia, Parkinson's disease, Alzheimer's disease, Down's syndrome, ALS and ischemia/reperfusion injury of peripheral organs. Malamas, et al., U.S. Pat. No. 5,428,0478 disclose phenyl oxazoles useful for treating diseases of inflammation, allergic responses and arteriosclerosis while Panetta, et al., EP Application No. 677,517 teach benzylidene rhodanines to treat Alzheimer's disease.

SUMMARY OF THE INVENTION

This invention provides compounds of the formula III (III)

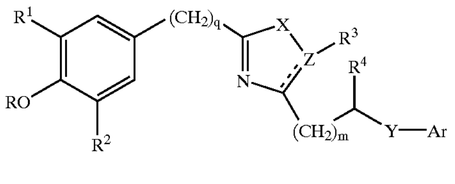

wherein:

Ar is phenyl, pyridyl, tetrahydronaphthyl, benzofuranyl or chromanyl substituted with zero to two substituents selected from the group consisting of —$(C_1–C_6)$alkyl, hydroxy and halo; and substituted with either:

(i) one or two substituents selected from the group consisting of —$O(CH_2)_tR^6$,

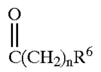

and $—(C_1–C_6\ alkyl)R^6$; or (ii) two substituents which when taken together with the carbon atoms to which they are attached form a pyridyl or tetrahydropyridyl ring;

provided that when substituent pattern (i) is present, the phenyl or pyridyl group of Ar may additionally be substituted with two substituents which when taken together with the carbon atoms to which they are attached form a phenyl ring;

where $R^6$ is $—NR^7R^8$, morpholin-1-yl, imidazol-1-yl, 4,5-dihydro-1H-imidazol-2-yl, thiomorpholin-1-yl, piperazin-1-yl or piperazin-1-yl substituted with $—(C_1–C_4)$alkyl or

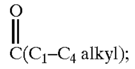

and $R^7$ and $R^8$ are each individually hydrogen, $—(C_1–C_6)$alkyl, $—(CH_2)_pOH$,

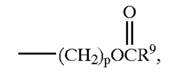

$—(CH_2)_p$-piperidyl, $—(CH_2)_pS(C_1–C_6)$alkyl, $—(CH_2)_pO(C_1–C_6)$alkyl

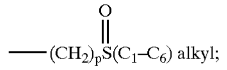

where $R^9$ is $(C_1–C_6)$alkyl;

represents a double or single bond;

X is —O— or —S—;

Y is $—CR^{5'}R^5—$, —O— or —S—, where $R^{5'}$ is H and $R^5$ is —H or —OH or $R^5$ and $R^{5'}$ taken together are =O;

Z is $—CH_2—$ or —N—;

R is H or $—(C_1–C_6)$alkyl;

$R^1$ and $R^2$ are each individually $—(C_1–C_6)$alkyl, $—(C_1–C_6)$alkoxy or phenyl;

$R^3$ is H or $—(C_1–C_6)$alkyl or $R^3$ and $R^4$ taken together form a phenyl group with the ring to which they are attached;

$R^4$ is hydrogen or —OH, or when Y is $—CHR^5$, $R^4$ and $R^5$ are each individually H or when taken together form a bond;

m is an integer from 0 to 2, both inclusive;

g is 0 or 1;

n is an integer from 0 to 4 both inclusive;

p is an integer from 1 to 6 both inclusive; and t is an integer from 1 to 4 both inclusive;

or a pharmaceutically acceptable salt, hydrate or optical isomer thereof.

According to a further aspect of the present invention there are provided pharmaceutical compositions comprising as active ingredient a compound of formula III or a pharmaceutically acceptable salt, hydrate or optical isomer thereof, in association with one or more pharmaceutically acceptable diluents, carriers and excipients thereof.

The present invention in addition provides a method for inhibiting the formation of reactive oxygen species in a mammal which comprises administering to said mammal a therapeutically effective amount of a compound of the formula III.

The present invention also provides a method for inhibiting lipid peroxidation in a mammal in need of such treatment which comprises administering to said mammal a therapeutically effective amount of a compound of the formula III.

Moreover, it has been discovered that compounds of formula I are also useful for preventing ischemia-induced cell damage such as may be caused by strokes, myocardial infarction, cardiac arrest or during transplantation. Ischemia represents a phenomenon in which tissue is deprived of either partial or total blood flow in conjunction with hypoxia. Reperfusion of such tissue causes additional tissue injury associated with ischemic events to vital organs such as the lung, liver, kidney, heart and small bowel. This invention, therefore, also provides a method for preventing ischemia-induced cell damage in mammals by administering to a mammal in need thereof an therapeutically effective amount of a compound of formula III.

Further, the present invention provides a method for treating Parkinson's disease in a mammal in need of such treatment which comprises administering to said mammal a therapeutically effective amount of a compound of formula I.

In another aspect of the present invention is provided a method for treating Alzheimer's disease in a mammal in need of such treatment which comprises administering to said mammal a therapeutically effective amount of a compound of formula III.

Still another aspect of the present invention provides a method of treating amyotrophic lateral sclerosis (ALS) in a mammal in need of such treatment which comprises administering a therapeutically effective amount of a compound of formula III.

Other objects, features and advantages of the present invention will become apparent from the subsequent description and the appended claims.

DETAILED DESCRIPTION OF THE INVENTION

As used herein, the term "$C_1$–$C_6$ alkyl" represents a straight or branched alkyl chain having from one to six carbon atoms. Typical $C_1$–$C_6$ alkyl groups include methyl, ethyl, n-propyl, isopropyl, n-butyl, sec-butyl, isobutyl, t-butyl, n-pentyl, isopentyl, neopentyl, hexyl and the like.

The term "halo" means chloro, fluoro, bromo or iodo.

The term "$(C_1–C_6)$alkoxy" means a group such as methoxy, ethoxy, n-propoxy, isopropxy, n-butoxy, t-butoxy, n-pentoxy, isopentoxy, neopentoxy, hexoxy and like groups attached to the remainder of the molecule by the oxygen. atom.

The term "pharmaceutically acceptable salts" refers to salts of the compounds of the above formulae which are substantially non-toxic to living organisms. Typical pharmaceutically acceptable salts include those salts prepared by reaction of the compounds of the above formulae with a pharmaceutically acceptable mineral or organic acid, or a pharmaceutically acceptable alkali metal or organic base, depending on the types of substituents present on the compounds of the formulae.

Examples of pharmaceutically acceptable mineral acids which may be used to prepare pharmaceutically acceptable salts include hydrochloric acid, phosphoric acid, sulfuric acid, hydrobromic acid, hydroiodic acid, phosphorous acid and the like. Examples of pharmaceutically acceptable organic acids which may be used to prepare pharmaceutically acceptable salts include aliphatic mono and dicarboxylic acids, such as oxalic acid, carbonic acid, citric acid, succinic acid, phenyl-substituted alkanoic acids, aliphatic and aromatic sulfuric acids and the like. Such pharmaceutically acceptable salts prepared from mineral or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

It should be recognized that the particular anion or cation forming a part of any salt of this invention is not critical, so long as the salt, as a whole, is pharmacologically acceptable and as long as the anion or cationic moiety does not contribute undesired qualities.

The term “amino-protecting group” is used herein as it is frequently used in synthetic organic chemistry, to refer to a group which will prevent an amino group from participating in a reaction carried out on some other functional group of the molecule, but which can be removed from the amine when it is desired to do so. In a similar fashion, the term “hydroxy protecting group” refers to a removable group which will prevent a hydroxy group from participating in a reaction performed on the molecule. Such groups are discussed by T. W. Greene in chapters 2 and 7 of *Protective Groups in Organic Synthesis*, John Wiley and Sons, New York, 1981, and by J. W. Barton in chapter 2 of *Protective Groups in Organic Chemistry*, J. F. W. McOmie, ed., Plenum Press, New York, 1973, which are incorporated herein by reference in their entirety. Examples of amino protecting groups include benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-utyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and D-methoxybenzoyl; and;other groups such as methanesulfonyl, 2-toluenesulfonyl, p-bromobenzenesulfonyl, D-nitrophenylethyl, and p-toluenesulfonylaminocarbonyl. A preferred amino-blocking group is t-butoxycarbonyl.

Examples of hydroxy protecting groups include ether and substituted ether forming groups such as methyl, methoxymethyl, t-butoxymethyl, 1-ethoxyethyl and benzyl; silyl ether forming groups such as trimethylsilyl, triethylsilyl and methyl-diisopropylsilyl; ester forming groups such as formate, acetate and trichloroacetate and carbonate groups, such as methyl, 2,2,2-trichloroethylcarbonate and p-nitrophenyl carbonates.

The compounds of the instant invention may exist in various isomeric forms, for example, when Ar is a phenyl or pyridyl substituted with one or two —($C_1$–$C_6$ alkyl)$R^6$ groups or when $R^4$ and $R^5$ taken together form a bond or when Y is —C(OH)H—. This invention is not related to any particular isomer but includes all possible individual isomers and racemates.

The skilled artisan will understand that when Z is nitrogen and - - - - is a double bond between Z and the carbon to which it is attached, N has no $R^3$ substituent.

Many of the compounds of formula I can combine with water to form hydrates. This invention encompasses the hydrates of formula I.

Preferred Compounds of the Invention

Preferred groups include the following:

(a) Ar is phenyl substituted with one or two substituents selected from

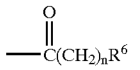

and —($C_1$–$C_6$ alkyl)$R^6$ or with two substituents which when taken together with the carbon atoms to which they are attached form a pyridyl or tetrahydropyridyl ring;

(b) Ar is phenyl substituted with —($C_1$–$C_6$)alkyl, hydroxy, halo or with two substituents which when taken together with the carbon atoms to which they are attached form a phenyl ring;

(c) Ar is pyridyl substituted with —($C_1$–$C_6$)alkyl, hydroxy, halo or with two substituents which when taken together with the carbon atoms to which they are attached form a phenyl ring;

(d) Ar is phenyl substituted with —($C_1$–$C_6$ alkyl)$R^6$;

(e) Ar is phenyl substituted with

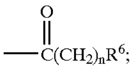

(f) $R^6$ is —$NR^7R^8$;

(g) $R^6$ is morpholin-1-yl or thiomorpholin-1-yl;

(h) $R^6$ is imidazol-1-yl or 4,5-dihydro-1-1H-imidazol-2-yl;

(i) $R^6$ is piperazin-1-yl or piperazin-1-yl substituted with —($C_1$–$C_4$)alkyl or

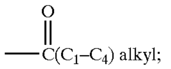

(j) $R^7$ and $R^8$ are each individually hydrogen or —($C_1$–$C_6$)alkyl;

(k) $R^1$ and $R^2$ are each individually —($C_1$–$C_6$)alkyl;

(l) $R^3$ is —($C_1$–$C_6$)alkyl;

(m) Y is —O— or —S—;

(n) Y is —$CHR^5$—;

(o) m is 1;

(p) p is an integer from 1–3 both inclusive.

A preferred group of compounds include compounds of the formula (II)

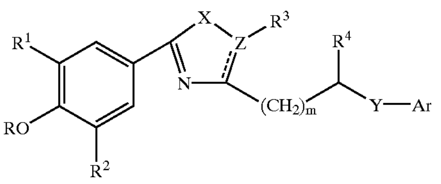

(II)

wherein:

Ar is phenyl, pyridyl, or tetrahydronaphthyl substituted with zero to two substituents selected from the group consisting of —$(C_1$–$C_6)$alkyl, hydroxy and halo; and substituted with either:

(i) one or two substituents selected from the group consisting of —$O(CH_2)_tR^6$,

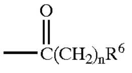

and —$(C_1$–$C_6$ alkyl$)R^6$; or (ii) two substituents which when taken together with the carbon atoms to which they are attached form a pyridyl or tetrahydropyridyl ring;

provided that when substituent pattern (i) is present, the phenyl or pyridyl croup of Ar may additionally be substituted with two substituents which when taken together with the carbon atoms to which they are attached form a phenyl ring;

where $R^6$ is —NR7$R^8$, morpholin-1-yl, imidazol-1-yl, 4,5-dihydro-1H-imidazol-2-yl, thiomorpholin-1-yl, piperazin-1-yl or piperazin-1-yl substituted with —$(C_1$–$C_4)$alkyl or

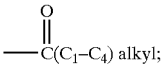

and $R^7$ and $R^8$ are each individually hydrogen, —$(C_1$–$C_6)$alkyl, —$(CH_2)_pOH$, —$(CH_2)_p$-piperidyl, —$(CH_2)_pS(C_1$–$C_6)$alkyl or

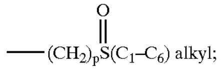

represents a double or single bond;

X is —O— or —S—;

Y is —$CHR^5$—, —O— or —S—;

Z is —CH— or —N—;

R is H or —$(C_1$–$C_6)$alkyl;

$R^1$ and $R^2$ are each individually —$(C_1$–$C_6)$alkyl or —$(C_1$–$C_6)$alkoxy;

$R^3$ is H or —$(C_1$–$C_6)$alkyl, or $R^3$ and $R^4$ taken together form a phenyl group with the ring to which they are attached;

$R^4$ is hydrogen, or when Y is —$CHR^5$, $R^4$ and $R^5$ are each individually H or when taken together form a bond;

m is an integer from 0 to 2, both inclusive;

q is 0 or 1;

n is an integer from 0 to 4 both inclusive;

p is an integer from 1 to 6 both inclusive; and t is an integer from 1 to 4 both inclusive;

or a pharmaceutically acceptable salt, hydrate or optical isomer thereof.

Another preferred group of compounds include compounds of the formula (I)

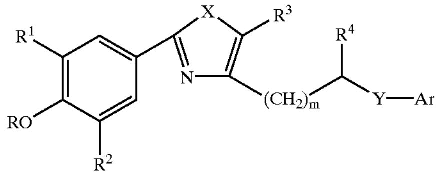

(I)

wherein:

Ar is phenyl or pyridyl substituted with zero to two substituents selected from the group consisting of —$C_1$–$C_6$ alkyl, hydroxy and halo; and substituted with either:

(i) one or two substituents selected from the group consisting of

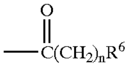

and —$(C_1$–$C_6$ alkyl$)R^6$; or (ii) two substituents which when taken together with the carbon atoms to which they are attached form a pyridyl or tetrahydropyridyl ring;

provided that when substituent pattern (i) is present, the phenyl or pyridyl group of Ar may additionally be substituted with two substituents which when taken together with the carbon atoms to which they are attached form a phenyl ring;

where $R^6$ is —$NR^7R^8$, morpholin-1-yl, imidazol-1-yl, 4,5-dihydro-1H-imidazol-2-yl, thiomorpholin-1-yl, piperazin-1-yl or piperazin-1-yl substituted with —$(C_1$–$C_4)$alkyl or

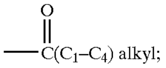

and $R^7$ and $R^8$ are each individually hydrogen, —$(C_1$–$C_6)$alkyl, —$(CH_2)_pOH$ or —$(CH_2)_p$-piperidyl;

X is —O— or —S—;

Y is —$CHR^5$—, —O— or —S—;

R is —H or $(C_1$–$C_6)$alkyl;

$R^1$ and $R^2$ are each individually —$(C_1$–$C_6)$alkyl;

$R^3$ is H or —$(C_1$–$C_6)$alkyl;

$R^4$ is hydrogen, or when Y is —$CHR^5$, $R^4$ and $R^5$ are each individually H or when taken together form a bond;

m is 0 or 1;

n is an integer from 0 to 4 both inclusive; and p is an integer from 1 to 6 both inclusive;

or a pharmaceutically acceptable salt, hydrate or optical isomer thereof.

It will be understood that the above classes may be combined to form additional preferred classes.

A preferred genus of compounds include those compounds where:

Ar is phenyl substituted with one or two substituents selected from

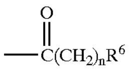

and —$(C_1$–$C_6$ alkyl)$R^6$ where $R^6$ is —$NR^7R^8$ and $R^7$ and $R^8$ are H or —$(C_1$–$C_6)$alkyl;

and one or two substituents selected from hydrogen, —$(C_1$–$C_6)$alkyl and hydroxy; or two substituents which when taken together with the carbon atoms to which they are attached form a phenyl group.

$R^1$ and $R^2$ are —$(C_1$–$C_6)$alkyl;

R, $R^3$ and $R^4$ are hydrogen;

X is —O—;

Y is —O— or —S—;

Of this preferred genus, compounds in which $R^1$ and $R^2$ are 1,1-dimethylethyl are more preferred.

Of this more preferred genus, those compounds in which Ar is phenyl substituted with one or two —$(C_1$–$C_6$ alkyl)$R^6$ groups and one or two substituents selected from hydrogen and —$(C_1$–$C_6)$alkyl are especially preferred.

Of this especially preferred genus, those compounds in which Ar is phenyl substituted with —$(C_1$–$C_6$ alkyl)$R^6$ are particularly preferred.

Further typical examples of compounds of formula I which are useful in the present invention include:

2-(3-methyl-4-hydroxy-5-ethyl)phenyl-4-(2-(4-methyl-3-aminoprop-1-ylphenoxy)ethyl)oxazole 2-(3-isopropyl-4-ethoxy-5-n-propyl)phenyl-4-(2-(4-N-propyl-6-aminohex-1-ylphenoxy)ethyl)thiazole oxalate 2-(3-hexyl-4-pentoxy-5-t-butyl)phenyl-4-(2-(4-N-ethylaminomethylphenoxy)ethyl)oxazole 2-(3-n-propyl-4-hydroxy-5-neopentyl)phenyl-4-(2-(4-N-ethylaminomethylphencxy)ethyl)-5-methyloxazole maleate 2-(3-isopropyl-4-propoxy-5-ethyl)phenyl-4-(2-(4-N-ethylaminomethylphenoxy)ethyl)-5-ethylthiazole 2-(3-methyl-4-n-pentoxy-5-sec-butyl)phenyl-4-(2-(4-N-ethylaminomethylphenoxy)ethyl)-5-isopropyloxazole tosylate 2-(3,5-di-t-butyl-4-hydroxyphenyl)-4-(2-(4-N-ethylaminomethylphenoxy)ethyl)thiazole 2-(3-methyl-4-methoxy-5-n-butyl)phenyl-4-(2-(2-fluoro-4-N-ethylaminomethylphenoxy)ethyl)oxazole hydrobromide 2-(3-t-butyl-4-hydroxy-5-ethyl)phenyl-4-(2-(2-propyl-4-N-ethylaminomethylphenoxy)ethyl)oxazole 2-(3-isobutyl-4-hydroxy-5-n-pentyl)phenyl-4-(2-(4-N-ethylaminomethyl-5-hydroxyphenoxy)ethyl)thiazole 2-(3,5-dimethyl-4-ethoxyphenyl)-4-(2-(2-hexyl-4-N-ethylaminomethylphenoxy)ethyl)oxazole mesylate 2-(3-n-butyl-4-pentoxy-5-isopropylphenyl)-4-(2-(5-N-ethyl-N-methylaminomethylpyrid-2-yloxy)ethyl) thiazole 2-(3-neopentyl-4-hydroxy-5-ethylphenyl)-4-(2-(5-N-ethyl-N-methylaminomethylpyrid-2-yloxy)ethyl)-5-methyloxazole nitrate 2-(3,5-di-sec-butyl-4-hydroxyphenyl)-4-(2-(5-N-ethyl-N-methylaminomethylpyrid-2-yloxy)ethyl)-5-isobutyloxazole 2-(3,5-di-n-proply-4-methoxyphenyl)-4-(2-(5-N-ethyl-N-methylaminomethylpyrid-2-yloxy)ethyl)oxazole pyrosulfate 2-(3-sec-butyl-4-methoxy-5-ethyl)phenyl-4-(2-(2-bromo-5-N-ethyl-N-methylaminomethylpyrid-2-yloxy)ethyl)-5-isopropyloxazole 2-(3,5-di-isopropyl-4-hydroxyphenyl)-4-(2-(3-hydroxy-5-thiomorpholinomethylpyrid-2-yloxy)ethyl)thiazole metaphosphate 2-(3-methyl-4-propoxy-5-ethyl)phenyl-4-(2-(5-N-methyl-N-ethyl-4-aminobut-1-ylpyrid-2-yloxy)ethyl) oxazole 2-(3,5-di-t-butyl-4-hydroxyphenyl)-4-(2-(5-(N-methyl-N-(3-(piperidin-3-yl)propyl)aminomethyl) pyrid-2-yloxy)ethyl)oxazole methanesulfonate 2-(3,5-di-t-butyl-4-methoxyphenyl)-4-(2-(5-N-ethyl-N-methyl-3-aminopropyl-1-yl-pyrid-2-yloxy)ethyl) oxazole sulfate 2-(3,5-di-t-butyl-4-ethoxyphenyl)-4-(2-(5-N-ethyl-N-n-propylaminomethylpyrid-2-yloxy)ethyl)thiazole 2-(3-hexyl-4-ethoxy-5-ethylphenyl-4-(2-(4-N-methyl-N-n-butylaminomethylphenylthio)ethyl)oxazole phosphate 2-(3-n-propyl-4-methoxy-5-hexylphenyl)-4-(2-(4-N-methyl-N-ethylaminomethylphenylthio)ethyl) thiazole 2-(3,5-di-t-butyl-4-hydroxyphenyl)-4-(2-(3-chloro-4-N,N-dimethylaminomethylphenylthio)ethyl)-5-isopropyloxazole citrate 2-(3-t-butyl-4-hydroxy-5-neopentyl)phenyl-4-(2-(3,5-dimethyl-4-N,N-diethyl-3-aminopropyl-1-ylphenylthio)ethyl)oxazole 2-(3,5-dimethyl-4-hydroxyphenyl)-4-(2-(4-(N-methyl-N-3-(piperin-3-yl)prop-1-yl-2-aminoethyl-1-ylphenylthio)ethyl)oxazole bisulfate 2-(3-methyl-4-hydroxy-5-ethyl)phenyl-4-(2-(4-N-n-propyl-N-ethylaminomethylphenylthio)ethyl)thiazole 2-(3,5-di-t-butyl-4-hydroxyphenyl)-4-(3-(4-N-methyl-N-ethylaminomethylphenyl)ethyl)-5-methylthiazole lactate Z-2-(3,5-di-t-butyl-4-propoxyphenyl)-4-(3-(4-N-N-di-n-butylaminomethylphenyl)-2-propenyl)oxazole E-2-(3-methyl-5-n-butyl-4-ethoxyphenyl)-4-(4-(4-methylethylaminomethylpyridyl)ethyl)oxazole 2-(3,5-di-t-butyl-4-hydrophenyl)-4-(3-(4-N-methyl-N-ethylaminomethylphenyl)oxazole Z-2-(3,5-di-t-butyl-4-hydroxyphenyl)-4-(3-(4-N-methyl-N-ethylaminomethylphenyl)-2-propenyl)oxazole E-2-(3,5-di-t-butyl-4-hydroxyphenyl)-4-(3-(4-N-methyl-N-ethylaminomethylphenyl)-2-propenyl)oxazole

Synthesis Methods

The compounds of formula I where Ar is phenyl substituted with one or two —$(C_1$–$C_6$ alkyl)$R^6$ groups where the alkyl group is —$CH_2$—, X and Y are oxygen, $R^4$ is hydrogen and m is 1 are prepared according to the following .general reaction scheme I(a)(1).

Scheme I(a) (1)

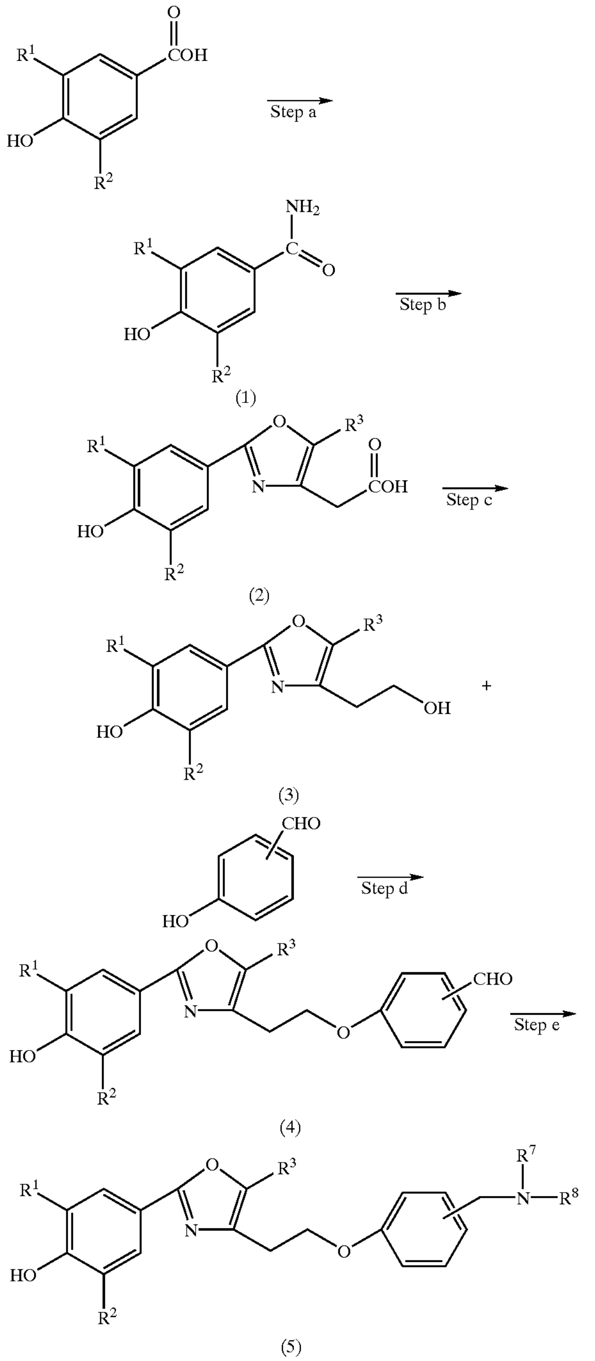

(1) (2) (3) (4) (5)

In step (a) of the above reaction scheme, an appropriately substituted benzoic acid is converted to the benzamide (1) by refluxing with an activating agent such as 2-chloro-4,6-dimethoxy-1,3,5-trizine (CDMT) 1,1-carbonyldiimidazole (CDI), or dicyclohexylcarbodiimide (DCC), preferably CDMT, then cooling to ambient temperature and treating with concentrated aqueous ammonia or an ammonia equivalent such as hexamethyldisilazine. The reaction can be conducted in an aprotic polar solvent, preferably tetrahydrofuran, for a period of from 1 to 24 hours.

The oxazoleacetic acid compound (2) is prepared in step (b) by cyclizing the benzamide (1) with a reagent such as ethyl-4-chloroacetoacetate preferably neat under an inert gas such as nitrogen at a temperature of about 50° C. to 130° C., preferably at 130° C., for about one to two hours and then hydrolysing to form the acid which may be isolated by recrystalization, if desired. Optionally, solvents such as xylene or toluene may be employed and the reaction run at reflux temperatures.

Preparation of the phenyloxazole (3) is achieved in step (c) by reducing the acid (2) with a reducing agent, preferably an excess of borane tetrahydrofuran, followed by treatment with an alcoholic or protic solvent, preferably methanol. Other suitable reducing agents include borane 4,6-dimethyoxybenzene-1,3-disulfonyl chloride, lithium aluminum hydride, sodium borchydride or lithium borchydride. The reaction can be conducted in an aprotic polar solvent such as tetrahydrofuran, or dioxane, preferably tetrahydrofuran, at temperatures from about −10° C. to ambient temperature, preferably ambient temperature for about 1 to 24 hours.

In step (d), the phenyloxazole (3) can be coupled with a hydroxy substituted benzaldehyde to form aldehyde (4) by first mesylating (3) with a mesylating agent such as methanesulfonyl chloride and then coupling the mesylated compound with the benzaldehyde. The coupling reaction can be conducted in an aprotic polar solvent such as dimethylsulfoxide in the presence of potassium t-butoxide while heating to a temperature of about 70° C. for up to 24 hours.

When $R^1$ and $R^2$ are small lower alkyl substituents such as methyl or ethyl, the hydroxy of the phenyl ring is preferably protected with a hydroxy protecting group to prevent mesylation of the phenol. The protecting group may then be removed after the coupling step.

When $R^1$ and $R^2$ are bulky alkyl substituents such as t-butyl, mesylation preferentially occurs on the alcohol attached to the oxazole or thiazole ring, thus the hydroxy does not need to be protected.

Alternately, preparation of (4) can be accomplished by a Mitsunobu coupling which can be conducted in an aprotic polar solvent, such as tetrahydrofuran, at ambient temperature.

Reductive amination of the aldehyde to form desired product (5) is accomplished in step (e) by reacting compound (4) with an appropriately substituted amine and titanium IV isopropoxide ($Ti(OiPr)_4$) using a reducing agent such as sodium borohydride. The reaction is preferably conducted at ambient temperature in a low molecular weight alcohol such as ethanol. The reaction is substantially complete in 16 hours to 3 days.

Alternately, the reduction step (e) can be accomplished by dissolving the aldehyde (4) in a low molecular weight alcohol, such as methanol, acidifying the solution with an excess of an organic acid, such as acetic acid, then reacting the aldehyde (4) with an appropriately substituted amine using a reducing agent, such as sodium cyanoborohydride (sodium cyancborchydride). The reaction is conducted at ambient temperatures under an inert gas, such as nitrogen, and the reaction is substantially complete in about six hours. Abdel-Maged, et al., *J.Org.Chem.*, 1996, 61, 3849.

Similarly, the reductive amination reaction can be accomplished in dichloroethane using sodium (triacetoxy) borohydride.

Compounds of Formula I where R is —$(C_1$–$C_6)$alkyl can be prepared by alkylating the phenol of compound (4) of Scheme I(a), after the coupling step (d), using an appropriate —$(C_1$–$C_6)$alkyl halide, such as methyl iodide, and sodium hydride in an aprotic polar solvent or solvent mixture such as tetrahydrofuran and dimethylformamide. The reaction may be conducted at ambient temperature and is substantially complete within 31 hours. Reductive amination can then be accomplished as described in Scheme I(a), step (e).

In an alternate procedure as depicted in Scheme I(a)(2), below, the phenyl oxazole (3) is treated with a mesylating agent, preferably methanesulfonyl chloride in the presence of a base, preferably triethylamine. Other suitable bases include pyridine or 2,6-lutidene or diisopropyl ethylamine. The reaction is preferably conducted under an inert atmosphere, such as nitrogen, using an aprotic solvent, preferably methylene chloride. Tetrahydrofuran or acetonitrile are other appropriate solvents. At temperatures of from −10° C. to ambient temperatures, preferably at about 0° C., the reaction is substantially complete in 1 to 24 hours.

In a preferred procedure, the phenol oxazole (3) is treated with a tosylating agent such as tosyl chloride or, preferably, tosic anhydride, in the presence of a base, preferably pyridine and a catalyst such as dinmethylam,inopyridine. Other tertiary amines such as triethylamine, or 2,6-lutidine may also be employed. The reaction is preferably conducted under an inert gas, such as nitrogen at temperatures of from about −10° C. to 35° C., preferably at ambient temperatures. Aprotic solvents, such as tetrahydrofuran or methylene chloride, are preferred.

Desired product (5) may then be readily accomplished by refluxing the mesylate or tosylate (110) with amine (111) in the presence of a strong base, preferably sodium hydride or sodium t-butoxide. Potassium bases are also acceptable but less preferred than sodium. Suitable solvents include but are not limited to aprotic solvents such as tetrahydrofuran, dimethylsulfoxide, dimethylformamide or dioxane.

In a preferred one-pot alkylation, the tosylate (110) and amine (111) are refluxed under an inert gas such as nitrogen in the presence of anhydrous solid sodium hydroxide as a base using tetrahydrofuran as a solvent.

Scheme I(a) (2)

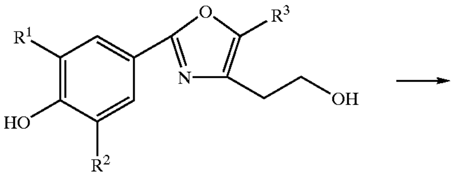

(3)

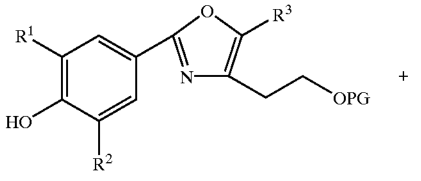

(110)

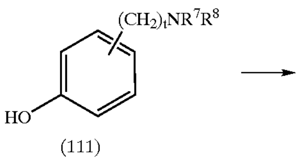

(111)

-continued

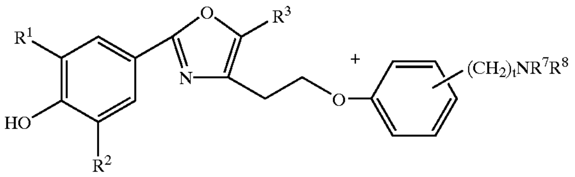

(5)

PG is tosylate or mesylate
t is 1 to 6

Where t is 1, amine (111) is prepared according to the procedures of Abdel-Maged, et al., supra.

Alternately, where t is 1–6, preparation of (11) is accomplished as shown in Scheme I(a)(3), below.

A solution of carboxylic acid (115) in an aprotic solvent such as tetrahydrofuran is treated with an activating group, preferably isobutylchloroformate in the presence of a base such as 4-methyl-morpholine. Other suitable activating agents include arylalkyl chloroformates, such as phenyl. The reaction is conducted at temperatures of from about −78° C. to ambient temperature, preferably at about −50° C.

An amine of the formula $HNR^7R^8$ is added and the reaction is allowed to proceed, preferably at temperatures of about −50° C. Reduction of the amide (116) to amine (111) is then readily achieved using a reducing agent, such as borane dimethylsulfide.

Scheme I(a) (3)

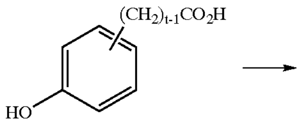

(115)

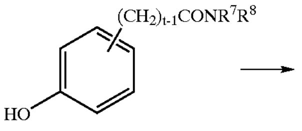

(116)

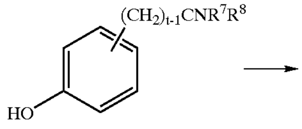

(111)

t is 1 to 6

Compounds of Formula I where $R^7$ or $R^8$ are —$(CH_2)$ piperidyl, —$(CH_2)_p S(C_1–C_6)$alkyl or

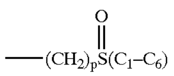

alkyl can be prepared as shown in Scheme I(b) below by reacting the aldehyde (4) with an amine or an aminehydrochloride salt of the formula $H_2NR^{10}$ where $R^{10}$ is H or —$(C_1–C_6)$alkyl, to form the free amine (6), which can then be alkylated with an alkylating agent such as amino-protected piperidine, for example, N-tert-butoxycarbonyl-3-(3-bromopropyl)piperidine or with 2-chloro ethylmethyl sulfide using sodium hydride in an aprotic polar solvent such as dimethylformamide to form (7). Temperatures of from about 20° C. to 80° C. are preferred and the reaction is substantially complete within 4 hours. Deprotection of the piperidyl group may be accomplished by techniques familiar to the skilled artisan such as by treatment of (7) with an acid such as hydrochloric acid. Conversion to the sulfoxide can be achieved by treatment with an oxidizing agent, such as m-chloroperbenzoic acid.

Scheme I(b)

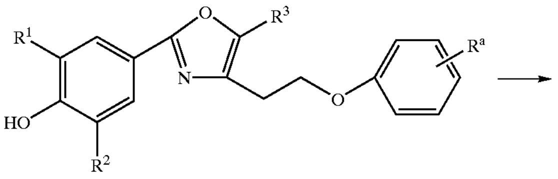

(4)

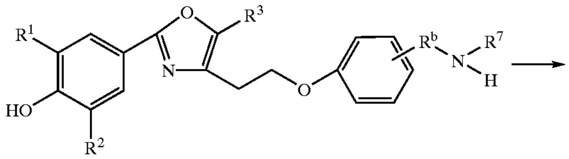

(6)

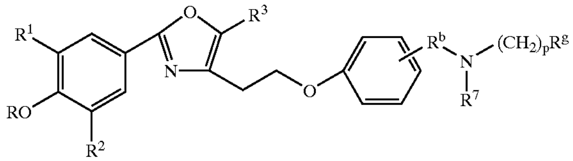

(7)

$R^a$ is oxo-substituted $C_1$–$C_6$ alkyl $R^b$ is $C_1$–$C_6$ alkyl

O
||
$R^g$ is piperidyl, S($C_1$–$C_6$)alkyl or ($C_1$–$C_6$)alkyl

Compounds of formula I where Ar is phenyl substituted with one or two straight chain —($C_2$–$C_6$ alkyl)$R^6$ groups and X, Y and $R^4$ are as defined in Scheme I(a) above can be prepared as described in Schemes I(c–e) below.

Scheme I(c)

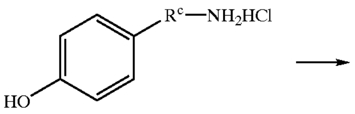

(8)

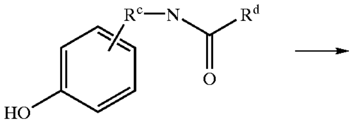

(9)

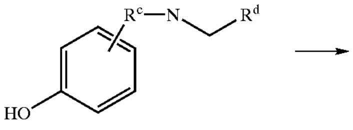

(10)

-continued

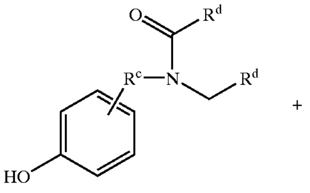

(11)

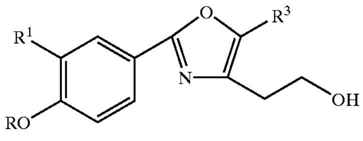

(3)

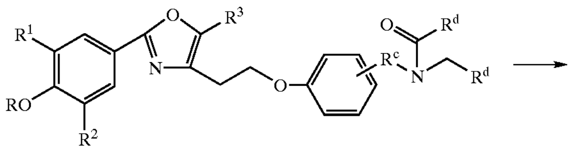

(12)

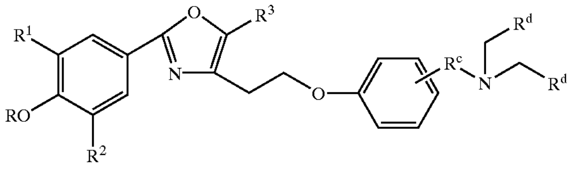

(13)

$R^c$ is $(CH_2)_q$ where q is an integer from 2-6

$R^d$ is H or —($C_1$–$C_5$)alkyl

In Scheme I(c), an amino-substituted phenol starting material (8) is reacted with an acylating agent such as acetic anhydride and sodium methoxide in a low molecular weight alcohol, such as methanol, to form compound (9). Reduction of the carbonyl can be achieved with a reducing agent, such as lithium aluminum hydride in an aprotic solvent, such as tetrahydrofuran, to produce compound (10). Acylation of (10) can be accomplished by reacting 1,1-carbonyldiimidazole with a carboxylic acid in an aprotic polar solvent such as tetrahydrofuran at temperatures of from about 0° C. to about 20° C., then treating with N-ethyl-p-hydroxyphenethyl amine (10). The reaction is substantially complete in 2 to 24 hours.

Compound (11) can then be coupled with an appropriately substituted phenyloxazole in a Mitsunobu reaction to prepare (12). The reaction can be conducted in a polar aprotic solvent such as tetrahydrofuran at ambient temperature. After approximately 24 hours, the reaction is substantially complete. Compound (12) can then be reduced using a reducing agent, such as aluminum hydride in an aprotic solvent, such as tetrahydrofuran, to prepare (13). The reaction is appropriately conducted at ambient temperatures and is complete in about three hours.

In an alternate procedure, as shown in Scheme I(d) below, an appropriately substituted phenylalkanol starting material (14), dissolved in an organic solvent such as methylene chloride, is reacted with a halogenating agent such as dibromotriphenylphosphorane to prepare compound (15). The reaction may be conducted at ambient temperature and allowed to proceed for about four hours.

The halogenated compound (15) is then coupled with an appropriately substituted phenyl oxazole in a Mitsunobu reaction to prepare (16) followed by displacement of the halogen with an amine of the formula —$NR^7R^8$ in a polar aprotic solvent such as dimethylformamide at about 80° C. for about five hours to prepare the desired final product.

Scheme I(d)

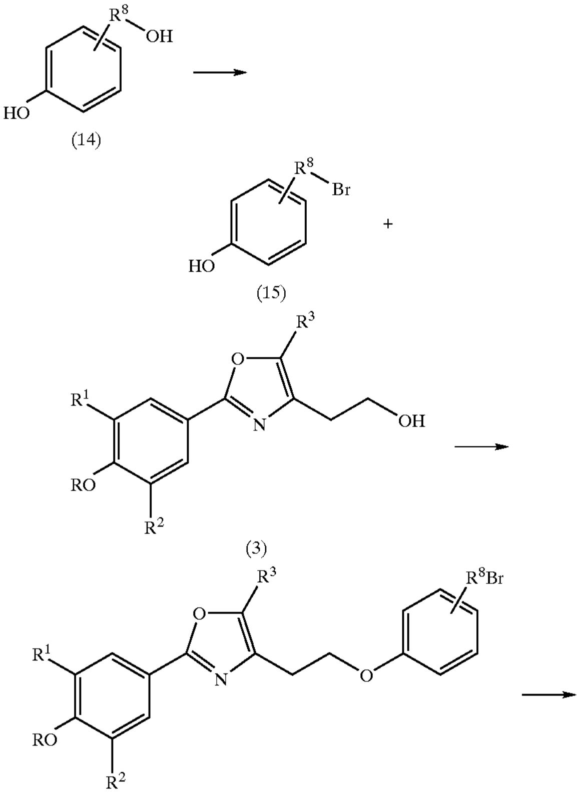

(14)

(15)

(3)

(16)

$R^e$ is ($C_2$–$C_6$ alkyl)
A is halo

Scheme I(e) below describes a third procedure for preparing compounds of formula I where Ar is phenyl substituted with one or two straight chain —($C_2$–$C_6$ alkyl)$R^6$ groups.

In a Mitsunobu reaction, compound (17) is first coupled with an appropriately substituted phenyl oxazole to form the intermediate oxazole (18). Reduction of the cyano group followed by hydrolysis prepares compound (19). Amination of compound (19) is achieved by either method described in Scheme I(a), step (e).

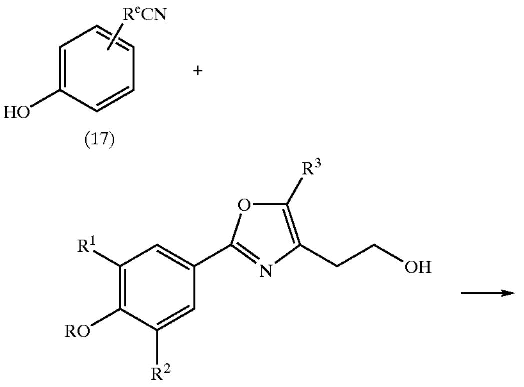

(17)

(3)

-continued

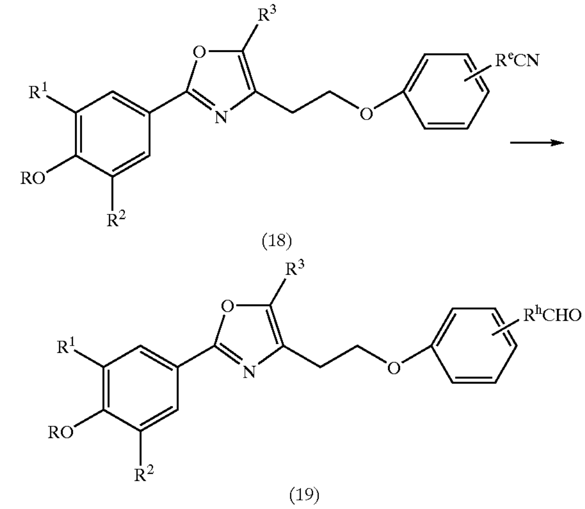

(18)

(19)

$R^h$ is ($C_1$–$C_5$) alkyl

Compounds of formula I where Ar is phenyl substituted with one or two

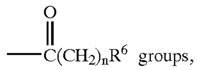

groups, and X and Y are as defined in Scheme I(a–e) above can be prepared as outlined in Scheme II below.

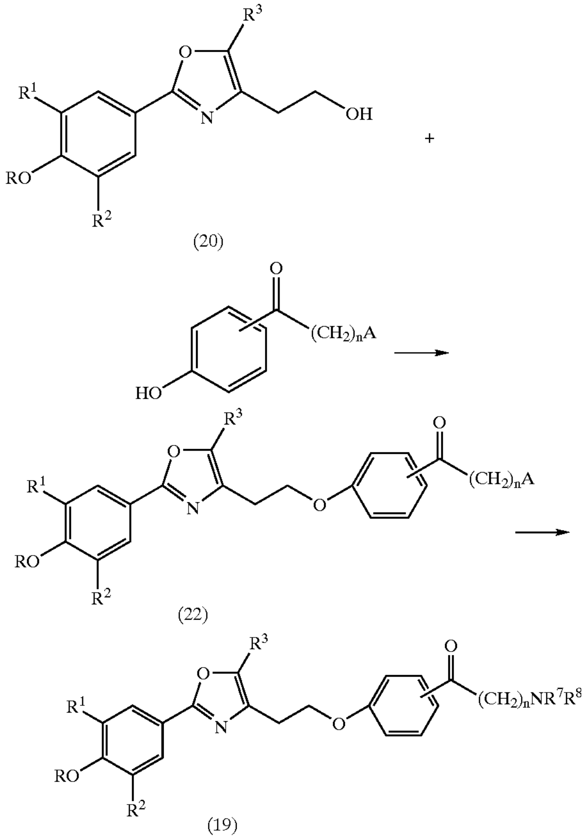

(20)

(22)

(19)

-continued

A is halo

In the above reaction Scheme II, an appropriately substituted phenyl oxazole (20), dissolved in an aprotic polar solvent such as tetrahydrofuran, is coupled with an appropriately substituted phenol (21) in a Mitsunobu reaction to form (22). At ambient temperatures, the reaction is substantially complete in 5 hours. Compound (22) is then treated with sodium iodide to form the iodoketone which is then displaced using an appropriately substituted amine while heating to about 50° C–80° C. The amination can be conducted in a non-polar organic solvent such as toluene and is substantially complete in about three hours.

Compounds of formula I where Ar is phenyl substituted with one or two branched —($C_1$–$C_6$ alkyl)$R^6$ groups, and X and Y are as described in Scheme I(a–e) above can be prepared according to Scheme III below.

Scheme III

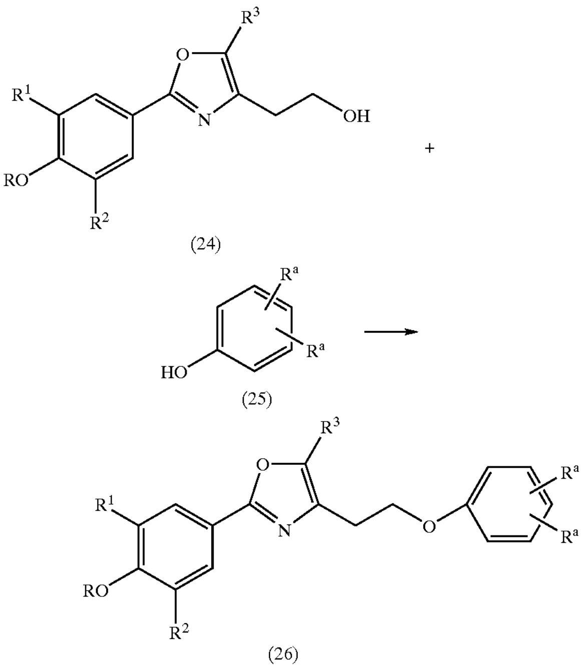

(24)

(25)

(26)

$R^a$ is oxo substituted —($C_1$-$C_6$)alkyl

An appropriately substituted phenyloxazole (24), dissolved in an aprotic polar solvent such as tetrahydrofuran, is coupled with an appropriately substituted ketone (25) in a Mitsunobu reaction to form compound (26). Reductive amination of (26) can be achieved by either of the methods described in Scheme I(a), step (e).

Compounds of Schemes I, II or III wherein Ar is phenyl additionally substituted with one or two substituents selected from —($C_1$–$C_6$)alkyl, halo and hydroxy can be prepared as shown in Scheme IV below.

Scheme IV

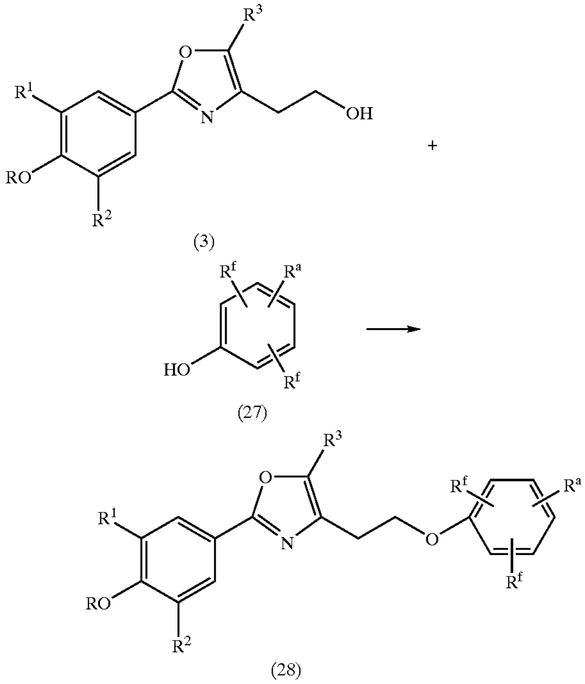

(3)

(27)

(28)

$R^a$ is oxo-substituted —($C_1$-$C_6$)alkyl
$R^f$ is hydrogen —($C_1$-$C_6$)alkyl, halo or protected hydroxy An appropriately substituted phenyl oxazole and appropriately substituted phenol (27) are coupled in a Mitsunobu reaction as described in Scheme I(a), step (d), to form the intermediate compound (28) which can then be aminated using either of the two methods described in Scheme I(a), step (e). The hydroxy may then be deprotected where appropriate.

Compounds of Schemes I, II or III where Ar is phenyl substituted with two substituents which, when taken together, form a phenyl ring can be prepared as shown in Scheme V below.

Scheme V

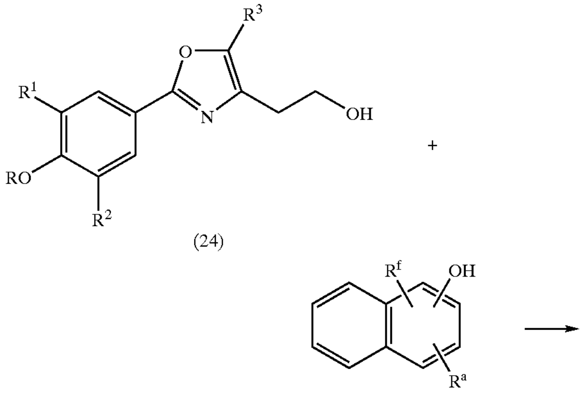

(24)

(25)

$R^a$ is oxo-substituted —($C_1$-$C_6$) alkyl
$R^f$ is hydrogen, —($C_1$-$C_6$) alkyl, halo or protected hydroxy Using a Mitsunobu coupling, a phenyloxazole starting material is reacted with an appropriately substituted hydroxynaphthaldehyde (29). The resulting product can then be subjected to reductive amination using either method of Scheme I, step (e) and the hydroxy deprotected where appropriate.

Compounds of Schemes I, II or III where Ar is phenyl substituted with

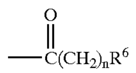

and/or —($C_1$–$C_6$ alkyl)$R^6$; where $R^6$ is morpholin-1-yl, piperazin-1-yl, thiomorpholin-1-yl or substituted piperazin-1-yl are prepared according to reaction Scheme VI.

Scheme VI

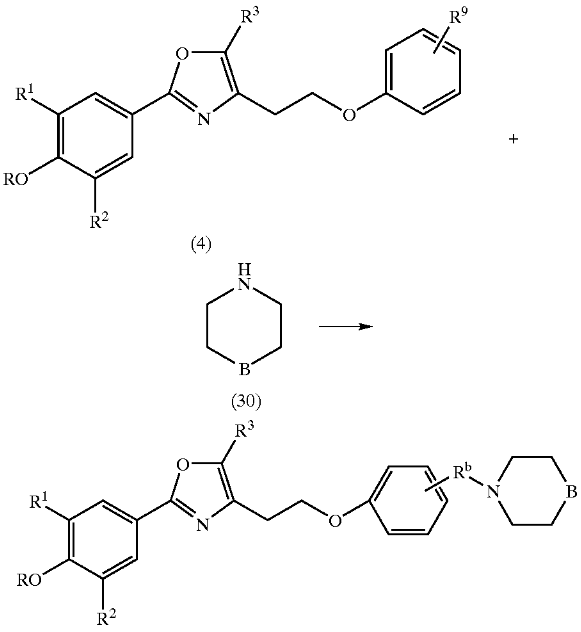

(4)

(30)

(31)

where B is —O—, —NH—,

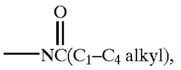

—N($C_1$–$C_4$ alkyl) or —S—, $R^a$ is oxo-substituted —($C_1$–$C_6$)alkyl and Rb is —($C_1$–$C_6$)alkyl An appropriately substituted starting material (30) is coupled by reductive amination with an appropriately substituted phenyloxazole according to the reactions of Scheme I(a), Step (e), i.e., using either a reducing agent such as sodium cyanoborohydride in an aprotic polar solvent such as tetrahydrofuran, or titanium IV isopropoxide ($Ti(OiPr)_4$) and sodium borohydride in a low molecular weight alcohol such as ethanol to form (31).

Compounds of Formula I where $R^6$ is piperazin-1-yl can be prepared by treating compound (31) of Scheme VI, where B is

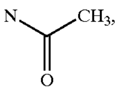

with an excess of an inorganic acid such as hydrochloric acid.

Compounds of formula I where $R^6$ is imidazol-1-yl are prepared according to the following Scheme VII.

Scheme VII

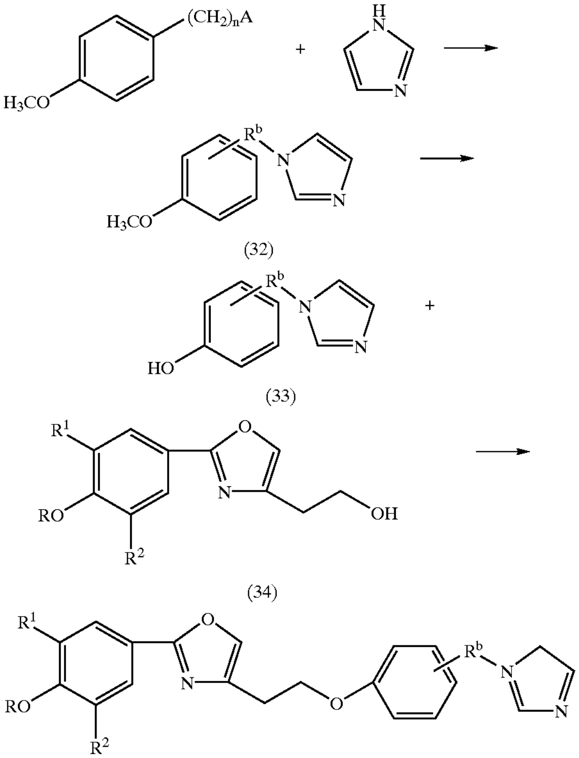

(32)

(33)

(34)

(35)

$R^b$ is $C_1$–$C_6$alkyl
A is halo

A methoxyphenylalkylhalide such as p-methoxybenzyl chloride is refluxed with imidazole to form (32). The reaction, conducted in a polar organic solvent such as acetonitrile, is substantially complete in about 16 hours. Demethylation of (32) is achieved by treatment with an agent, such as boron tribromide, to form compound (33). In a Mitsunobu coupling, compound (33) can be coupled with the phenyloxazole (34) to form the desired product (35).

Compounds of formula I where $R^6$ is 4,5-dihydro-1-H-imidazol-2-yl are prepared according to Scheme VIII.

Scheme VIII

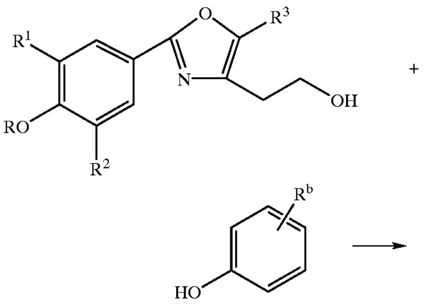

-continued

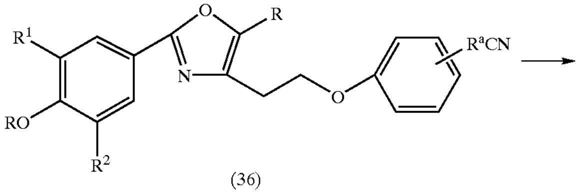

(36)

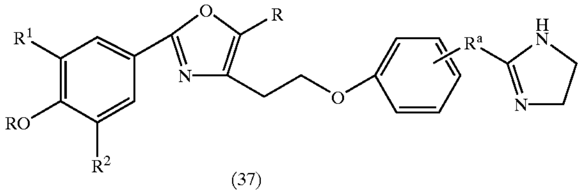

(37)

$R^a$ is -($C_1$–$C_6$) alkyl

A phenyloxazole starting material is coupled with a hydroxyphenylalkyl cyanide compound in a Mitsunobu reaction. Cyclization of the cyano group to form the dihydroimidazole (37) can be achieved by first, treating (36) with hydrogen chloride gas in ethanol at low temperatures for about four hours then refluxing with ethylenediamine for an additional period of up to 32 hours.

Compounds of formula I where Ar is phenyl substituted with two substituents which when taken together with the carbons to which they are attached form a pyridyl or tetrahydropyridyl can be prepared according to Schemes IX(a) and IX(b) below.

Scheme IX(a)

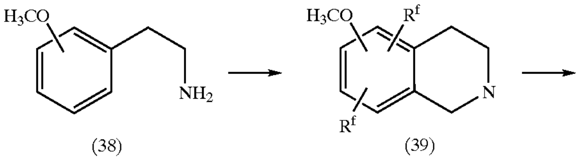

(38) (39)

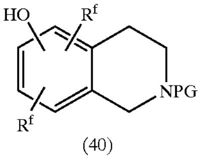

+

(40)

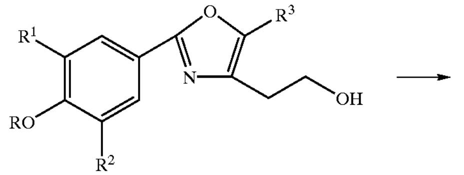

(3)

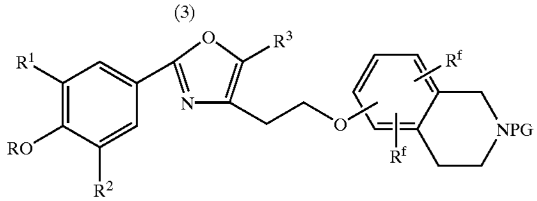

(41)

PG is a protecting group

Rf is hydrogen, -($C_1$–$C_6$) alkyl halo or protected hydroxy

Scheme IX(b)

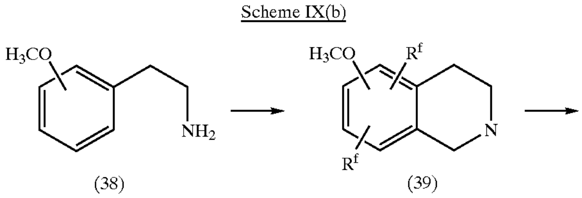

(38) (39)

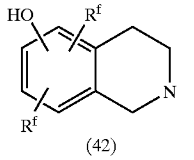

+

(42)

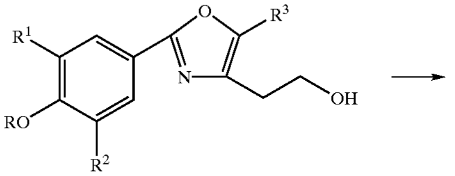

(3)

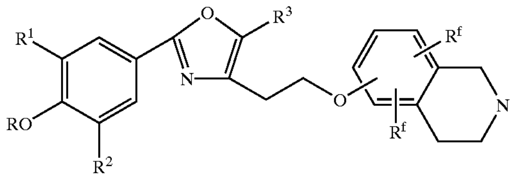

(43)

Rf is hydrogen, -($C_1$–$C_6$) alkyl, halo or protected hydroxy.

In the above reaction Schemes IX(a) and IX(b), starting material (38) is cyclized with the appropriate aldehyde in an acid solution to form intermediate (39) as an oxalate salt.

In Scheme IX(a), intermediate (39) can first be demethylated by refluxing the oxalate salt (38) with hydrogen bromide then protecting the nitrogen with an amino-protecting agent such as di-tert-butyl dicarbonate to prepare (40).

In Scheme IX(b), the free amine (39) can be aromatized in the presence of dehydrogenating reagent by heating with palladium black followed by demethylation, as discussed above, to form (42).

Compounds (40) or (42) can then be coupled with an appropriately substituted phenyloxazole in a Mitsunobu reaction, to form the desired products (41) or (43). Removal of the nitrogen protecting group can be achieved by standard methodology such as by treatment with trifluoroacetic acid and an appropriate t-butyl cation scavenger such as thiophenol. If a hydroxy protecting group is employed, the hydroxy group may be deprotected by, for example, hydrolysis or treatment with an acid depending on the protecting group selected.

Compounds where Ar is substituted pyridyl can be achieved by the following general reaction Scheme X Scheme X

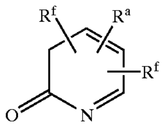

+

-continued

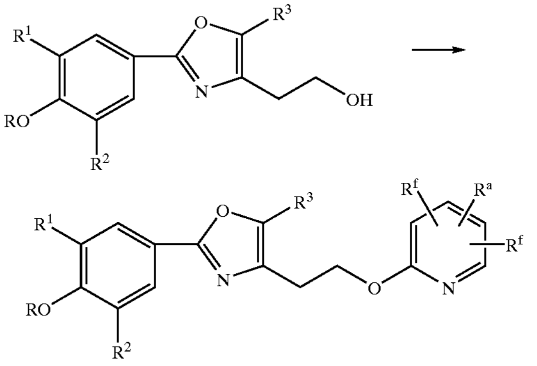

(44)

$R^a$ is oxo-substituted -($C_1$–$C_6$) alkyl
$R^f$ is hydrogen, -($C_1$–$C_6$ alkyl), halo or protected hydroxy Using an appropriately substituted pyridone carboxaldehyde and an appropriately substituted phenyloxazole in a Mitsunobu coupling reaction, compound (44) is prepared. When $R^f$ is a protected hydroxy group, it may be deprotected after the coupling step. Compound (44) can then undergo reductive amination using either process described in Scheme I(a), step (e) above.

Compounds of formula I where Y is sulfur can be prepared as illustrated in Scheme XI below.

Scheme XI

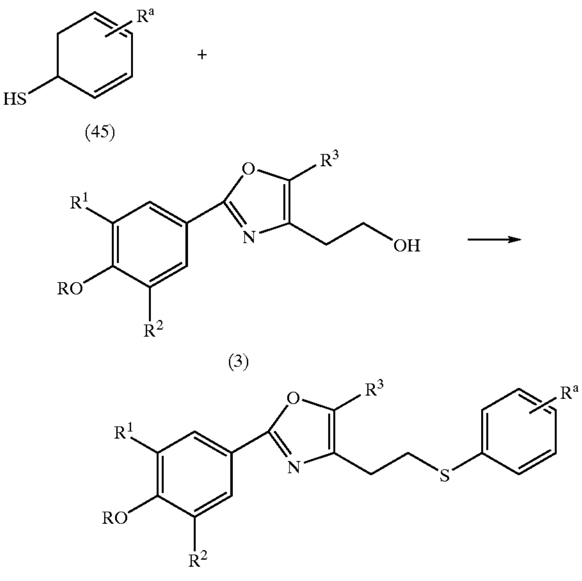

(45)

(3)

(46)

$R^a$ is oxo-substituted —($C_1$–$C_6$)alkyl

An appropriately substituted phenyloxazole is coupled with an appropriately substituted mercaptobenzaldehyde (45) in a Mitsunobu reaction. The resultant intermediate (46) can then be reduced to the desired amine using either of the reductive amination reactions described in Scheme I(a), step (e).

Compounds of formula I where $R^3$ is —($C_1$–$C_6$)alkyl and R, $R^1$, $R^2$, $R^4$, X and Y are as described above can be prepared as follows:

Scheme XII

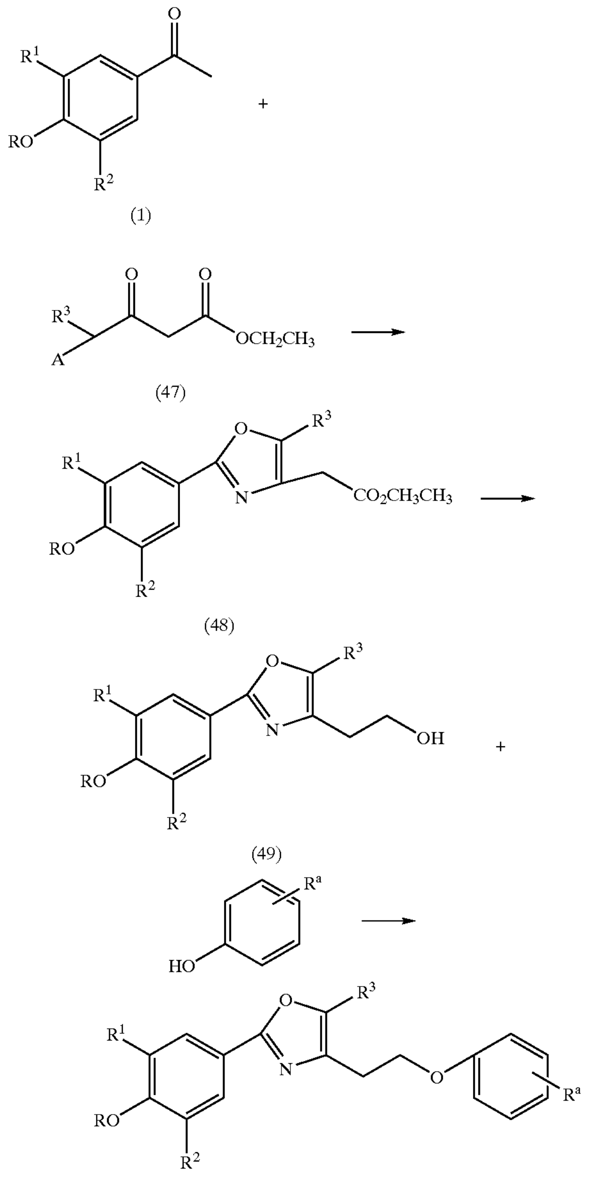

(1)

(47)

(48)

(49)

(50)

A is halo
$R^a$ is oxo-substituted —($C_1$–$C_6$)alkyl

Potassium ethyl malonate is stirred with a metal halide, such as magnesium chloride and a base, such as triethylamine, in an aprotic polar solvent such as acetonitrile under an inert gas such as nitrogen at ambient temperatures then reacted with an acid halide such as $\mu$-chloro-propionyl chloride to form starting halide (47).

Intermediate (48) is formed by reacting the halide (47) with an appropriately substituted benzamide (1), prepared as described in Scheme I(a) above. The reaction is allowed to proceed at temperatures of about 100° to 150° C. under an inert gas such as nitrogen for about 1 to 8 hours.

Reduction of intermediate (48) with a reducing agent such as lithium aluminum hydride affords compound (49). The reduction is conducted under an inert gas such as nitrogen in an aprotic polar solvent or ether such as tetrahydrofuran for a period of from 1–24 hours.

Using a Mitsunobu coupling, an appropriately substituted benzaldehyde is combined with intermediate (49) to form compound (50) which can then be reduced by reductive amination as described in Scheme I(a), step e, above to form the desired product.

Compounds of formula I where X is S can be prepared as follows:

Scheme XIII

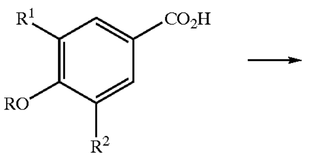

(51)

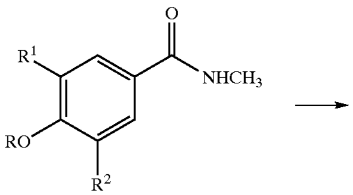

(52)

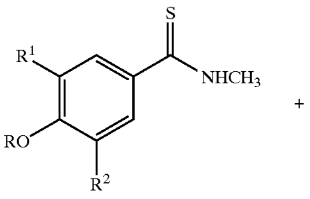

(53)

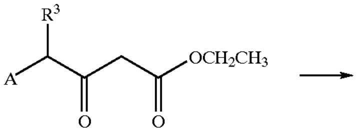

(54)

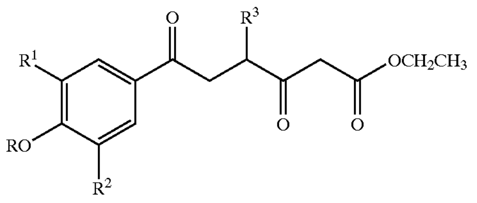

(55)

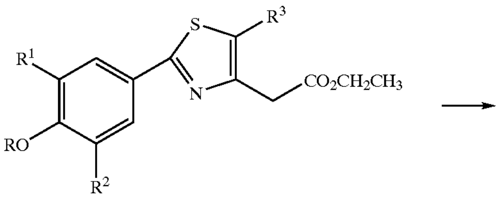

(56)

-continued

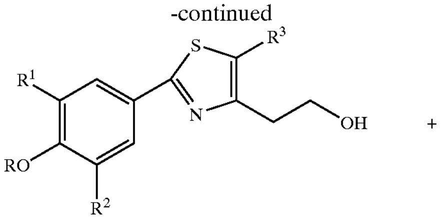

(57)

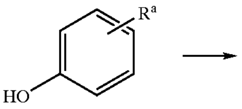

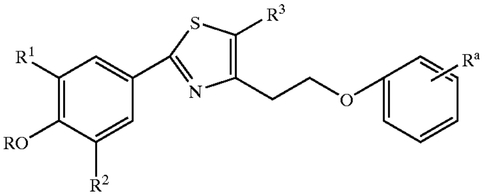

(58)

A is halo $R^a$ is oxo-substituted —($C_1$–$C_6$)alkyl

Benzamide (52) is prepared by refluxing an appropriately substituted benzoic acid with an activating agent such as carbonyldiimidazole under an inert gas such as nitrogen, then reacting with methylamine as described in Scheme I, Step (a) above. Using an aprotic polar solvent such as tetrahydrofuran, the reaction is substantially complete in about 2–24 hours.

Conversion to the thiobenzamide (53) is achieved by reacting (52) with Lawessens reagent at temperatures of from 80° C. to 120° C. in an organic solvent such as hexamethylphosphoramide under an inert gas such as nitrogen for about 1 to 2 hours.

The synthesis of intermediate (55) is accomplished by refluxing the thioamide (53) under an inert gas such as nitrogen with an u-haloketone such as ethyl 4-chloroacetoacetate in the presence of potassium iodide. An aprotic polar solvent or ether such as tetrahydrofuran is preferred and the reaction is complete within 1 to 6 hours.

Cyclization to prepare the thiazole (56) is achieved by reacting thioester (55) with an excess of ammonium acetate in acid such as acetic acid under an inert gas such as nitrogen for from 1 to 5 hours.

Reduction of the thiazole ester (56) is accomplished with a reducing agent such as lithium aluminum hydride. The reduction is preferably conducted under an inert gas such as nitrogen in an aprotic polar solvent such as tetrahydrofuran. The reaction is substantially complete in 1 to 2 hours.

Using a Mitsunobu reaction, the thiazole intermediate (57) can be coupled with an appropriately substituted benzaldehyde to form (58) which can be isolated and purified and reduced to the desired amine by reductive amination as described in Scheme I(a), step (e) above.

Compounds of formula I where Y is $CHR^5$, where $R^4$ and $R^5$ are individually hydrogen or $R^4$ and $R^5$ taken together form a bond can be prepared according to Scheme XIV as follows.

Scheme XIV

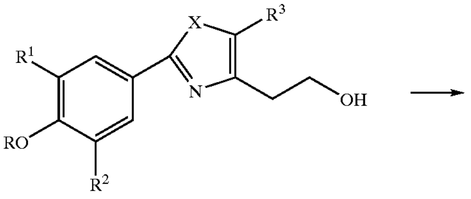

(59)

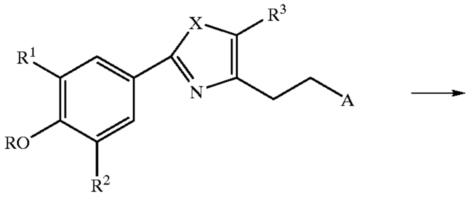

(60)

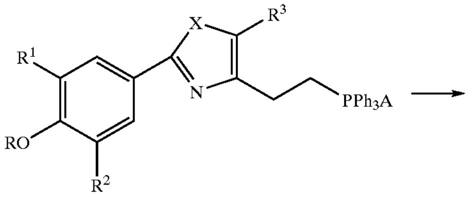

(61)

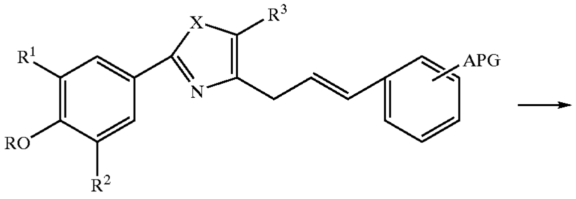

(62)

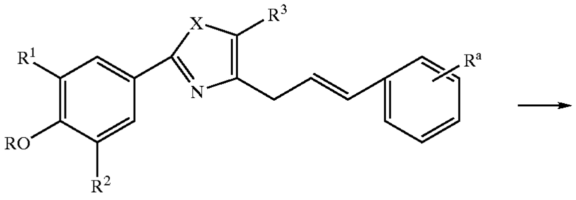

(63)

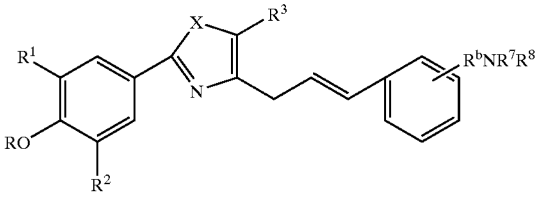

(62)

A is halo
$R^a$ is oxo-substituted —$(C_1$–$C_6)$alkyl
APG is a protected aldehyde At ambient temperature, in a polar solvent such as methylene chloride, an appropriately substituted starting alcohol (59) is halogenated by treatment with a halogenating agent such as triphenylphosphine and bromine in the presence of a base or acid scavenger such as imidazole. The reaction is substantially complete in 1–24 hours.

In a displacement reaction, the halogenated compound (60) is refluxed with triphenylphosphine in a nonpolar solvent such as xylene for about 24 hours to form the activated intermediate (61).

Intermediate (62) is prepared in a Wittig reaction using a strong base such as sodium hexamethyldisilazane and an appropriately protected aldehyde such as terephthalaldehyde mono-(diethylacetal). The reaction is preferably conducted in an aprotic polar solvent such as tetrahydrofuran at temperatures of from about −20° C. to about 0° C. and is substantially complete in about 3 to 10 hours.

It will be readily appreciated by the skilled artisan that intermediate (62) forms the E and Z isomers which may be readily separated by conventional chromatographic techniques.

The desired aldehyde (63) may then be deprotected by treatment with an aqueous acid such as hydrochloric acid for about 24 hours. Deprotection is preferably conducted in a polar solvent or ether such as diethylether at ambient temperature.

Reductive amination can be accomplished using either of the procedures described in Scheme I(a), Step (e).

Compounds of formula I where Y is —$CHR^5$ and $R^5$ is hydrogen can be prepared by hydrogenation of compound (64) with hydrogen gas and 5% palladium on carbon. The reduction is preferably conducted in a non-polar solvent such as toluene at ambient temperatures and is substantially complete in about four hours.

Compounds of formula I where Ar, X and Y and $R^4$ are as defined as in Scheme I(a) above, and m=0 can be prepared as demonstrated in Scheme XV below.

Scheme XV

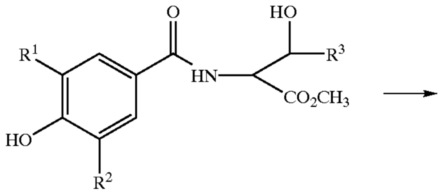

(66)

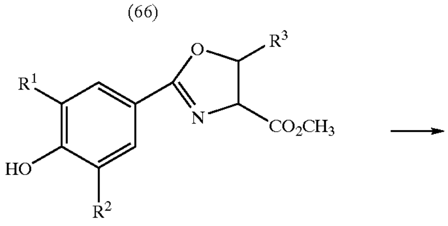

(67)

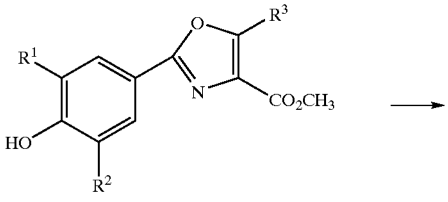

(68)

-continued

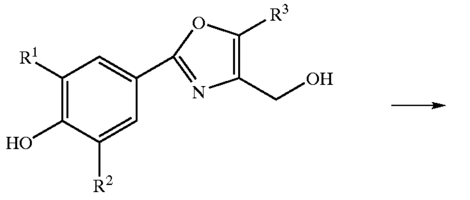

(69)

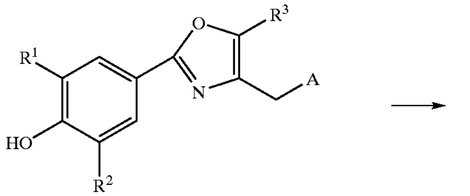

(70)

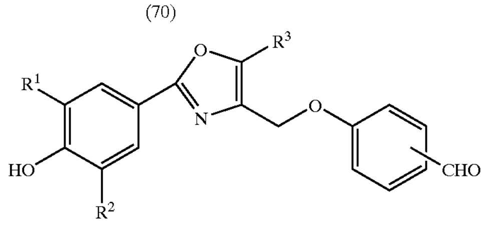

(71)

A is halo

Starting material (66) is achieved by treating an appropriately substituted benzoic acid with a peptide coupling reagent, such as CDI, DCC or, preferably, CDMT, to form an activated acylating agent. The reaction is preferably conducted in an aprotic solvent, such as methylene chloride, at temperatures of from about −5° C. to ambient temperature, preferably ambient temperatures. The activated intermediate is then reacted with an appropriately substituted serine compound preferably d,l-serine methyl ester. The reaction is conducted at temperatures from −30° C. to ambient temperature, preferably at about −10° C.

The methyl ester (66) may be cyclyzed to the oxazoline (67) by reacting with a brominating agent, such as triphenylphosphine, and carbon tetrabromide in the presence of a base. The reaction is conducted in an aprotic polar solvent, such as acetonitrile, at ambient temperature for from about 1 to 24 hours.

Preferably, cyclization of the methyl ester (66) is accomplished by treatment with thionyl chloride, preferably an equimolar quantity relative to the ester, using an aprotic solvent such as methylene chloride or tetrahydrofuran.

The oxazoline (67) is oxidized to compound (68) by refluxing with an oxidizing agent, preferably 2,3-dichloro-5,6-dicyano-1,4-benzoquinone (DDO). Other oxidizing agents, such as activated manganese oxide or $NiO_2$ are also useful. The reaction is preferably conducted in an aprotic solvent such as toluene, benzene or, preferably, dioxane and is substantially complete in 1 to 24 hours.

The oxazole (68) can then be reduced with a reducing agent, such as lithium borohydride-methanol reducing system or, preferably, lithium aluminum hydride in an aprotic polar solvent, such as tetrahydrofuran. The reaction is initiated at temperatures from −10° C to ambient temperature, preferably at about 0° C., and then stirred at ambient temperature for from 30 minutes to 12 hours.

Halogenation of (69) is accomplished by treatment with a halogenating agent such as triphenylphosphine and carbon tetrabromide, phosphorus tribromide, phosphorus pentabromide, carbon tetrabromide or boron triphenylphosphine,preferably phosphorus tribromide, in an aprotic polar solvent such as methylenechloride or acetonitrile. The reaction is preferably conducted at ambient temperatures for from 1–24 hours but may also be accomplished at temperatures of from −10° C. to ambient temperatures.

In a displacement reaction under Finkelstein conditions, the halogen is replaced with an appropriately substituted benzaldehyde.

Reductive amination of (70) as described in Scheme I(a), Step (e), above yields the desired product (71).

Compounds of formula 1 where Ar, X and Y and $R^4$ are as defined as in Scheme 1(c–e), above, and m=0 can be prepared as demonstrated in Scheme XVI below.

Scheme XVI

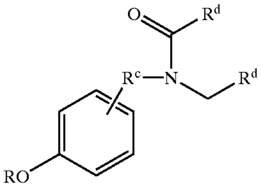

\+

(11)

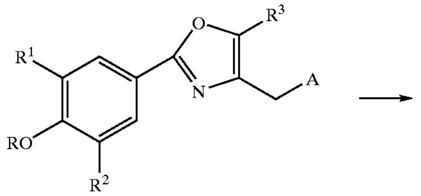

(70)

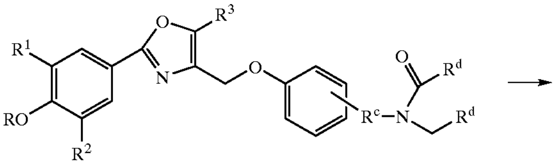

(72)

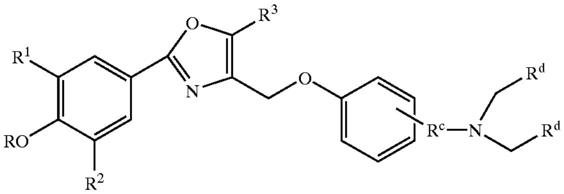

(73)

$R^c$ is $(CH_2)_q$ where q is an integer from 2-6
$R^d$ is H or C1–C5 alkyl
A is halo Starting material (11) is coupled with oxazole starting material (70) in the presence of a base, such as sodium hydride in an aprotic solvent, preferably tetrahydrofuran. The reaction is preferably conducted at ambient temperatures for from 1 to 24 hours to prepare intermediate amide (72).

Reduction of intermediate (72) can be accomplished by treatment with a reducing agent, such as borane-dimethylsulfide, to prepare (73).

Alternately, the coupling reaction can be accomplished by reacting (70) with (116) (prepared as described in Scheme I(a)(3)) followed by reduction of the carbonyl with a reducing agent, such as borane. The reaction is conducted in an aprotic solvent, preferably tetrahydrofura, at ambient temperatures.

Compounds where m is 2 can be prepared as described in Scheme XVII, below.

Scheme XVII

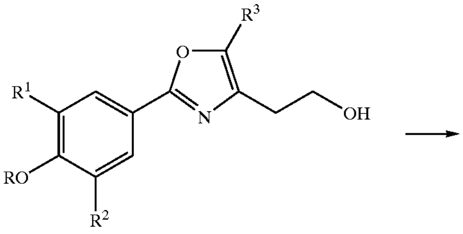

(59)

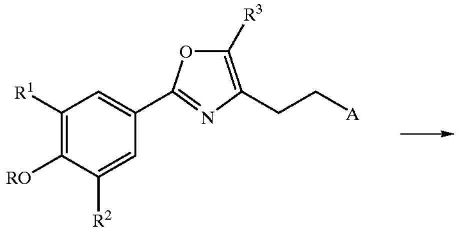

(60)

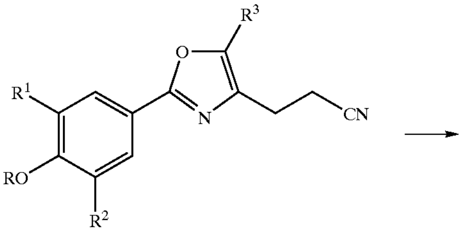

(74)

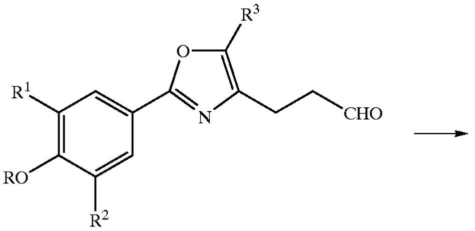

(75)

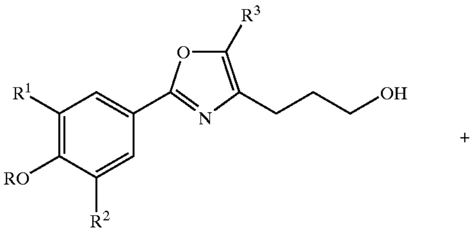

(76)

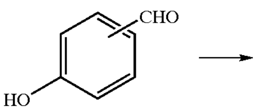

-continued

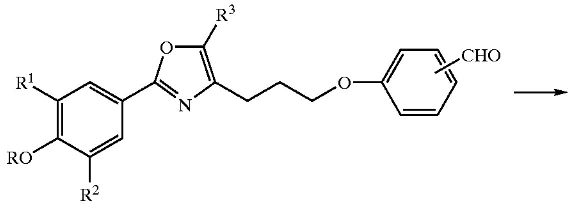

(77)

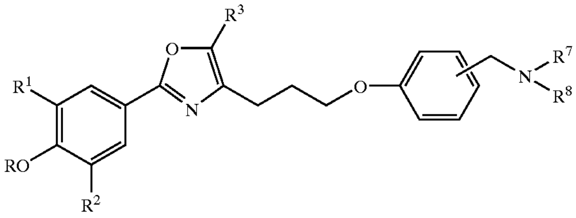

(78)

A is halo

Starting material (59) is reacted with a halogenating agent such as triphenyiphosphine and iodine, in the presence of a weak base. The reaction can be conducted in an aprotic polar solvent at ambient temperatures for from 1 to 24 hours.

In displacement reaction, the halogenated compound (60) is heated with sodium cyanide in an aprotic polar solvent such as dimethylsulfoxide for about 1 to 2 hours to form the intermediate cyano compound (74).

The cyano compound (74) can then be reduced with a reducing agent, such as diisobutylaluminum hydride, in a nonpolar solvent, such as toluene. Preferably, the reaction is initiated at −78° C. and then allowed to warm to ambient temperature for 1 to 2 hours.

The formyl compound (75) can then be reduced with a reducing agent, such as sodium borohydride, in a solvent such diethylether to prepare intermediate (76).

Mitsunobu coupling of intermediate (76) with the appropriately substituted hydroxy benzaldehyde gives (77) which can be isolated, purified and converted to the desired amine (78) by reductive amination.

Preparation of compounds where $R^1$ and $R^2$ are each independently —$(C_1$–$C_6)$alkoxy are prepared as described in Scheme XVIII, below.

Scheme XVIII

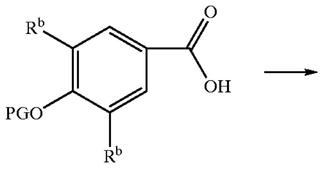

(79)

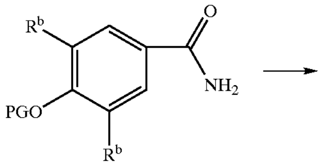

(80)

-continued

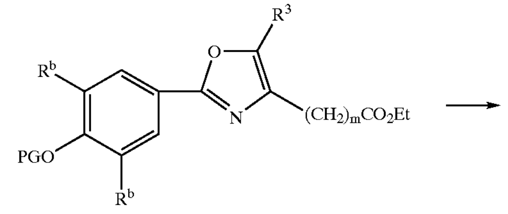

(81)

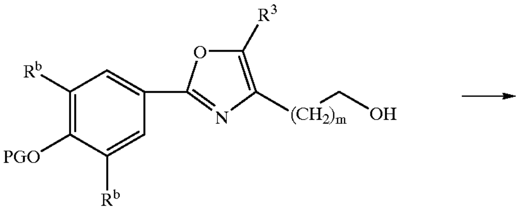

(82)

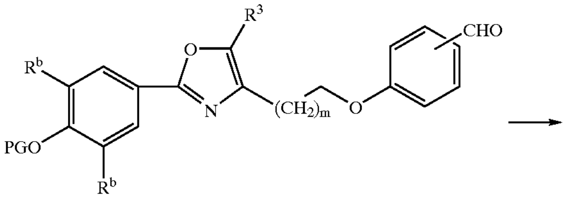

(83)

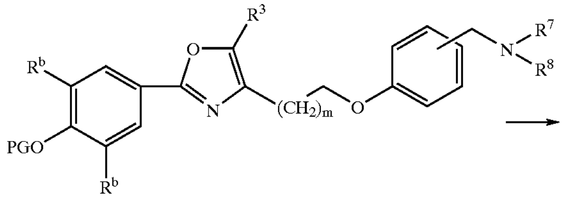

(84)

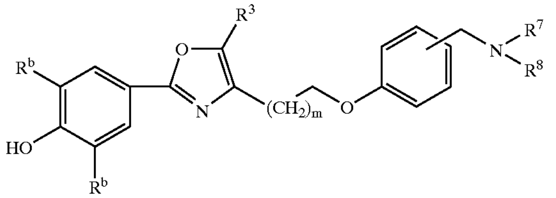

(85)

PG is a protecting group $R^b$ is —$(C_1$-$C_6)$alkyl

Following the procedure described in Scheme I(a), Step (a), above, appropriately substituted benzoic acid (79) is converted to the intermediate benzamide (80).

Intermediate benzamide (80) may then by cyclized to form the ester (81) by heating at temperatures from 500 to 130° C. with 4-chloroacetoacetate under an inert gas.

Reduction of the ester using, for example, lithium aluminum hydride affords the primary alcohol (82).

Following the procedure outlined in Scheme I(a), steps (d) and (e), amine (84) is prepared. Removal of the protecting group by, for example, hydrolysis achieves desired product (85).

Compounds where R3 and R4 taken together with the ring to which they are attached form a benzoxazole group are prepared as described in Scheme XIX, below.

Scheme XIX

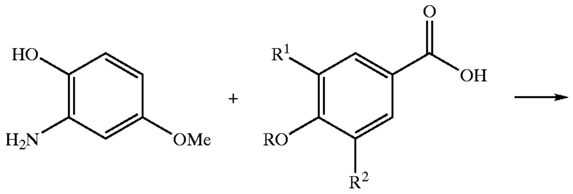

(86)

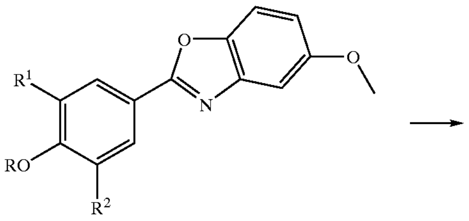

(87)

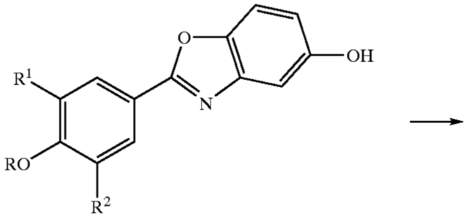

(88)

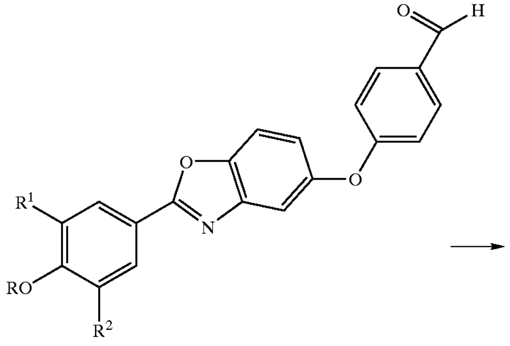

(89)

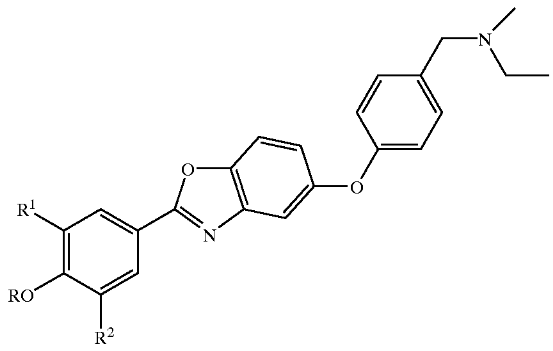

(90)

An appropriately substituted benzoic acid (81) is coupled with 2-hydroxy-5-methoxyaniline in the presence of an acid, such as boric acid, to form the intermediate benzoxazole (87).

Demethylation of (87) using, for example, borontribromide accomplishes the alcohol (88). Preferably, the reaction is conducted in an organic solvent such as methylene chloride at temperatures of about −10° to −70° C.

Preparation of (89) is achieved in an Ullman reaction by heating (88), preferably at temperatures of about 140° C., with an appropriately substituted arylhalide, such as 4-bromobenzoldehyde in the presence of potassium carbonate and copper iodide.

Reductive anination, as described in Scheme I(a), step (e), affords (90).

Compounds where X is —O— and Y is —N— are accomplished as shown in Scheme XX.

Scheme XX

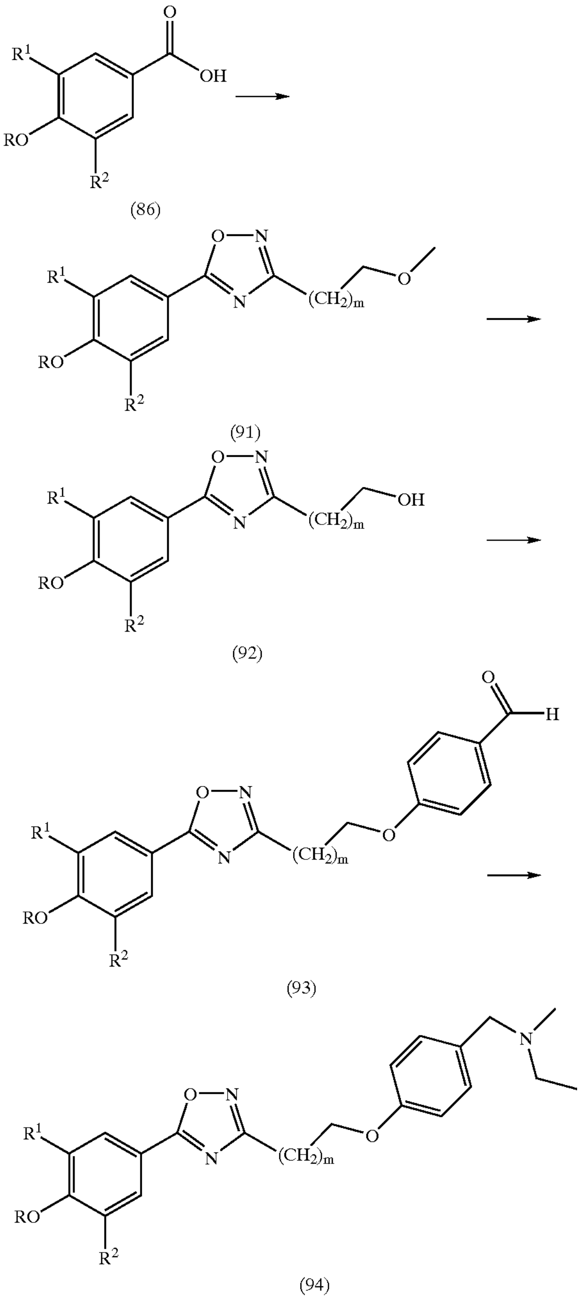

(86) (91) (92) (93) (94)

Oxadiazole (91) is prepared by, first, treating an appropriately substituted benzoic acid (86) with thionyl chloride to prepare the acid chloride intermediate which may then be reacted with the appropriately substituted alkylamidoxime, such as methylethylamidoxime.

Following steps (b)–(d) as described in Scheme XIX, above, desired product (94) is achieved.

Compounds where X is —O— and - - - is a single bond can be prepared as described in Scheme XIX below.

Scheme XXI

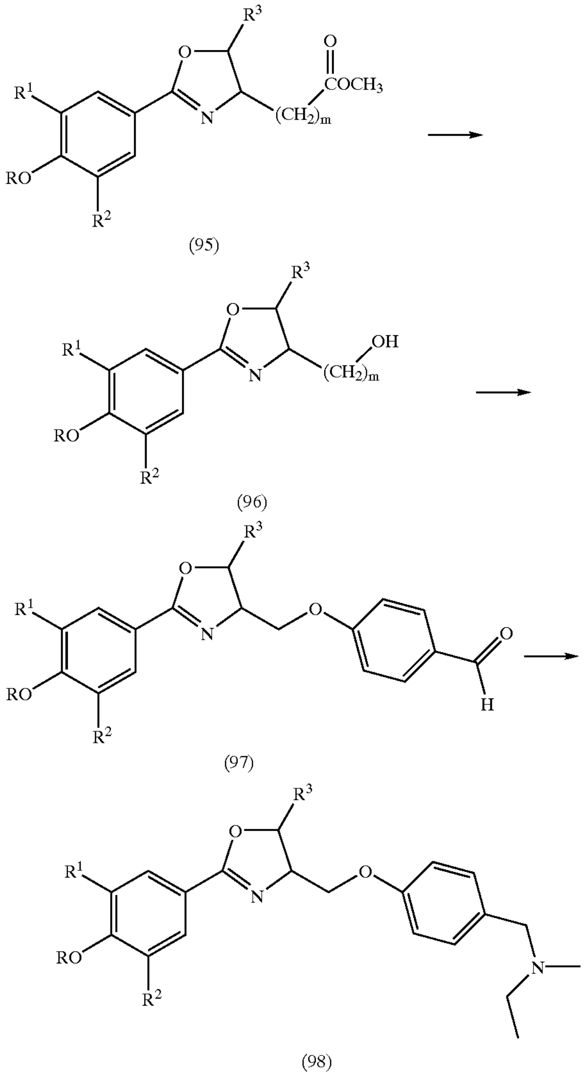

(95) (96) (97) (98)

Reduction of (95) is accomplished by treatment with a reducing agent such as lithium aluminum hydride. Preferably, the reaction is conducted in an aprotic polar solvent such as tetrahydrofuran at temperatures of around −10° C. to prepare the intermediate alcohol (96).

In a Mitsunobu coupling, as described in Scheme I(a), step (d), aldehyde (97) is prepared. Reductive amination, as described in Scheme I(a), step (e), affords (98).

Compounds where Ar is tetrahydronaphthyl are prepared as depicted in Scheme XXII.

Scheme XXII

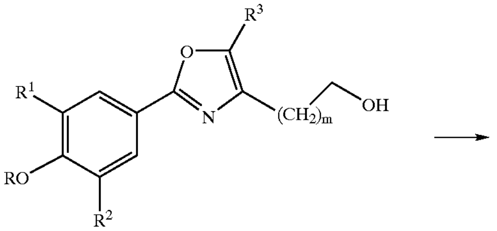

(96)

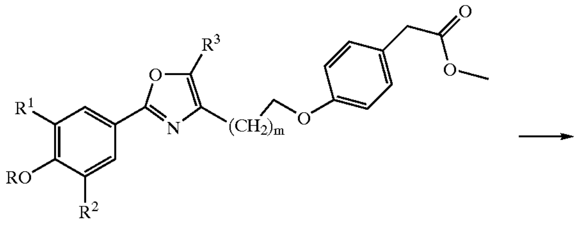

(99)

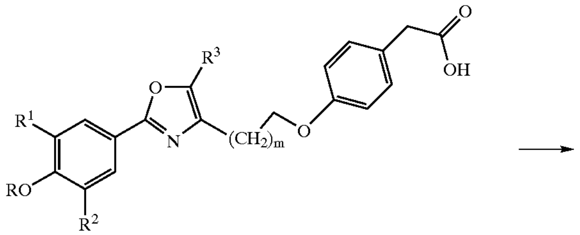

(100)

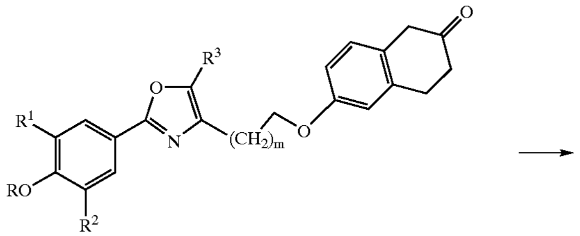

(101)

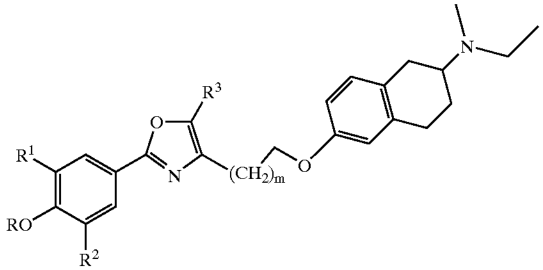

(102)

In a Mitsunobu coupling, as described in Scheme I, step (d), ester (99) is prepared. Hydrolysis of the ester is accomplished by treatment with a base, such as lithium hydroxide, to prepare the acid (100).

Cyclization to the tetrahydronaphthyl (101) is achieved by conversion of the acid first to the acid chloride, by treatment with, for example thionyl chloride, then by reacting the acid chloride intermediate with ethylene gas. Desired product (102) is accomplished by reductive amination as described in Scheme I, step (e).

The intermediates and final products may be isolated and purified by conventional techniques, for example by concentration of the solvents, followed by washing of the residue with water, then purification by conventional techniques such as chromatography or recrystallization.

When Ar is phenyl substituted with one or two ($C_1$–$C_6$ alkyl)$R^6$ groups, the present invention may have one or two stereo centers. The methods, formulations and compounds of the present invention encompass the diastereomers and the racemates and their individual stereo isomers. diastereomeric pairs may be obtained according to procedures well known in the art. For example, formation of a diastereomeric salt from a racemic amine can be accomplished by treatment with a chiral acid, such as tartaric acid or diisopropylidene-keto-gulonic acid.

It will be readily appreciated by the skilled artisan that the substituted benzoic acid, amide, amine, alcohol, aldehyde, heterocyclic, imidazole and thiophenol starting materials are either commercially available or can be readily prepared by known techniques from commercially available starting materials. All other reactants used to prepare the compounds in the instant invention are commercially available.

The following examples further illustrate the preparation of the compounds of this invention. The examples are illustrative only and are not intended to limit the scope of the invention in any way.

EXAMPLE 1

2-(3,5-di-t-Butyl-4-hydroxyphenyl)-4-(2-(4-ethylaminomethylphencxy)ethyl)oxazole Hydrochloride Dihydrate A. Preparation of 3,5-bis(1,1-Dimethylethyl)-4-hydroxybenzamide In a 22 L Morton flask, 749 g (3.0 mol) of 3,5-bis(1,1-dimethylethyl)-4-hydroxybenzoic acid, 533 g (3.3 mol) carbonyldiimidazole and tetrahydrofuran (THF) were combined and heated slowly to reflux and allowed to reflux for 2.5 hours. The reaction mixture was cooled to 26° C. and concentrated aqueous ammonia was added. Stirring was continued for 2 hours and the reaction mixture was allowed to stand overnight. The contents were transferred to a flask and rinsed with tetrahydrofuran (250 mL). The mixture was stirred, layers were separated, and the aqueous layer was saved. The organic layer was washed with brine (2.5 L) followed by brine/deionized (DI) water (1 L/1.5 L). The organic layer was washed with 9.7 M hydrochloric acid (HCl)/deionized water (0.25 L/2.25 L), followed by 9.7 M hydrochloric acid/deionized water (0.5 L/2.8 L), and 9.7 M hydrochloric acid/deionized water/brine (0.5 L/1.5 L/1.5 L). The organic layer was set aside while the combined aqueous layers were washed with tetrahydrofuran. The combined organic layers were washed with brine, dried with sodium sulfate (855 g) and filtered. The filtrate was evaporated to 1011 g of a wet (water), white solid. Methylene chloride was added and removed in vacuo. This procedure was repeated with ethyl acetate (6 L, then 2 L) to produce a solid residue (779 g). The residue was slurried in ethyl acetate and heptane, filtered, and dried in a vacuum oven to yield the desired amide (736 g, 98.7%) as a white solid mp 257–260° C.

$^1$H NMR (DMSO-$d_6$, 300 MHz) δ 7.75 (1H, s), 7.60 (2H, s), 7.30 (1H, s), 7.00 (1H, s), 1.35 (18H, s).

B. Preparation of 2-(3,5-di-t-Butyl-4-hydroxyphenyl)-4-(carboxymethyl)oxazole

To 24.90 g (100 mmol) of the compound of step A, 55 mL (407 mmol) of ethyl 4-chloroacetoacetate was added. The mixture was heated to 130° C. under nitrogen for 2 hours. The reaction mixture was cooled to 90° C. and the volatiles were distilled from the reaction mixture under vacuum until the pot temperature reached 130° C. The thick residue was allowed to cool to 60° C. under vacuum. The vacuum was released and 100 mL of methanol was added to the mixture. The solution was cooled to 25° C. and then 50% sodium hydroxide solution (50 mL) was added dropwise. The reaction mixture temperature increased to 55° C. The mixture was stirred 25 minutes, then concentrated aqueous hydrochloric acid (25 mL, 300 mmol) was added dropwise to the reaction mixture to bring the pH to 7–8. The mixture was filtered and the cake was washed with methanol (2×50 mL). The methanol was removed under vacuum, and then 1N hydrochloric acid (100 mL) and water (100 mL) were added. A gummy precipitate formed. The precipitate was dissolved by adding 500 mL of a 1:1 mixture of tert-butyl methyl ether (MTBE) and ethyl acetate. The resulting emulsion separated into three layers overnight. The upper layer, containing desired product by HPLC, was dried with sodium sulfate and concentrated in vacuo to give 30.8 g of a tan solid. This solid was dissolved in 2:1 methanol:water (225 mL) at 75° C. The stirred mixture was allowed to cool to 25° C. over 1 hour, and stirred for another 2.5 hours. The mixture was filtered and the cake was washed with a total of 120 mL of 2:1 methanol:water. Vacuum drying at 40° C. gave 21.94 g of the subtitled product. A 19.9 g portion of the acid was recrystallized from 300 mL of 1:1 heptane:toluene to give 17.77 g (62% overall yield) of the subtitled product as a white solid.

mp 166–68° C. $^1$H NMR DMSO d-6, 300 MHz) δ 12.49 (s, 1H, exchanges with $D_2O$), 7.93 (s, 1H, ), 7.72 (s, 2H), 7.54 (s, 1H, exchanges with $D_2O$), 3.56 (s, 2H), 1.41 (s, 18H). Elemental analysis for $C_{19}H_{25}NO_4$: Calculated: C, 68.86; H, 7.60; N, 4.23. Found: C, 68.86; H, 7.59; N, 4.32. FDMS 331 ($M^+$).

C. Preparation of 2-(3,5-di-t-Butyl-4-hydroxyphenyl)-4-(2-hydroxyethyl)oxazole

In a 22L flask, 757 g (2.28 mol) of the compound of step B was dissolved in tetrahydrofuran. To the solution was added, very slowly at first and with water-bath cooling, 1 M borane tetrahydrofuran (4.8 L) After 1 hour the reaction mixture was quenched with methanol (650 mL) very slowly due to hydrogen evolution. The mixture was allowed to stir overnight. The solution was placed on a rotary evaporator and evaporated to a foam (995 g). The residue was dissolved in tert-butyl methyl ether (11 L) and deionized water (4.9 L) and 50% sodium hydroxide (130 mL) were added and stirred then brine was added (3.6 L). Layers were allowed to separate yielding three layers. The lower two layers showed no product so they were discarded. The tert-butyl methyl ether layer was washed with a mixture of 1 N sodium hydroxide (100 mL), deionized water (2 L), and brine (2 L). The organic layer was dried with sodium sulfate, filtered and evaporated to give 802 g of viscous residue. Toluene (1.4 L) was added to the residue and the mixture was heated to 80° C. to obtain a solution. Heptane (6 L) was added, the solution was heated to 93° C., and then cooled over 1.5hours to 0–10° C. with an ice bath. The mixture was filtered and the cake was rinsed with 60:40 heptane/toluene (2 L). The solid was dried in a vacuum oven to yield 670 g of subtitled product. The solids were recrystallized from toluene (2 L) and heptane (5.5 L) to yield 627 g (87% yield) of product as a white solid.

mp 119.5–21° C. $^1$H NMR ($CDCl_3$, 300 MHz) δ 1.48 (s, 18H), 2.8 (t, J=6.0 Hz, 2H), 3.97 (t, J=6.0 Hz, 2H), 5.52 (s, 1H), 7.42 (s, 1H), 7.82 (s, 2H).

D. Preparation of 2-(3,5-di-t-Butyl-4-hydroxyphenyl)-4-(2-10 (4-formylphenyloxy)ethyl)oxazole The compound of step C (204.3 g, 644 mmol), triethylamine (100 mL, 716 mmol) and methylene chloride (1.7 L) were stirred to give a solution. Methanesulfonyl chloride (81.3 g, 710 mmol) was added over 15 minutes and a water bath was used to keep the pot temperature below 31° C. The reaction mixture was stirred and allowed to cool to 23° C. over 1.5 hours. The reaction mixture was poured into a 4 L separatory funnel and the flask was rinsed with methylene chloride (0.5 L). The organic layer was washed with 1 N hydrochloric acid (3×1 L) and the combined aqueous layers were back-extracted with methylene chloride (0.3 L). The combined organic layers and washed with a solution of brine (0.5 L) and deionized water (0.5 L). The organic layers were dried with sodium sulfate, filtered and evaporated to give 254 g of the mesylate as an oily foam. To the intermediate mesylate compound was added dimethyl sulfoxide (DMSO, 0.7 L) and a solution was obtained. In a separate flask, 4-hydroxybenzaldehyde (89.6 g, 734 mmol), potassium t-butoxide (79.98 g, 0.713 mmol) and dimethylsulfoxide (1.2 L) were combined and heated to 45° C. to yield a brown solution. The mesylate compound in dimethylsulfoxide was added all at once. The reaction mixture was heated at 60–65° C. for 15 hours An additional 0.5 L of dimethyl sulfoxide was added. The reaction temperature was increased to 70° C. and held there for 2 hours. Then, 4-hydroxybenzaldehyde (3.92 g) and potassium t-butoxide (3.59 g) were added to the reaction mixture. After 7 hours at 70° C. the reaction mixture was allowed to cool to ambient temperature. Tert-butyl methyl ether (3.3 L) was added to the reaction mixture. The solution was extracted with 1 N sodium hydroxide (4×2L). The aqueous layers were combined, back extracted with tert-butyl methyl ether (2×1 L) and then discarded. The combined organic layers were washed with deionized water (2 L), deionized water/brine (2 L), and brine (2 L). The organic layer was dried with sodium sulfate, filtered and evaporated to give a dark residue (267.3 g). The residue was. dissolved in a mixture of methylene chloride (150 mL) and heptane (100 mL) and passed through a chromatography unit with a silica gel (2.5 kg) column. The column was eluted with 1:1 heptane/methylene chloride (16 L), methylene chloride (12 L), and 6% ethyl acetate/methylene chloride. Fractions containing the product as the major component were combined and evaporated to give 196 g of an amber oil. The oil was dissolved in chloroform (200 mL), and transferred to a flask with a mechanical stirrer. The flask was rinsed with hexanes/chloroform (100 L/25 mL) and hexanes (100 mL) and the washes were added to the solution. After adding hexanes (1.8 L), the solution was heated to reflux and 100 mL of distillate was collected. The mixture was cooled to 35° C. over 1.5 hours and then crystallization occurred. Using an ice/water bath, the solution was cooled to 6° C. over 1.5 hours. The product was filtered, rinsed with 10% chloroform/hexanes (300 mL), and dried in a vacuum oven to obtain 153 g (56% yield) of subtitled product as a white solid.

mp 110–112° C. HPLC assay showed 99.4% (by area) desired compound. $^1$H NMR ($CDCl_3$, 300 MHz) δ 1.45 (s, 18H), 3.10 (t, 2H, J=6 Hz), 4.38 (t, 2H, J=6 Hz), 5.50 (s, 1H), 7.02 (d, J=7 Hz, 2H), 7.50 (s, 1H), 7.79 (d, J=7 Hz, 2H), 7.82 (s, 2H), 9.85 (s, 1H).

E. Preparation of 2-(3,5-di-t-Butyl-4-hydroxyphenyl)-4-(2-(4-ethylaminomethylphencxy)ethyl)oxazole Hydrochloride Hemihydrate To 5.05 g (12 mmole) of the compound of step D dissolved in 50 ml. of dry methanol under nitrogen was added 7.85 ml (120 mmole) of moncethylamine. The solution was stirred for minutes then 6.8 ml (120 mmole) of acetic acid was added and the mixture was stirred under nitrogen for 30 minutes. Sodium cyanoborohydride, 795 mg (12.6 mmole) was added and the reaction was stirred for 3 hours. An additional 500 mg of sodium cyancborohydride was added and again stirred for an additional hour. Ethyl acetate was then added and the mixture was washed with water, saturated sodium bicarbonate and again with water. The organic layer was dried, filtered then evaporated to give 5.44 g of crude product which was chromatographed on 300 ml. silica, eluting with methylene chloride/methanol/concentrated ammonia (90:10:1). Fractions containing the desired product were concentrated under vacuum then dissolved in diethyl ether. Hydrogen chloride gas was bubbled through the solution to provide an oil which was dissolved in acetone and stripped to dryness to give 3.4 g (54%) of title product as a white foam.

FDMS-$M^+$450; Elemental analysis for ($C_{28}H_{38}N_2O_3$.HCl0.5$H_2O$); Calculated: C, 67.79; H, 8.13; N, 5.65. Found: C, 67.97; H, 7.99; N, 5.74. NMR ($CDCl_3$), δ 1.40 (t, 3H, J=7 Hz), 1.49 (s, 18H), 2.92 (q, 2H, J=4 Hz), 3.30 (t, 2H, J=7 Hz), 3.95 (t, 2H, J=7 Hz), 4.31 (t, 2H, J=7 Hz), 6.10 (bs, 1H), 6.85 (d, 2H, J=9 Hz), 7.49 (d, 2H, J=9 Hz), 7.87 (s, 1H), 8.21 (s, 2H), 9.59 (bs, 2H).

EXAMPLE 2

2-(3,5-di-t-Butyl-4-hydroxyphenyl)-4-(2-(4-dimethylaminomethyl-phenoxy)ethyl)oxazole Hydrochloride Title compound was prepared from 1.26 g (3 mmole) of the compound of Example 1D substantially in accordance with the procedure in Example 1E above using 200 mg (3.15 mmole) of sodium cyanoborohydride and 3.37 ml (30 mmole) of 40% aqueous dimethylamine. Such reaction provided 1.31 g (90%) of the title product as a white foam.

FDMS-$M^+$450; Elemental analysis for ($C_{28}H_{38}N_2O_3$.HCl); Calculated: C, 69.05; H, 8.07; N, 5.75; Found: C, 68.75; H, 7.94; H, 5.56; NMR ($CDCl_3$), δ 1.49 (s, 18H), 2.71 (d, 2H, J=3 Hz), 3.38 (t, 2H, J=7 Hz), 4.10 (d, 2H, J=7 Hz), 4.44 (t, 2H, J=7 Hz), 6.08 (s, 1H), 6.95 (d, 2H, J=9 Hz), 7.50 (d, 2H, J=9 Hz), 7.74 (s, 1H), 8.23 (s, 2H).

EXAMPLE 3

2-(3,5-di-t-Butyl-4-hydroxyphenyl)-4-(2-(4-methylethylaminomethylphenoxy)ethyl)oxazole Hydrochloride Hydrate Title compound was prepared from 3.36 g (7.98 mmole)of the compound of Example 1D substantially in accordance with the procedure in Example 1E above using 0.5 g (7.98 mmole) of sodium cyanoborohydride and 6.9 ml (79.8 mmole) of methylethylamine. The organic layer was chromatographed on silica gel using a methylene chloride/methanol gradient to give the free base (2.79 g, 75%). The free base was dissolved in methylene chloride, treated with hydrogen chloride gas and evaporated to give 2.8 g (93%) of the title product.

$^1$H NMR ($CDCl_3$) δ 8.0 (s, 2H), 7.6 (s, 1H), 7.5 (d, J=9 Hz, 2H), 6.95 (d, J=9 Hz, 2H), 5.7 (s, 1H), 4.35 (t, J=7 Hz, 2H), 4.1 (m, 2H), 3.2 (m, 3H), 2.9 (m, 1H), 2.6 (d, J=4 Hz, 3H), 1.5 (s, 18H), 1.45 (t, J=7 Hz, 3H); FDMS 464 ($M^+$-HCl); Elemental analysis for $C_{29}H_{41}ClN_2O_3.H_2O$ Calculated: C, 67.10; H, 8.35; N, 5.40. Found: C, 66.99; H, 7.96; N, 5.29.

EXAMPLE 4

2-(3,5-di-t-Butyl-4-hydroxyphenyl)-4-(2-(3-dimethylaminomethyl-phenoxy)ethyl)oxazole Hydrochloride A. Preparation of 2-(3,5-di-t-Butyl-4-hydroxyphenyl)-4-(2-(3-formylphenoxy)ethyl)oxazole To 4.44 g (14 mmole) of the compound of Example 1C dissolved in tetrahydrofuran (THF) were added 1.94 g (16 mmole) of 3-hydroxybenzaldehyde and 4.18 g (16 mmole) of triphenylphosphine ($PPh_3$) under nitrogen. The solution was chilled to −50° and a solution of 2.51 ml (16 mmole) of diethyldiazodicarboxylate (DEAD) in 15 ml of tetrahydrofuran was added over 10 minutes with stirring. The bath was removed and the reaction stirred under nitrogen for 4 hours. Hydrogen peroxide (0.89 ml 30%) was added and the reaction was stirred for 15 minutes, stripped, dissolved in 40 ml of methylene chloride and placed in the freezer. The diethoxycarbonylhydrazine was then filtered off and the filtrate was chromatographed, eluting with a 5 to 20% acetone/hexane gradient over 30 minutes. The appropriate fractions were bulked and stripped to give 3.2 g (54%) of subtitled product.

NMR ($CDCl_3$), δ 1.49 (s, 18H), 3.10 (t, 2H, J=7 Hz), 4.35 (t, 2H, J=7 Hz), 5.50 (s, 1H), 7.20 (m, 1H), 7.44 (m, 3H), 7.51 (s, 1H), 7.84 (s, 2H), 9.97 (s, 1H)

B. Preparation of 2-(3,5-di-t-Butyl-4-hydroxyphenyl)-4-(2-(3-dimethylaminomethylphenoxy)ethyl)oxazole Hydrochloride Title compound was prepared from 3.2 g (7.6 mmole) of the compound of step A substantially in accordance with the procedure in Example 1E using 503 mg (8.0 mmole) of sodium cyanoborohydride and 9.5 ml (76 mmole) of 40% dimethylamine. Such reaction provided 1.82 g white foam (49%) which was triturated with methylene chloride/isopropyl ether to give 1.25 g of title product.

FDMS-$M^+$450; Elemental Analysis for ($C_{28}H_{38}N_2O_3$.HCl); Calculated: C, 69.05; H, 8.07; N, 5.75. Found: C, 69.31; H, 8.13; N, 5.84. NMR ($CDCl_3$), δ 1.50 (s, 18H), 2.77 (d, 2H, J=5 Hz), 3.33 (t, 2H, J=7 Hz), 4.15 (d, 2H, J=4 Hz), 4.48 (t, 2H, J=7 Hz), 5.95 (s, 1H), 6.98 (dd, 1H, J=2 Hz, 9 Hz), 7.12 (d, 1H, J=9 Hz), 7.32 (t, 1H, J=9 Hz), 7.53 (d, 1H, J=2 Hz), 7.88 (s, 1H), 8.16 (s, 2H).

EXAMPLE 5

2-(3,5-di-t-Butyl-4-hydroxyphenyl)-4-(2-(4-n-propylaminomethyl-phenoxy)ethyl)oxazole Hydrochloride Title compound was prepared from 3.0 g (7.13 mmole) of the compound of Example 1D substantially in accordance with the procedure in Example 1E using 471 mg of sodium cyanoborohydride and 5.82 ml (71.3 mmole) of monopropylamine. Such reaction provided 1.67 g of the title product as a white foam (47%).

FDMS-$M^+$464; Elemental analysis for ($C_{28}H_{38}N_2O_3$.HCl); Calculated: C, 69.51; H, 8.25; N, 5.59. Found: C, 69.80; H, 8.24; N, 5.46. NMR ($CDCl_3$), δ 0.92 (t, 3H, J=7 Hz), 1.49 (s, 18H), 1.86 (m, 2H, J=7 Hz), 2.71 (m, 2H, J=7 Hz), 3.28 (t, 2H, J=7 Hz), 3.94 (t, 2H, J=7 Hz), 4.30 (t, 2H, J=7 Hz), 6.00 (s, 1H), 6.87 (d, 2H, J=9 Hz), 7.50 (d, 2H, J=9 Hz), 7.74 (s, 1H), 8.17 (s, 2H), 9.70 (bs, 2H).

EXAMPLE 6

2-(3,5-di-t-Butyl-4-hydroxyphenyl)-4-(2-(4-n-hexylamincmethyl-phenoxy)ethyl)oxazole Hydrochloride The title compound was prepared substantially as described in Example 1E, except using N-hexylamine. The reaction was concentrated in vacuo then treated with 1:1 ethyl acetate:water (100 ml). Phases were separated, and the organics were washed with aqueous saturated sodium bicarbonate (50 ml) followed by a brine wash (50 ml). Organics were concentrated in vacuo then treated with diethyl ether and silica gel (10 g) and the resultant material was concentrated in vacuo to a flowable powder. The powder was subjected to silica gel flash chromatography eluting with methylene chloride (3×200 ml), methylene chloride:1% methanol (5×100 ml), 94:5:1 methylene chloride:methanol:ammonium hydroxide (10×100 ml), 89:10:1 methylene chloride:methanol:ammonium hydroxide (4×250 ml). Fractions containing desired product were combined and concentrated in vacuo to afford 2.37 g of an oil. The oil was treated with chloroform (75 ml) then hydrochloric acid gas. The resultant solution was concentrated in vacuo to afford a foam which was treated with hot methylene chloride (10 ml) then diisopropyl ether (10 ml) and concentrated until turbidity was observed. The turbid solution was placed in freezer for approximately 2.5 hours. Insolubles were collected by filtration, washed with diisopropyl ether and dried in a vacuum oven at 40° C. overnight to afford 1.46 g of the title compound.

Mass Spectrum(FDMS): m/z 506 (M). $^1$H NMR ($CdCl_3$): δ 8.23 (s, 2H), 7.80 (s, 1H), 7.49 (d, J=8.3 Hz, 2H), 6.87 (d, J=8.3 Hz, 2H), 6.07 (s, 1H), 4.32 (m, 2H), 3.93 (m, 2H), 3.32 (m, 2H), 2.75 (m, 2H), 1.85 (m, 2H), 1.50 (m, 18H), 1.24 (m, 6H), 0.82 (t, J=6.6 Hz, 3H). Elemental analysis for $C_{32}H_{47}ClN_2O_3$: Calculated: C, 70.76; H, 8.72; N, 5.16. Found: C, 70.68; H, 8.61; N, 5.16.

EXAMPLE 7

2-(3,5-di-t-Butyl-4-hydroxyphenyl)-4-(2-(4-diethylaminomethyl-phenoxy)ethyl)oxazole Hydrochloride Dihydrate Title compound was prepared from 4.21 g (10 mmole) of the compound of Example 1D substantially in accordance with the procedure in Example 1E using 0.63 g (10 mmol) of sodium cyanoborohydride and diethylamine (10.3 ml, 100 mmole). The reaction was allowed to continue for 21 hours. The organic layer was chromatographed on silica gel using a methylene chloride/methanol gradient to give the free base which was then dissolved in methylene chloride, treated with hydrogen chloride gas and evaporated to provide 2.68 g (52%) of the title product.

1H NMR ($CDCl_3$) δ 8.05 (S, 2H), 7.6 (S, 1H), 7.55 (d, J=9 Hz, 2H), 6.95 (d, J=9 Hz, 2H), 5.8 (s, 1H), 4.4 (t, J=7 Hz, 2H), 4.1 (d, J=5 Hz, 2H), 3.25 (t, J=7 Hz, 2H), 3.0 (m, 4H), 1.5 (s, 18H), 1.4 (t, J=7 Hz, 6H); FDMS 478 ($M^+$-HCl); Elemental analysis for $C_{30}H_{43}ClN_2O_3.2H_2O$:

Calculated C, 64.32; H, 8.64; N, 5.00.

Found: C, 63.94; H, 8.46; N, 4.80.

EXAMPLE 8

2-(3,5-di-t-Butyl-4-hydroxyphenyl)-4-(2-(4-N-n-propyl-N-methylaminomethylphenoxy)ethyl)oxazole Hydrochloride The title compound was prepared substantially as described in Example 1E, except using N-methyl-N-n-propylamine and chromatographing with 0 to 10% (methanol:1% ammonium hydroxide): chloroform gradient over a thirty-minute period. Fractions containing the desired product were concentrated in vacuo , treated with chloroform (100 ml) and magnesium sulfate, filtered and the filtrate was saturated with hydrogen chloride gas. The solution was concentrated in vacuo to a foam affording 3.40 g (68%) of the title compound.

Mass Spectrum(FDMS): m/z 478 (M); $^1$H NMR ($DMSOd_6$): δ 8.31 (s, 1H), 7.91 (s, 1H), 7.72 (s, 2H), 7.51 (s, 1H), 7.16 (d J=8.4 Hz, 2H), 6.89 (d, J=8.4 Hz, 2H), 4.22 (t, J=6.4 Hz, 2H), 3.35 (s, 2H), 2.96 (t, J=6.4 Hz, 2H), 2.23 (t, J=7.3 Hz, 2H), 2.05 (s, 3H), 1.41 (m, 20H), 0.83 (t, J=7.3 Hz, 3H). Elemental analysis for $C_{30}H_{43}ClN_2O_3.H_2O$: Calculated: C, 67.58; H, 8.51; N, 5.25. Found: C, 67.65; H, 8.34; N, 5.33.

EXAMPLE 9

2-(3,5-di-t-Butyl-4-hydroxyphenyl)-4-(2-(4-N-n-propyl-N-ethylaminomethylphenoxy)ethyl)oxazole Hydrochloride A solution of N-ethyl-N-propylamine (29.5 mmole, 2.58 g) in chloroform (10 ml) was saturated with hydrogen chloride gas. This solution was concentrated in vacuo then treated with ethanol (11 ml), triethylamine (29.5 mmole, 2.99 g), titanium IV isopropoxide (29.5 mmole, 8.40 g) and 2-(3,5-di-t-butyl-4-hydroxyphenyl)-4-(2-(4-formylphenoxy)ethyl)oxazole (14.8 mmole, 6.22 g), prepared as described in Example 1D above. The suspension was stirred at room temperature for 4 hours then carefully treated with sodium borohydride (22.2 mmole, 0.84 g) to avoid frothing. Reaction was stirred approximately 3 days before being treated with 2N ammonium hydroxide (23 ml). To this mixture was added methylene chloride (150 ml) and diatomaceous earth (20 g) and the mixture was filtered through a pad of diatomaceous earth and washed with methylene chloride (100 ml). The filtrate was washed with brine (1×50 ml) and the organic layer was concentrated in vacuo to an oil, treated with chloroform and subjected to preparatory chromatography. The material was eluted with 0 to 10% (1% ammonium hydroxide:methanol) chloroform gradient over a thirty-minute period. Fractions containing the desired product were concentrated in vacuo to an oil. The oil was treated with chloroform and saturated with hydrogen chloride gas. This solution was concentrated in vacuo to afford 4.78 g (61%) of the title compound.

Mass Spectrum(FDMS): m/z 492 (M-HCl). 1H NMR ($DMSOd_6$): δ 10.45 (s, 1H), 7.94 (s, 1H), 7.73 (s, 2H), 7.53 (d, J=8.7 Hz, 2H), 7.03 (d, J=8.7 Hz, 2H), 4.28 (t J=6.5 Hz, 2H), 4.20 (t, J=5.2 Hz, 2H), 2.99 (m, 4H), 2.86 (m, 2H), 1.69 (m, 2H), 1.42 (s, 18H), 1.24 (t, J=7.2 Hz, 3H), 0.86 (t, J=7.3 Hz, 3H). Elemental analysis for $C_{31}H_{45}ClN_2O_3$: Calculated: C, 70.36; H, 8.57; N, 5.29. Found: C, 70.08; H, 8.32; N, 5.30.

EXAMPLE 10

2-(3,5-di-t-Butyl-4-hydroxyphenyl)-4-(2-(2,4-bis(methylethylaminomethyl)phenoxy)ethyl)oxazole Dihydrochloride A. Preparation of 2-(3,5-di-t-Butyl-4-hydroxyphenyl)-4-(2-(2,4-bis-formylphenoxy)ethyl)oxazole In a flask, 4.75 g (15 mmole) of the compound of Example 1 C, 2.36 g (15.75 mmole) of 3-formyl-4-hydroxybenzaldehyde, and 3.93 g (15 mmole) of triphenylphosphine were dissolved in 45 ml tetrahydrofuran with stirring, under nitrogen. The solution was chilled to −10° and a solution of 2.36 ml (15 mmole) diethyl azodicarboxylate in 15 ml. Tetrahydrofuran was added over 10 minutes, with stirring. The reaction exothermed to +1C. The bath was removed and the reaction stirred under nitrogen for 18 hours. The reaction was then stripped, dissolved in a minimum amount of methylene chloride and placed in the freezer. The diethoxycarbonylhydrazine was then, filtered off and the filtrate was chromatographed, Prep 500, two columns, eluting with 0 to 20% ethyl acetate/toluene gradient over 30 minutes. The appropriate fractions were bulked and stripped to give 3.3 g (49%) product which was used without further purification.

NMR ($CDCl_3$), δ 1.48 (s, 18H), 3.17 (t, 2H, J=7 Hz), 4.53 (t, 2H, J=5 Hz), 5.52 (s, 1H), 7.19 (d, 1H, 9 Hz), 7.53 (s, 1H), 7.84 (s, 2H), 8.11 (dd, 1H, J=2 Hz,9 Hz), 8.32 (d, 1H, J=2 Hz), 9.94 (s, 1H), 10.48 (s, 1H).

B. Preparation of 2-(3,5-di-t-Butyl-4-hydroxyphenyl)-4-(2-(2,4-bis(methylethylaminomethyl)phenoxy)ethyl)oxazole Dihydrochloride Hydrate Title compound hydrochloride was prepared from 1.5 g (3.34 mmole) of the product of Step A substantially in accordance with the procedure in Example 9 using 4.0 ml (13.4 mmol) titanium IV isopropoxide and 1.15 ml (13.4 mmole) of methylethylamine and 0.38 g (10 mmole) sodium borohydride. The organics were chromatographed on 100 ml silica, eluting with methylene chloride/methanol and concentrated ammonia (90:10:1). Appropriate fractions were concentrated and dissolved in methylene chloride/isopropyl ether. Hydrogen chloride gas was bubbled in and the resultant residue was triturated with isopropyl ether to give 1.10 g (54%) of title product as a white foam.

FDMS-$M^+$536; Elemental analysis for ($C_{33}H_{49}N_3O_3.2HCl.H_2O$); Calculated: C, 63.45; H, 8.52; N, 6.72. Found: C, 63.80; H, 8.53; N, 6.49. NMR ($CDCl_3$), δ 1.30–1.40 (m, 6H), 1.48 (S, 18H), 2.45–2.70 (m, 6H), 2.79–3.35 (m, 6H), 3.90–4.30 (m, 4H), 4.38 (t, 2H, J=5 Hz), 5.58 (s, 1H), 7.08 (d, 1H, J=9 Hz), 7.57 (s, 1H), 7.84 (s, 2H), 8.03 (d, 1H, J=9 Hz), 8.13 (s, 1H).

EXAMPLE 11

2-(3,5-di-t-Butyl-4-hydrocyphenyl)-4-(2-(4-(2-hydroxyethyl)ethylaminomethylphenoxy)ethyl) oxazole Hydrochloride To a stirred solution of N-ethylethanolamine (1.95 ml, 20 mmole) in ethanol (25 ml) was added titanium IV isopropoxide (5.9 ml, 20 mmole), then the compound of Example 1D (4.21 g, 10 mmole). The reaction was stirred for 4 hours, then sodium borchydride (0.57 g, 15 mmole) was added. After 20 hours at room temperature, the reaction was poured into 75 ml 2N ammonium hydroxide and diluted with methylene chloride. The mixture was filtered though diatomaceous earth and the filtrate was extracted with brine. The organic layer was dried over sodium sulfate, evaporated to dryness, and chromatographed on silica gel using a methylene chloride/methanol gradient to give the free base (3.56 g, 72%). The free base was dissolved in methylene chloride (86 ml), treated with hydrogen chloride gas, and evaporated to give desired product (3.92 g, 100%):

$^1$H NMR ($CDCl_3$) δ 8.0 (s, 2H), 7.6 (s, 1H), 7.5 (d, J=9 Hz, 2H), 6.95 (d, J=9 Hz, 2H), 5.7 (s, 1H), 4.35 (t, J=7 Hz, 2H), 4.2 (m, 2H), 3.9 (m, 2H), 3.2 (t, J=7 Hz, 2H), 3.15 (m, 4H), 1.5 (m, 21H); FD MS 494 ($M^+$-HCl); Elemental Analysis for $C_{30}H_{43}ClN_2O_4.0.5\ H_2O$: Calculated: C, 66.71; H, 8.21; N, 5.19. Found: C, 66.47; H, 8.10; N, 5.20.

EXAMPLE 12

2-(3,5-di-t-Butyl-4-methoxyphenyl)-4-(2-(4-N-bis (hydroxyethyllaminomethylphenoxy)ethyl)oxazole Hydrochloride The title compound was prepared substantially as described in Example 11 except using diethanolamine. The material was subjected to Preparatory chromatography, eluting with a gradient of 0 to 10% (1% ammonium hydroxide/methanol): chloroform over a thirty minute period. Fractions containing the title compound were combined and concentrated in vacuo to afford an oil. The oil was treated with chloroform then hydrogen chloride gas and concentrated in vacuo to afford 817 mg of the title compound as a foam.

Mass Spectrum (FDMS): m/z 510. (M-HCl). 1H NMR (CDC13): δ 7.96 (s, 2H), 7.58 (s, 1H), 7.48 (d, J=8.6 Hz, 2H), 6.97 (d,J=8.6, 2H), 5.68 (s, 1H), 4.35 (m, 4H), 4.01 (m, 4H), 3.33 (m, 4H), 3.17 (m,2H), 1.48 (s, 18H). Elemental analysis for $C_{30}H_{43}ClN_2O_5$+0.3 mole H2O: Calculated: C, 65.21; H, 7.95; N,5.07. Found: C, 65.18; H, 7.95; N, 4.67.

EXAMPLE 13

2-(3,5-di-t-Butyl-4-hydroxyphenyl)-4-(2-(4-[N-methyl-N-(3-piperidin-3-yl)propyl)aminomethyl] phenoxy)ethyl)oxazole Dihydrochloride A. Preparation of 2-(3,5-di-t-Butyl-4-hydroxyphenyl)-4-(2-(4-N-methyl-N-aminomethylphenoxy)ethyl)oxazole The subtitled compound was prepared substantially as described in Example 11, except using the methylamine hydrochloride salt. The crude material was subjected to preparatory chromatography. The material was eluted with 0 to 10% (1% ammonium hydroxide:methanol): chloroform gradient over a thirty minute period. Fractions containing desired product were reduced in vacuo, dried over sodium sulfate, filtered and concentrated in vacuo, to afford 6.74 g (62%) of the title compound.

Mass Spectrum(FDMS): m/z 436 (M). $^1$H NR($CdCl_3$): δ 7.83 (s, 2H), 7.46 (s, 1H), 7.42 (d, J=8.3 Hz, 2H), 6.92 (d J=8.3 Hz, 2H), 5.3 30 (bs, H), 4.22 (t J=6.5 Hz, 2H), 3.93 (s, 2H), 3.03 (t, J=6.5 Hz, 2H), 2.46 (s, 3H), 1.48 (s, 18H). Elemental analysis for $C_{27}H_{36}N_2O_3$: Calculated: C, 74.28; H, 8.31; N, 6.42. Found: C, 74.39; H, 8.51; N, 6.47.

B. Preparation of 2-((3,5-di-t-Butyl-4-hydroxyphenyl)-4-[N-methyl-N-(3-(N'-tert-butoxycarbonylpiperid-3-yl) propyl)amino methyl]phenoxy)ethyl)oxazole A red solution of the compound of Step A, (9.2 mmole, 4.01 g), in dimethylformamide (dimethylformamide,18 ml) was treated with 60% (wt/wt) sodium hydride (20.2 mmole, 808 mg). The suspension was stirred for 30 minutes at 24° C. then treated with a solution of N-tert-butoxycarbonyl-3-(3-bromopropyl)piperidine (8.4 mmole, 2.56 g) in dimethylformamide (5 ml). Next, the suspension was heated at 80° C. for 4 hours then cooled to 24° C. The reaction treated with 10% aqueous sodium bisulfate (25 ml), water (10 ml) and 3/2 ethyl acetate:hexane (50 ml). The phases were separated and the aqueous phase was extracted with 3:2 ethyl acetate:hexane (2×50 ml). Combined organics were washed with brine (2×50 ml), dried over sodium sulfate, filtered and concentrated in vacuo to afford 6.67 g of an oil. The crude material was subjected to preparatory chromatography. The material was eluted with 0 to 10% (1% ammonium hydroxide:methanol): chloroform gradient over a thirty-minute period. Fractions containing the desired product were reduced in vacuo, dried over sodium sulfate, filtered and concentrated in vacuo, to afford 4.19 g of the title compound. This material contained some impurities and was taken on to the next step without further purification.

Mass Spectrum(FDMS): m/z 662 (M+1); $^1$H NMR ($CdCl_3$): δ 7.83 (s, 2H), 7.50 (s, 1H), 7.19 (d, J=8.4 Hz, 2H), 6.88 (d, J=8.4 Hz, 2H), 5.49 (S, 1H), 4.27 (t J=6.6 Hz, 2H), 3.91 (m, 1H), 3.40 (s, 2H), 3.07 (t, J=6.6 Hz, 2H), 2.72 (m, 1H), 2.32 (t, J=7.3 Hz, 2H), 2.15 (s, 3H), 1.80 (m, 1H), 1.37–1.69 (m, 26H), 1.22 (m, 2H).

C. Preparation of 2-(3,5-di-t-Butyl-4-hydroxyphenyl)-4-(2-(4-[N-methyl-N-(3-(N'-tert-butoxycarbonyl-piperid-3-yl)propyl)aminomethyl]phenoxy)ethyl)oxazole Hydrochloride A solution of the compound of Step B (3.15 mmole, 2.09 g) in diethyl ether (20 ml) was treated with hydrogen chloride gas for approximately 10 minutes. The resulting heavy suspension was stirred an additional 20 minutes, filtered and washed with diethyl ether (20 ml) to afford 2.01 g (91%) of the subtitled compound.

Mass Spectrum(FDMS): m/z 661 (M). $^1H$ NMR ($CdCl_3$): δ 8.13 (s, 2H), 7.66 (s, 1H), 7.50 (d, J=8.5 Hz, 2H), 6.96 (d, J=8.5 Hz, 2H), 5.91 (s, 1H), 4.41 (t J=5.9 Hz, 2H), 4.10 (m, 2H), 3.84 (s, 2H), 3.30 (t, J=5.8 Hz, 2H), 2.96 (m, 1H), 2.78 (m, 2H), 2.63 (m, 3H), 2.49 (dd, J=9.9, 12.9 Hz, 1H), 1.85 (m, 2H), 1.50 (s, 27H). Elemental analysis for $C_{40}H_{60}ClN_3O_5$: Calculated: C, 68.89; H. 8.53; N, 6.03. Found: C, 68.65; H, 8.45; N, 6.02.

D. Preparation of 2-(3,5-di-t-Butyl-4-hydroxyphenyl)-4-(2-(4-[N-methyl-N-(3-(piperidin-3-yl)propyl)aminomethyl]phenoxy)ethyl)oxazole Dihydrochloride To a solution of the compound of Step C (3.0 mmole, 2.01 g) in chloroform (20 ml) was added thiophenol (6.07 mmole, 0.67 g). Next, hydrogen chloride gas was passed through this solution for approximately 30 minutes then stirred overnight at 24° C. before being concentrated in vacuo to a foam. The material was taken up into hot methylene chloride (10 ml) then tetrehydrofuran (15 ml) was added while heating the solution. The solution was boiled down to approximately 12 ml total volume, cooled to approximately −22° C. before tetrahydrofuran (10 ml) was added, resulting in the formation of a precipitate. The suspension was filtered, the insolubles were transferred with methylene chloride and the volume was reduced to approximately 5 ml. Tetrahydrofuran (20 ml) was added and the solution was boiled down to approximately 5 ml. Next, diethyl ether (20 ml) was added to the hot solution resulting in the formation of a gum. The suspension was cooled to 24° C., the gum was triturated and insolubles were collected by filtration and washed with diethyl ether (20 ml). Insolubles were resuspended with stirring in hot diethyl ether (150 ml). After heating for approximately 30 minutes (keeping volume between 100–150 ml) the insolubles were collected by filtration and washed with hot diethyl ether (100 ml). Insolubles were dried in a vacuum oven at 60° C. overnight to afford 1.32 g (72%) of the title compound.

Mass Spectrum(FDMS): m/z 562 (M+1). $^1H$ NMR ($CdCl_3$): δ 8.00(s, 2H), 7.62 (s, 1H), 7.50 (d, J=8.1 Hz, 2H), 6.95 (d, J=8.1 Hz, 2H), 5.74 (s, 1H), 4.35 (m, 2H), 4.26 (m, 2H), 3.59 (m, 1H), 3.37 (m, 1H), 3.20 (m, 2H), 3.04 (m, 1H), 2.66–2.89 (m, 4H), 2.55 (m, 1H), 1.80–2.25 (m, 7H), 1.49 (s, 18H), 1.11–1.41 (m, 3H). Elemental analysis for $C_{35}H_{53}Cl_2N_3O_3$: Calculated C, 66.23; H, 8.42; N, 6.62. Found: C, 66.47; H, 8.67; N, 6.39.

EXAMPLE 14

2-(3,5-di-t-Butyl-4-hydroxyphenyl)-4-(2-(4-N-methyl-N-ethylaminoethylphenoxy)ethyl)oxazole Hydrochloride Heptahydrate A. Preparation of M-formyl-N-ethyl-p-hydroxyphenethylamine To a suspension of 1,1'-carbonyldiimidazole (326 mmole, 52.81 g) in tetrahydrofuran (164 ml) cooled to 0° C., was added dropwise 96% formic acid (326 mmole, 14.99 g) over a 26 minute period. Reaction stirred at 0° C. for 30 minutes then a light suspension of N-ethyl-p-hydroxyphenethylamine (102 mmole, 16.88 g) in tetrahydrofuran (66 ml) was added over a 10 minute period. Reaction then stirred at 22° C. for 170 minutes before being treated with methanol (10 ml). After stirring for 90 minutes, reaction was concentrated in vacuo to an oil containing crystals. The mixture was taken up into methylene chloride and subjected to preparatory chromatography eluting with a gradient of 0 to 5% methanol methylene chloride over a thirty-minute period. The fractions containing the title compound were combined, concentrated in vacuo to afford 13.46 g of an oil that slowly crystallizes out. Fractions containing title compound and impurities were resubjected to preparatory column chromatography under the same conditions described above to afford an additional 2.61 g of the title compound.

mp (° C.): 85 Mass Spectrum (FDMS): m/z 193. (M). $^1H$ NMR ($DMSOd_6$): δ 9.20 (s, 1H), 8.01 (s, 1/2H), 7.72 (s, 1/2H), 7.00 (d, J=8.4 Hz, 1H), 6.99 (d, J=8.4 Hz, 1H), 6.66 (d, J=8.4 Hz, 2H), 3.34 (dt, J=7.2 Hz, 2H), 3.21 (dq, J=7.1 Hz, 2H), 2.64 (dt, J=7.2 Hz, 2H), 1.04 (dt, J=7.1 Hz, 2H). Elemental analysis for $C_{11}H_{15}NO_2$: Calculated: C, 68.37; H, 7.82; N, 7.25. Found: C, 68.56; H, 7.81; N, 7.49.

B. Preparation of 2-(3,5-di-t-Butyl-4-hydroxyphenyl)-4-(2-(4-N-formyl-N-ethylaminoethylphenoxy)ethyl)oxazole The title compound was prepared substantially as described in Example 4 above except using N-formyl-N-ethyl-p-hydroxyphenethylamine and 0.7M (mmole alcohol/ml tetrahydrofuran) reaction solution. After stirring at 24° C. for approximately 22 hours, the reaction was concentrated in. vacuo. The filtrate was concentrated in vacuo to an oil, treated with ethyl acetate and subjected to preparatory chromatography. The material was eluted with 45% ethyl acetate. Fractions containing desired product were concentrated in vacuo then resubjected to preparatory chromatography. The material was eluted with 0 to 20% ethyl acetate/(93% chloroform:hexane) gradient over a thirty minute period. Fractions containing the desired product were concentrated in vacuo then resubjected to preparatory chromatography. The material was eluted with 5 to 30% acetone/hexane gradient over a thirty minute period. Fractions containing desired product were concentrated in vacuo to afford 3.01 g (19%) of the subtitled compound as a foam.

Mass Spectrum(FDMS): m/z 493 (M+1). $^1H$ NMR ($DMSOd_6$): δ 8.01 (s, 1/2H), 7.91 (s, 1/2H), 7.74 (s, H), 7.72 (s, 2H), 7.52 (bs, 1H), 7.13 (d, J=8.4 Hz, 2H), 6.88 (d, J=8.4 Hz, 2H), 4.20 (t, J=6.5 Hz, 2H), 3.40 (dt, J=7.1 Hz, 2H), 3.22 (dq, J=7.1 Hz, 2H), 2.96 (t, J=6.5 Hz, 2H), 2.71 (dt, J=7.1 Hz, 2H), 1.41 (s, 18H), 1.04 (dt, J=7.1 Hz, 3H). Elemental analysis for $C_{30}H_{40}N_2O_4$: Calculated: C, 73.14; H, 8.18; N, 5.69. Found: C, 73.30; H, 8.44; N, 5.90.

C. Preparation of 2-(3,5-di-t-Butyl-4-hydroxyphenyl)-4-(2-(4-N-methyl-N-ethylaminoethylphenoxy)ethyl)oxazole Sulfuric acid (6.0 mmole, 0.597 g) was carefully added dropwise over an eight minute period to a cooled suspension of lithium aluminum hydride (12.2 mmole, 0.462 g) in tetrahydrofuran (THF, 18 ml). After the addition was complete, the ice bath was removed. Approximately one hour after the addition, the reaction was cooled to 0° C., then a solution of the compound of Step B in tetrahydrofuran (4 ml) was added over a ten minute period. The reaction was stirred at 24° C. for 3 hours then quenched with water (12.2 mmole, 214 μL). Next, chloroform (200 ml) was added followed by 5N hydrochloric acid (50 ml). Phases were separated and the aqueous phase was extracted with chloroform (2×50 ml). Combined organic phases were washed with brine (1×50 ml) then dried over sodium chloride, filtered and concentrated in vacuo to afford 5.8 g of an oil that contained some solids. The material was treated with ethyl acetate (250 ml) then washed with saturated aqueous sodium bicarbonate (2×50 ml). The organics were dried over sodium sulfate, filtered then concentrated in vacuo to afford 2.77 g of an oil. The material was treated with chloroform and subjected to preparatory chromatography. The material was eluted with 0 to 10% (1% ammonium hydroxide methanol): chloroform gradient over a 30 minute period. Fractions containing the desired product were concentrated in vacuo to an oil. This material was taken up into chloroform then saturated with hydrogen chloride gas. The solution was concentrated in vacuo to afford 1.35 g (43%) of the title compound as a foam.

Mass Spectrum(FDMS): m/z 478 (M+1). $^1$H NMR ($DMSOd_6$): δ 7.92 (s, 1H), 7.72 (s, 2H), 7.54 (s, 1H), 7.21 (d, J=8.6 Hz, 2H), 6.93 (d, J=8.6 Hz, 2H), 4.22 (t, J=6.6 Hz, 2H), 3.19 (m, 4H), 2.98 (m, 4H), 2.76 (d, J=4.9 Hz, 3H), 1.41 (s, 18H), 1.22 (t, J=7.2 Hz, 3H). Elemental analysis for $C_{30}H_{40}N_2O_4$.$0.7H_2O$ Calculated: C, 68.28; H, 8.48; N, 5.31. Found: C, 68.20; H, 8.41; N, 5.35.

EXAMPLE 15

2-(3,5-di-t-Butyl-4-hydroxyphenyl)-4-(2-(4-N-ethyl-N-methylaminobutyl)phenoxyethyl)oxazole Hydrochloride A. Preparation of 4-(4-Hydroxyphenyl)butyl bromide A solution of triphenylphosphine (144.1 mmole, 37.80 g) in methylene chloride (556 ml) was treated with bromine (144.1 mmole, 23.03 g) until a pale yellow color persisted. After stirring approximately 15 minutes, a solution of 4-(4-hydroxyphenyl)butanol (96.1 mmole, 15.97 g) and imidazole (192.2 mmole, 13.08 g) in methylene chloride (355 ml) was added over a 15 minute period. Approximately 4 hours later, the reaction suspension was filtered and the filtrate was reduced in volume. To the reduced filtrate was added silica gel and the suspension was reduced to dryness. This material was filtered and the first six fractions were eluted with 10% ethyl acetate: hexane. Fractions 7 through 12 were eluted with 20% ethyl acetate: hexane. Fractions 7 through 10 were combined, reduced in volume, dried over sodium sulfate, filtered and concentrated in vacuo to afford 19.32 g (88%) of the title compound as an oil.

Mass Spectrum (FDMS): m/z 230. (M+1). 1H NMR (CDCl3): δ 7.03 (d, J=8.4 Hz, 2H), 6.75 (d, J=8.4 Hz, 2H), 4.59 (s, 1H),3.40 (t, J=6.7 Hz, 2H), 2.56 (m, 2H), 1.83–1.90 (m, 2H), 1.70–1.77 (m, 2H). Elemental analysis for $C_{10}H_{13}BrO$: Calculated: C,52.42; H, 5.72. Found: C, 52.24; H, 5.61.

B. Preparation of 2-(3,5-di-t-Butyl-4-hydroxyphenyl)-4-(2-(4-(4-bromobutyl)phenoxyethyl)oxazole The title compound was prepared substantially as described in Example 4 except using the compound of Step A. The reaction was concentrated in vacuo to an oil. The oil was treated with chloroform (25 ml), triturated, then treated with diatomaceous earth and filtered through a pad of diatomaceous earth. The filtrate was reduced in volume then subjected to preparatory chromatography. The material was eluted with a gradient of 20 to 35% diethyl ether: hexane over a 30 minute period. Fractions 4–15 were combined, concentrated in vacuo then rechromatographed eluting with a gradient of 20 to 35% diethyl ether: hexane over a 30 minute period. Fractions 8–16 were combined, concentrated in vacuo then rechromatographed eluting with a gradient of 5 to 20% ethyl acetate: (33% chloroform:67% hexane) over a 30 minute period. Fractions 7–9 were combined, dried over sodium sulfate, filtered and concentrated in vacuo to afford 10.51 g (49%) of the title compound.

Mass Spectrum (FDMS): m/z 529. (M+1). 1H NMR (CDCl3): δ 7.83 (s, 2H), 7.50 (s, 1H), 7.08 (d, J=8.5 Hz, 2H), 6.85 (d,J=8.5 Hz, 2H), 5.49 (s1 1H), 4.25 (t, J=6.6 Hz, 2H), 3.41 (t, J=6.6 Hz, 2H), 3.06(t, J=6.6 Hz, 2H), 2.58 (t, J=7.4 Hz, 2H), 1.88 (m, 2H), 1.72 (m, 2H), 1.49 (s,18H). Elemental analysis for $C_{29}H_{38}BrNO_3$: Calculated: C,65.90; H, 7.25; N, 2.65. Found: C,66.14; H, 7.26; N, 2.36.

C. Preparation of 2-(3,5-di-t-Butyl-4-hydroxyphenyl)-4-(2-(4-N-ethyl-N-methylaminobutyl)phenoxyethyl)oxazole Hydrochloride A solution of N-methylethyl amine (7.8 mmole, 0.46 g) in dimethylformamide (21 ml) was treated with sodium hydride (7.8 mmole, 0.68 g). The suspension was heated at 35° C. for 15 minutes. Next, the suspension was treated with a solution of a compound of Step B (8.5 mmole, 4.51 g) in dimethylformamide (21 ml). The suspension was then heated at 70° C. for approximately 4.5 hours before additional N-methylethyl amine (15.6 mmole, 0.92 g) was added. Forty five minutes later the reaction was cooled to 22° C., treated with ethyl acetate (50 ml), hexane (25 ml) and 10% aqueous sodium sulfate 950 ml). The phases were separated and the aqueous phase was extracted with 2:1 ethyl acetate: hexane (3×75 ml). Combined organics were washed with brine (2×100 ml), dried over sodium sulfate, filtered and concentrated in vacuo to afford 4.16 g of an oil. The oil was treated with chloroform, filtered through a pad of diatomaceous silica and washed with chloroform. The filtrate was subjected to preparatory silica gel chromatography. The material was eluted with a gradient of 0 to 10% (1% ammonium hydroxide methanol): chloroform over a thirty minute period. Fractions containing the desired product were combined, concentrated in vacuo, taken up into chloroform (100 ml),washed with 1:1 saturated aqueous sodium bicarbonate water (50 ml) then brine (50 ml). The organics were dried over sodium sulfate, filtered and concentrated in vacuo to afford 1.6 g of an oil. The oil was treated with chloroform (50 ml) then saturated with hydrogen chloride gas. This solution was concentrated in vacuo to a foam. The foam was treated with tetrahydrofuran (THF) and boiled on a steam bath while slowly adding diisopropyl ether. The tetrahydrofuran was boiled off, resulting in the product oiling out. The remaining solvent was decanted off and isopropyl ether (10 ml) was added. The biphasic solution was boiled on steam bath, solvent was decanted and the remaining material was pulled on house vacuum overnight to afford 1.38 g of the title compound as a foam.

Mass Spectrum (FDMS): m/z 506. (M). 1H NMR (CDCl3): δ 7.86 (s, 2H), 7.52 (s, 1H), 7.06 (d, J=8.5 Hz, 2H), 6.85 (d,J=8.5 Hz, 2H), 5.54 (s, 1H), 4.26 (t, J=6.5 Hz, 2H), 3.08 (t, J=6.5 Hz, 2H), 2.88(m, 3H), 2.67 (d, J=4.9 Hz, 3H), 2.60 (t, J=7.3 Hz, 2H), 1.66–1.85 (m, 3H),1.38–1.48 (m, 24H). Elemental analysis for $C_{32}H_{47}ClN_2O_3$: Calculated: C, 70.76; H, 8.72; N, 5.16. Found: C,70.52; H, 8.56; N, 5.41.

EXAMPLE 16

2-(3,5-di-t-Butyl-4-hydroxyphenyl)-4-(2-(3-N-ethyl-N-methylaminopropyl)phenoxy)ethyl)oxazole Hydrochloride A. Preparation of 2-(3,5-di-t-Butyl-4-hydroxyphenyl)-4-(2-(4-(2-cyanoethyl)phenoxyethyl)oxazole The title compound was prepared substantially as described in Example 4 except using 3-(4-hydroxyphenyl) propionitrile. The reaction was concentrated in vacuo to an oil. The oil was treated with chloroform (75 ml), triturated, and filtered. The filtrate was washed with saturated aqueous sodium bicarbonate (2×250 ml) and 10% sodium bisulfate (1×250 ml). The organic layer was dried over sodium sulfate, filtered and concentrated in vacuo to afford a dark oil. The oil was treated with methylene chloride and subjected to preparatory silica gel chromatography. Material was eluted with a gradient of 10 to 25% ethyl acetate: hexane over a thirty minute period. Fractions containing the title compound were combined and concentrated in vacuo to afford 29.57 g of an oil. This material was resubjected to preparatory silica gel chromatography eluting with a gradient of 15 to 35% diethyl ether: hexane over a thirty minute period. Fractions containing the title compound were combined and concentrated in vacuo to afford 20.57 g of foam. This material was resubjected to preparatory silica gel chromatography eluting with a gradient of 10 to 30% acetone: hexane over a thirty minute period. Fractions containing the title compound were combined and concentrated in vacuo to afford 14.71 g of foam. This material contained trace impurities and was taken on to the next step without further purification.

Mass Spectrum (FDMS): m/z 446. (M). 1H NMR (DMSOd6): δ 7.92 (s, 1H), 7.73 (s, 2H), 7.52 (s, 1H), 7.19 (d, J=8.6 Hz,2H), 6.91 (d, J=8.6 Hz, 2H), 4.23 (t, 2H), 2.96 (t, 2H), 2.78 (m, 4H), 1.42 (s,18H).

B. Preparation of 2-(3,5-di-t-Butyl-4-hydroxyphenyl)-4-(2-(4-(2-formylethyl)phenoxyethyl)oxazole To a cooled solution of the compound of Step A (32.9 mmol, 14.68 g) in toluene (105 ml) at −78° C., was added a 1.0 molar solution of diisobutylaluminum hydride (42.7 mmole, 42.7 ml) over a seventeen minute period. The reaction was then stirred at 22° C. for 1 hour and quenched with methanol (4.1 ml). The suspension was cooled to 0° C. and treated with a saturated solution of ammonium hydroxide (300 ml). After stirring for 1.5 hours, the reaction was treated with 50% sulfuric acid until a biphasic solution resulted. The mixture was then treated with ethyl acetate (250 ml) and the phases were separated. The aqueous phase was extracted with ethyl acetate (3×100 ml). The combined organic phases were washed with brine (2×200 ml), dried over sodium sulfate, filtered and concentrated in vacuo to an oil. The oil was subjected to preparatory silica gel chromatography. Material was eluted with a gradient of 0 to 10% methanol toluene over a thirty minute period. Fractions containing subtitled compound were combined, concentrated in vacuo to afford 11.76 g of an oil. This material was taken on to the next step without further purification.

Mass Spectrum (FDMS): m/z 449. (M). 1H NMR (DMSOd6): δ 9.70 (s, 1H), 7.91 (s, 1H), 7.73 (s, 2H), 7.53 (s, 1H), 7.12(d, J=8.6 Hz, 2H), 6.87 (d, J=8.6 Hz, 2H), 4.20 (t, J=6.5 Hz, 2H), 2.96 (t,J=6.5 Hz, 2H), 2.75 (m, 4H), 1.42 (s, 18H).

C. Preparation of 2-(3,5-di-t-Butyl-4-hydroxyphenyl)-4-(2-(3-N-ethyl-N-methylaminopropyl)phenoxy)ethyl)oxazole Hydrochloride The title compound was prepared substantially as described in Example 11 except using the compound of step B and N-methylethylamine. The material was subjected to preparatory chromatography eluting with a gradient of 0 to 5% (1% ammonium hydroxide: methanol): chloroform over a thirty minute period. Remaining fractions eluted with 5% (1% ammonium hydroxide: methanol): chloroform. Fractions containing desired product were combined, concentrated in vacuo, taken up into chloroform (100 ml) and washed with saturated sodium bicarbonate (10 ml) and water (15 ml) followed by water (25 ml). The organic layer was dried over sodium sulfate and filtered. The filtrate was saturated with hydrogen chloride gas and concentrated in vacuo to afford 1.61 g of the title compound as a foam.

Mass Spectrum (FDMS): m/z 492. (M-HCl). 1H NMR (CDCl3): δ 7.84 (s, 2H), 7.51 (s, 1H), 7.07 (d, J=8.6 Hz, 2H), 6.86 (d,J=8.6 Hz, 2H), 5.51 (s, 1H), 4.25 (t, J=6.6 Hz, 2H), 2.84–3.09 (m, 6H), 2.67 (mn,5H), 2.13–2.21 (m, 2H), 1.48 (s, 18H), 1.39 (t, J=7.3 Hz, 3H). Elemental analysis for $C_{31}H_{45}ClN_2O_3$+0.2 mole $H_2O$: Calculated: C, 69.89; H, 8.58; N,5.26. Found: C, 69.88; H, 8.73; N, 5.32.

EXAMPLE 17

2-(3, 5-di-t-Butyl-4-methoxyphenyl)-4-(2-(4-N-ethyl-N-methylaminomethylphenoxy)ethyl)oxazole Hydrochloride A. Preparation of 2-(3,5-di-t-Butyl-4-methoxyphenyl)-4-(2-(4-formylphenoxy)ethyl)oxazole A solution of the compound of Example 1D (8.4 mmole, 3.54 g) and methyl iodide (67.3 mmole, 9.54 g) in tetrahydrofuran (40 ml) and dimethylformamide (4 ml) was treated with sodium hydride (60% wt/wt, 16.8 mmole, 0.67 g). After stirring 31 hours at 22° C., the reaction was treated with water (10 ml) and the pH was adjusted from 12.6 to 5.4 with 1N hydrochloric acid. The biphasic solution was reduced in volume to remove tetrahydrofuran then ethyl acetate was added (100 ml) followed by 10% aqueous sodium bisulfate (50 ml). The phases were separated and the organic phase was dried over sodium sulfate and filtered. The filtrate was subjected to preparatory silica gel chromatography, eluting with a gradient of 20 to 45% ethyl acetate: hexane over a thirty minute period. Fractions containing subtitled compound were combined and concentrated in vacuo to afford 3.57 g of an oil. Material was taken on to next step without further purification.

Mass Spectrum (FDMS): m/z 435. (M). 1H NMR (CDCl3): δ 9.88 (s, 1H), 7.90 (s, 2H), 7.82 (d, J=8.8 Hz, 2H), 7.53 (s,1H), 7.02 (d, J=8.8 Hz, 2H), 4.36 (t, J=6.5 Hz, 2H), 3.70 (s, 3H), 3.11 (t,J=6.5 Hz, 2H), 1.46 (s, 18H).

B. Preparation of 2-(3,5-di-t-Butyl-4-methoxyphenyl)-4-(2-(4-N-ethyl-N-methylaminomethylphenoxy)ethyl)oxazole Hydrochloride The title compound was prepared substantially as described in Example 11 except using the compound of Step A. The material was subjected to preparatory chromatography eluting with a gradient of 0 to 10% (1% ammonium hydroxide methanol): chloroform over a thirty minute period. Fractions containing title compound were combined and concentrated in vacuo to a foam. The foam was treated with chloroform then saturated with hydrogen chloride gas. This solution was concentrated in vacuo to afford 2.2 g of the title compound as a foam.

Mass Spectrum (FDMS): m/z 478. (M-HCl) 1H NMR (DMSOD6): δ 10.46 (s, 1H), 8.00 (s, 1H), 7.83 (s, 2H), 7.51 (d, J=8.6 Hz,2H), 7.04 (dd, J=8.6, 2H), 4.09–4.31 (m, 4H), 3.68 (s, 3H), 2.92–3.11 (m, 4H),2.57 (d, J=4.8 Hz, 3H), 1.42 (s, 18H), 1.25 (t, J=7.2 Hz, 3H). Elemental analysis for $C_{30}H_{43}ClN_2O_3$+0.2 mole $H_2O$: Calculated: C, 69.46; H, 8.43; N,5.40. Found: C, 69.23; H, 8.47; N, 5.53.

EXAMPLE 18

2-(3,5-di-t-Butyl-4-hydroxyphenyl)-4-(2-(4-(4-dimethylaminobutyryl)phenyloxy)ethyl)oxazole Hydrochloride A. Preparation of 2-(3,5-di-t-Butyl-4-hydroxyphenyl)-4-(2-(4-(4-chlorobutyryl)phenyloxy)ethyl)oxazole To a stirred solution of the compound of Example 1C (5.68 g, 17.92 mmole) in tetrahydrofuran (54 ml) was added 4-chloro-4'-hydroxybutyrophenone (3.56 g, 17.92 mmole) and triphenylphosphine (5.16 g, 19.71 mmole). After cooling to −20° C., a solution of diethylazodicarboxylate (3.1 ml, 19.71 mmole) in tetrahydrofuran (12 ml) was added dropwise over 15 min. The reaction was allowed to warm to room temperature and stir for 5 hours, at which time it was diluted with diethyl ether and extracted with water and brine. The organic layer was dried over sodium sulfate, evaporated to dryness, and chromatographed on silica gel using a hexane-acetone gradient to give the intermediate chloroketone (4.77 g, 53%):

$^1H$ NMR ($CDCl_3$) δ 7.95 (d, J=9 Hz, 2H), 7.85 (s, 2H), 7.5 (s, 1H), 6.95 (d, J=9 Hz, 2H), 5.5 (s, 1H), 4.35 (t, J=7 Hz, 2H), 3.7 (t, J=6 Hz, 2H), 3.1 (m, 4H), 2.2 (m, 2H), 1.5 (s, 18H); FD MS 497 ($M^+$).

B. Preparation of 2-(3,5-di-t-Butyl-4-hydroxyphenyl)-4-(2-(4-(4-dimethylaminobutyryl)phenyloxy)ethyl)oxazole Hydrochloride To a stirred solution of the chloroketone (5.09 g, 10.2 mmole) in acetone (51 ml) was added sodium iodide (7.66 g, 51 mmole). The reaction was heated at 50° C. for 28 hours, evaporated to dryness, and redissolved in methylene chloride and water. The organic layer was extracted with brine, dried over sodium sulfate, and evaporated to dryness to give the intermediate iodoketone, which was used without further purification. The iodoketone was dissolved in toluene (30 ml), cooled to 0° C., and treated with anhydrous dimethylamine (0.79 ml, 12 mmole). The reaction was heated to 80° C. for 3 hours, then allowed to cool to room temperature. A white precipitate was filtered, and the filtrate was diluted with ethyl acetate and saturated sodium bicarbonate. The organic layer was extracted with O.!N sodium thiosulfate and brine, dried over sodium sulfate, evaporated to dryness, and chromatographed on silica gel using a methylene chloride/methanol gradient to give the free base (1.82 g, 35%). The free base was dissolved in methylene chloride (50 ml), treated with hydrogen chloride gas, and evaporated to give desired product (1.87 g, 96%):

$^1H$ NMR ($CDCl_3$) δ 8.0 (s, 2H), 7.95 (d, J=9 Hz, 2H), 7.6 (s, 1H), 6.95 (d, J=9 Hz, 2H), 5.8 (s, 1H), 4.4 (t, J=7 Hz, 2H), 3.3-3.1 (m, 6H), 2.8 (d, J=4 Hz, 6H), 2.25 (m, 2H), 1.5 (s, 18H); FDMS 506 ($M^+$−HCl); Elemental analysis for $C_{31}H_{43}ClN_2O_4$: Calculated: C, 68.55; H, 7.98; N, 5.16. Found: C, 68.36; H, 7.90; N, 5.34.

EXAMPLE 19

2-(3,5-di-t-Butyl-4-hydroxyphenyl)-4-(2-(4-(1-dimethylaminoethyl)phenyloxy)ethyl)oxazole Hydrochloride Monohydrate A. Preparation of 2-(3,5-di-t-Butyl-4-hydroxyphenyl)-4-(2-(4-acetylphenyloxy)ethyl)oxazole To a stirred solution of 10 g (31.5 mmole) of the compound of Example 1C above, in tetrahydrofuran (95 ml) was added 4-hydroxyacetophenone (4.29 g, 31.5 mmole) and triphenylphosphine (9.09 g, 34.7 mmole). After cooling to −20° C., a solution of diethylazodicarboxylate (5.5 ml, 34.7 mmole) in tetrahydrofuran (31 ml) was added dropwise over 15 min. The reaction was allowed to warm to room temperature and stir for 2.5 hours, at which time it was diluted with diethyl ether and extracted with water and brine. The organic layer was dried over sodium sulfate, evaporated to dryness, and chromatographed on silica gel using a toluene-ethyl acetate gradient to give the subtitled compound (8.5 g, 62%):

$^1H$ NMR ($CDCl_3$) δ 7.95 (d, J=9 Hz, 2H), 7.85 (s, 2H), 7.5 (s, 1H), 6.95 (d, J=9 Hz, 2H), 5.5 (s, 1H), 4.35 (t, J=7 Hz, 2H), 3.1 (t, J=7 Hz, 2H), 2.55 (s, 3H), 1.5 (s, 18H); FDMS 435 ($M^+$).

B. Preparation of 2-(3,5-di-t-Butyl-4-hydroxyphenyl)-4-(2-($^4$-(1-dimethylaminoethyl)phenyloxy)ethyl)oxazole Hydrochloride Title compound was prepared substantially in accordance with the procedure in Example 1E above using the compound of Step A, 1.23 g (19.5 mmole) of sodium cyanoborohydride and dimethylamine (19.4 ml, 293 mmole), heating to 60° C. for 24 hours. The organic layer was chromatographed on silica gel using a methylene chloride/methanol gradient to give the free base which was dissolved in methylene chloride, treated with hydrogen chloride gas, and evaporated to give 8.31 g (80%) of the title product.

$^1H$ NMR ($CDCl_3$) δ 11.6 (bs, 1H), 8.05 (s, 2H), 7.6 (s, 1H), 7.45 (d, J=9 Hz, 2H), 6.95 (d, J=9 Hz, 2H), 5.8 (s, 1H), 4.4 (t, J=7 Hz, 2H), 4.15 (m, 1H), 3.25 (t, J=7 Hz, 2H), 2.7 (d, J=4 Hz, 3H), 2.55 (d, J=4 Hz, 3H), 1.85 (d, J=7 Hz, 3H), 1.5 (s, 18H); FDMS 464 ($M^+$−HCl); Elemental analysis for $C_{29}H_{41}ClN_2O_3.H_2O$: Calculated: C, 67.10; H, 8.35; N, 5.40. Found: C, 67.00; H, 8.04; N, 5.24.

EXAMPLE 20

2-(3,5-di-t-Butyl-4-hydroxyphenyl)-4-(2-(4-N-methyl-N-ethylaminomethyl-3-methylphenoxy)ethyl)oxazole Hydrochloride Hydrate A. Preparation of 3-Methyl-allyloxybenzene m-Cresol 10.4 ml (100 mmol), 10.8 ml (125 mmole) allyl bromide, and 16.56 g (120 =mmole) of potassium carbonate were stirred in 50 ml of acetone and refluxed, with stirring, under nitrogen, for 18 hours. The reaction was cooled, the insoluble inorganics were filtered off and the filtrate was stripped to give 14.0 g (95%) of subtitled product, which was used without further purification.

NMR ($CDCl_3$), δ 2.33 (s, 3H), 4.51–4.54 (m, 2H), 5.26–5.45 (m, 2H), 6.00–6.13 (m, 1H), 6.72–6.78 (m, 2H), 7.17 (t, 1H, J=9 Hz).

B. Preparation of 4-Allyloxy-2-methylbenzaldehyde

N-methyl formanilide 19.4 ml (158 mmole), was chilled to 13° C., where it began to solidify. Phosphorus oxychloride, 13.7 ml (147 mmole), was added with stirring, under nitrogen. After 25 minutes, the temperature was 45° C. and the reaction had again begun to solidify. The compound of Step A, 14 g (95 mmole), was added and the mixture was stirred and heated in a 70° C. oil bath. The reaction exothermed to 95° C. Stirring was continued under nitrogen for 30 minutes. The bath was removed and when the temperature reached 35°, the mixture was dissolved in chloroform. Ice was added and the layers were separated and washed once with water, twice with saturated sodium bicarbonate, once again with water and once with brine. The organic layer was chromatographed on 450 ml silica, eluting with chloroform to give 13.54 g (81%) of subtitled product which was used without further purification.

NMR ($CDCl_3$), δ 2.64 (s, 3H), 4.61 (m, 2H), 5.30–5.49 (m, 2H), 6.00–6.12 (m, 1H), 6.74–6.87 (m, 2H), 7.73 (m, 1H), 10.11 (s, 1H).

C. Preparation of 2-Methyl-4-hydroxybenzaldehyde

The compound of Step B, 13.54 g (76.9 mmole), 1.72 g (7.69 mmole) palladium acetate, and 12.09 g (46.2 mmole) triphenylphosphine were mixed in a 250 ml flask. Formic acid, 3.2 ml (84.6 mmole), was added and the reaction was swirled. Within 15 seconds, the reaction foamed, exothermed and formed a gum which was dissolved in ethyl acetate, washed once with sodium bicarbonate and once with brine. The organic layer was chromatographed on 350 ml silica, eluting with 20%, then 40% ethyl acetate6hexane. The fractions were combined and the product crystallized from methylene chloride/hexane to give 3.61 g (35%)of product which was used without further purification.

NMR ($CDCl_3$), 2.50 (s, 3H), 6.70 (d, 1HH J=2 Hz), 6.78 (dd, 1H, J=2 Hz,9 Hz), 7.75 (d, 1H, J=9 Hz), 10.36 (s, 1H)

D. Preparation of 2-(3,5-di-t-Butyl-4-hydroxyphenyl)-4-(2-(4-formyl-3-methylphenyloxy)ethyl)oxazole Subtitled compound was prepared from 8.0 g (25.2 mmole) of the compound of Example 10 substantially in accordance with the procedure in Example 4A using 3.61g (26.5 mmole) of the compound of Step C, 6.62 g (25.2 (2 mole) triphenylphosphine and 3.97 ml (25.2 mmole) diethylazodicarboxylate. The crude product was chromatographed on silica eluting with methylene chloride. The appropriate fractions were bulked and stripped to give 5.05 g (46%) of subtitled product which was used without further purification.

NMR ($CDCl_3$), δ 1.48 (s, 18H), 2.64 (d, 3H, J=5 Hz), 3.11 (t, 2H, J=5 Hz), 4.35 (t, 2H, J=5 Hz), 5.54 (s, 1H), 6.77 (d, 1H, J=2 Hz), 6.86 (dd, 1H. J=2 Hz, 9 Hz), 7.51 (s, 1H), 7.74 (d,1.1H, J=9 Hz), 7.86 (s, 7H), 10.11 (s, 1H).

E. Preparation of 2-(3,5-di-t-Butyl-4-hydroxyphenyl)-4-(2-(4-N-rethyl-N-ethylaminomethyl-3-methylphenoxy)ethyl) oxazole Hydrochloride Hydrate Title compound was prepared from 4.54 g (10.4 mmole) of the compound of Step D substantially in accordance with the procedure of Example 1E above using 8.9 ml (104 mmole) of methylethylamine, 5.59 ml (104 mmole) of acetic acid and 693 mg (11 mmole) of sodium cyanoborohydride. Such reaction provided 1.89 g. (35%) of title product as a white foam.

FDMS-$M^+$478; Elemental analysis for ($C_{30}H_{42}N_2O_3$.HCl.0.75 $H_2O$): Calculated: C, 68.02; H, 8.48; N, 5.35. Found: C, 68.16; H, 8.48; N, 5.30. NMR ($CDCl_3$), δ 1.41 (t, 3H, J=7 Hz), 1.48 (s, 18H), 2.41 (s, 3H), 2.65 (d, 2H, J=5 Hz), 2.96 (m, 1H), 3.24 (m, 2H), 4.07–4.27 (m, 3H), 5.84 (s, 1H), 6.80 (m, 2H), 7.63 (m, 2H), 8.07 (s, 2H)

EXAMPLE 21

2-(3,5-di-t-Butyl-4-hydroxyphenyl)-4-(2-(3-chloro-4-N-methyl-N-ethylaminomethylphenoxy)ethyl) oxazole Hydrochloride Hemihydrate A. Preparation of 2-(3,5-di-t-Butyl-4-hydroxyphenyl)-4-(2-(3-chloro-4-formylphenoxy)ethyl)oxazole Subtitled compound was prepared from 6.34 g (20 mmole) of the compound of Example 1C substantially in accordance with the procedure in Example 4A using 3.60 g (23 mmole) of 2-chloro-4-hydroxybenzaldehyde, 6.03 g (23 mmole) of triphenylphosphine and 3.62 ml (23 mmole) diethylazodicarboxylate. The crude product was chromatographed, eluting with methylene chloride. The appropriate fractions were bulked and stripped to give 5.64 g (62%) of subtitled product which was used without further purification.

NMR ($CDCl_3$), δ 1.48 (s, 18H), 3.09 (t, 2H, J=7 Hz), 4.35 (t, 2H, J=7 Hz), 5.52 (s, 1H), 6.90, (dd, 1H, J=2 Hz, 9 Hz), 6.97 (d, 1H, J=2 Hz), 7.49 (s, 1H), 7.84 (s, 2H), 7.87 (d, 1H, J=9 Hz), 10.32 (s, 1H)

B. Preparation of 2-(3,5-di-t-Butyl-4-hydroxyphenyl)-4-(2-(3-chloro-4-N-methyl -N-ethylaminomethylphenoxy) ethyl) oxazole Hydrochloride Hemihydrate Title compound was prepared from 4.58 g (10 mmole) of the compound of Step A substantially in accordance with the procedure in Example 1E above using 6.54 ml (100 mmole) of methylethylamine, 5.75 ml (100 mmole) acetic acid and 661 mg (10.5 mmole) of sodium cyanobcrohydride. Such reaction provided 1.24 g. (23%) of title product as a white foam.

FDMS-$M^+$498; Elemental analysis for ($C_{29}H_{39}N_2O_3Cl$.HCl.0.5 $H_2O$): Calculated: C, 63.96; H, 7.59; N, 5.14. Found: C, 63.83; H, 7.83; N, 5.10. NMR ($CDCl_3$), 3 1.47 (s, 21H), 2.65 (d, 3H, J=5 Hz), 2.99 (m, H), 3.13 (t, 2H, J=7 Hz), 3.23 (m, 1H), 4.20–4.40 (m, 4H), 5.62 (s, 1H), 6.94 (d, 1H, J=9 Hz), 6.98 (s, 1H), 7.53 (s, H), 7.91 (s, 2H), 8.05 (d, 1H, J=9 Hz)

EXAMPLE 22

2-(3,5-di-t-Butyl-4-hydroxyphenyl)-4-(2-(3-hydroxy-4-N-methyl-N-ethylaminomethylphenoxy) ethyl)oxazole Hydrochloride Hemihydrate A. Preparation of 2-(3,5-di-t-Butyl-4-hydroxyphenyl)-4-(2-(3-hydroxy-4-formylphenoxy)ethyl)oxazole Subtitled compound was prepared from 12.68 g (40 mmole) of the compound of Example IC substantially in accordance with the procedure in Example 4A above using 6.35 g (46 mmole) of 2,4-dihydroxybenzaldehyde, 12.05 g (46 mmole) of triphenylphosphine and 7.24 ml (46 mmole) diethylazodicarboxylate. The crude product was chromatographed on silica, eluting with methylene chloride. The appropriate fractions were combined and stripped of solvent to give 9.2 g (53%) of subtitled product which was used without further purification.

NMR ($CDCl_3$), δ 1.49 (s, 18H), 3.09 (t, 2H, J=5 Hz), 4.33 (t, 2H, J=5 Hz), 5.51 (s, 1H), 6.47 (d, 1H, J=2 Hz), 6.55 (dd, 1H, J=2 Hz, 9 Hz), 7.42 (d, 1H, J=9 Hz), 7.50 (s, 1H), 7.84 (s, 2H), 9.71 (s, 1H), 11.47 (s, 1H)

B. Preparation of 2-(3,5-di-t-Butyl-4-hydroxyphenyl)-4-(2-(3-hydroxy-4-N-methyl-N-ethylaminomethylphenoxy) ethyl)oxazole Hydrochloride Hemihydrate Title compound was prepared from 3.18 g (7.28 mmole) of the compound of Step A substantially in accordance with the procedure in Example 1E above using 4.76 ml (72.8 mmole) methylethylamine, 4.16 ml (72.8 mmole) acetic acid and 481 mg (7.64 mmole) of sodium cyanoborohydride and the reaction was allowed to proceed for 2 days. Such reaction provided 1.23 g. (33%) of the title product as a white foam.

FDMS-$M^+$480; Elemental analysis for ($C_{29}H_{40}N_2O_4$.HCl.0.5 $H_2O$) Calculated: C, 66.21; H, 8.05; N, 5.32. Found: C, 66.01; H, 8.49; N, 5.09. NMR ($CDCl_3$), δ 1.41 (t, 3H, J=7 Hz), 1.48 (s, 18H), 2.65 (d, 2H, J=SHz), 2.96 (m, 1H), 3.24 (m, 2H), 4.07–4.27 (m, 3H), 6.01 (s, 1H), 6.36 (d, 1H, J=9 Hz), 6.94 (d, 1H, J=2H), 7.26 (m, 1H), 7.84 (s, 1H), 8.13 (s, 2H), 10.75 (bs, 1H)

EXAMPLE 23

2-(3,5-di-t-Butyl-4-hydroxyphenyl)-4-(2-(4-N-methyl-N-ethylaminomethyl-3,5-dimethylphenyloxy)ethyloxazole Hydrochloride Hydrate A. Preparation of 3,5-Dimethyl-allyloxy Benzene 3,5-Dimethylphenol, 12.2 g (100 mmole), 10.8 ml (125 mmole) of allyl bromide, and 16.56 g (120 mmole) of potassium carbonate was dissolved and then refluxed in 50 ml acetone, with stirring, under nitrogen for 18 hours. The reaction was cooled, the insoluble inorganics were filtered off and stripped to give 16.2 g (100%) of subtitled product, which was used without further purification.

NMR ($CDCl_3$), δ 2.29 (s, 6H), 4.50 (m, 2H), 5.25–5.44 (M, 2H), 5.99–6.12 (m, 1H), 6.56 (s, 2H), 6.60 (s, 1H)

B. Preparation of 4-Allyloxy-2,6-dimethyl-benzaldehyde

N-methyl formanilide, 20.5 ml (166 mmole), was chilled to 130, where it began to solidify. Phosphorus oxychloride, 14.4 ml (155 mmole), was added with stirring, under nitrogen. After 25 minutes, the temperature was 45°. 3,5-Dimethyl-allyloxy benzene, 16.2 g (100 mmole), prepared as describe above, was added with stirring and heated in a 70° C. oil bath. The reaction exothermed to 93° C. and was stirred under nitrogen for 30 minutes. The bath was removed and when the temperature reached 35°, the product was dissolved in chloroform. Ice was added, the layers were separated and washed once with water, twice with sodium bicarbonate, once with water and once with brine. The product was chromatographed down 500 ml of silica, eluting with chloroform to give 9.67 g (51%) of subtitled product which was used without further purification.

NMR ($CDCl_3$), δ 2.60 (s, 6H), 4.59 (m, 2H), 5.29–5.45 (m, 2H), 6.01–6.11 (m, 1H), 6.60 (s, 2H), 10.47 (s, 1H)

C. Preparation of 2,6-Dimethyl-4-hydroxy-benzaldehyde

4-Allyloxy-2,6-dimethyl-benzaldehyde, 9.67 g (50.9 mmole), 1.14 g (5.09 mmole) of palladium II acetate, and 8.00 g (30.5 mmole)of triphenylphosphine was mixed in a flask. Formic acid, 2.11 ml (56 mmole), was added and the mixture was swirled in a 80° oil bath. Within 15 seconds the reaction exothermed and turned very dark. The gum was dissolved in ethyl acetate, washed once in sodium bicarbonate, once in water, and once in brine then chromatographed on 350 ml silica, using 20%, then 40% ethyl acetate/hexane. Fractions were bulked and crystallize from methylene chloride/hexane to give 3.90 g (51%) of subtitled product which was used without further purification.

NMR ($CDCl_3$), δ 2.64 (s, 6H), 6.74 (s, 2H), 7.26 (bs, 1H), 10.09 (s, 1H)

D. Preparation of 2-(3,5-di-t-Butyl-4-hydroxyphenyl)-4-(2-(4-formyl-3,5-dimethylphenyloxy)ethyl)oxazole Title compound was prepared from 7.85 g (24.8 mmole) of the compound of Example 1C substantially in accordance with the procedure in Example 4A above using 3.9 g (26 mmole) 2,6-dimethyl-4-hydroxybenzaldehyde, 6.49 g (24.8 mmole) triphenylphosphine and 3.90 ml (24.8 mmole) diethylazodicarboxylate. The reaction was stirred under nitrogen for 18 hours. Hydrogen peroxide, 1.38 ml 30%, was added and the reaction was stirred for an additional 30 minutes, stripped, dissolved in 40 ml methylene chloride and placed in the freezer. The diethoxycarbonylhydrazine was then filtered off and the filtrate was chromatographed, eluting with methylene chloride. The appropriate fractions were bulked and stripped to give 6.73 g (60%) of subtitled product which was used without further purification.

NMR (CDCl3), δ 1.48(s, 18H), 2.59 (s, 6H), 3.12 (t, 2H, J=9 Hz), 4.34 (t, 2H, J=9 Hz), 5.58 (s, 1H),6.61 (s, 2H), 7.52 (s, 1H), 7.89 (s, 2H), 10.47 (s, 1H)

E. Preparation of 2-(3,5-di-t-Butyl-4-hydroxyphenyl)-4-(2-(4-N-methyl-N-methylaminomethyl-3,5-dimethylphenyloxy)ethyl)oxazole Hydrochloride Monohydrate Title compound was prepared substantially in accordance with the procedure in Example 1E above using 5.02 g (11.2 mmole) of 2-(3,5-di-t-butyl-4-hydroxyphenyl)-4-(2-(4-formyl-3,5-dimethylphenyloxy)ethyl)oxazole, 9.59 ml (112 mmole) methylethyl amine, 6.40 ml (112 mmole) acetic acid, and 741 mg (11.76 mmole) sodium cyancborohydride. Ethyl acetate was added and the mixture was washed once with water, once with saturated sodium bicarbonate, twice with water and once with brine. The mixture was dried, stripped of organics and chromatographed, eluting with Tethylene chloride/methanol 92:8. Fractions were bulked, stripped of organics and dissolved in methylene chloride/isopropyl ether. Hydrogen chloride gas was bubbled through the solution and the mixture was concentrated and triturated with isopropyl ether to give 4.47 g (69%) white foam.

FDMS-M+492; Elemental Analysis for $C_{31}H_{44}N_2O_3$.HCl.$H_2O$ Calculated: C, 68.05; H, 8.66; N; 5.12. Found: C, 68.06; H, 8.84; N, 4.77. NMR ($CDCl_3$), δ 1.49 (s, 18H), 1.55 (t, 3H, 5 Hz),2.48 (s, 6H), 3.23 (m, 2H), 3.36 (m,t, 2H, J=5 Hz), 3.98 (m, 1H), 4.30–4.40 (m,3H), 6.05 (s, 1H), 6.66 (s, 2H), 7.73 (s, 1H), 8.22 (s, 2H), 11.20 (bs, 1H)

EXAMPLE 24

2-(3,5-di-t-Butyl-4-hydroxyphenyl)-4-(2-(4-N-methyl-N-ethylaminomethyl-2-chlorophenyloxy)ethyl)oxazole Hydrochloride A. Preparation of 2-(3,5-di-t-Butyl-4-hydroxyphenyl)-4-(2-(4-formyl-2-chlorophenyloxy)ethyl)oxazole Subtitled compound was prepared from 3.17 g (10 mmole) of compound of Example 1C, 1.72 g (11 mmole) 3-chloro-4-hydroxy-benzaldehyde, 2.62 g (10 mmole) triphenylphosphine and 1.57 ml (10 mmole) diethylazodicarboxylate substantially in accordance with the procedure in Example 4A above. The reaction was chromatographed, eluting with 4% methanol/methylene chloride. The appropriate fractions were hulked and stripped to gave 3.51 g (77%) product which was used without further purification.

NMR ($CDCl_3$), δ 1.48 (s, 18H), 3.17 (t, 2H, J=7 Hz), 4.42 (t, 2H, J=7 Hz), 5.51 (s, 1H), 7.08 (d, 1H, J=9 Hz), 7.61 (s, 1H), 7.75 (dd, 1H, J=2 Hz,9 Hz), 7.84 (s, 2H), 7.90 (d, 1H, J=2 Hz), 9.84 (s, 1H).

B. Preparation of 2-(3,5-di-t-Butyl-4-hydroxyphenyl)-4-(2-(4-N-methyl-N-ethylaminomethyl-2-chlorophenyloxy)ethyl)oxazole Hydrochloride Title compound was prepared from 1.75 g of the compound of Step A substantially in accordance with the procedure in Example 9, using 0.66 ml (7.7 mmole) methylethylamine, 2.28 ml (7.7 mmole) titanium IV isopropoxide and 220 mg (5.74 mmole) sodium borohydride except that the reduction was stirred for 18 hours. Ammonia (6.3 ml, 2N) was added to give a thick suspension. Methylene chloride and diatomaceous earth were added and the suspension was filtered through diatomaceous earth. The filtrate was washed once with brine, dried and the organics stripped and chromatographed, eluting with methylene chloride/methanol/concentrated ammonia 90:5:0.5. The fractions were bulked, stripped of solvent and dissolved in methylene chloride/isopropyl ether. Hydrogen chloride gas was bubbled in and the material was concentrated and triturated with isopropyl ether to give 1.21 g (59%) white foam.

FDMS-$M^+$ 498; Elemental analysis for $C_{29}H_{39}N_2O_3Cl$.HCl; Calculated: C, 65.04; H, 7.53; N, 5.23. Found: C, 65.30; H, 7.72; N, 5.22. NMR ($CDCl_3$), δ 1.48 (m, 21H), 2.63 (d, 3H, J=5 Hz), 2.88–2.92 (m, 1H), 3.15 (m, 3H, J=5 Hz), 3.97–4.16 (m, 2H), 4.34 (t, 2H, J=5 Hz), 5.53 (s, 1H), 7.03 (d, 1H, J=9 Hz), 7.48 (d, 1H, J=2 Hz), 7.60 (s, 1H), 7.65 (dd, 1H, J=2 Hz, 9 Hz), 7.85 (s, 1H).

EXAMPLE 25

2-(3,5-di-t-Butyl-4-hydroxyphenyl)-4-(2-(4-N-methyl-N-ethylaminomethyl-1-naphthyloxy)ethyl)oxazole Hydrochloride Hemihydrate A. Preparation of 2-(3,5-di-t-Butyl-4-hydroxyphenyl)-4-(2-(4-formyl-1-naphthyloxy)ethyl)oxazole Subtitled compound was prepared from 7.925 g (25 mmole) of the compound of Example 1C substantially in accordance with the procedure in Example 4A using 4.95 g (28.75 mmole) of 4-hydroxy-1-naphthaldehyde, 7.53 g (28.75 mmole) of triphenylphosphine and 4.52 ml (28.75 mmole) diethylazodicarboxylate. The crude product was chromatographed with methylene chloride. The appropriate fractions were bulked and stripped to give 4.08 g (35%) product which was used without further purification.

NMR ($CDCl_3$), δ 1.48 (s, 18H), 3.26 (t, 2H, J=6 Hz), 4.57 (t, 2H, J=6 Hz), 5.51 (s, 1H), 6.97 (d, 1H, J=9 Hz), 7.56 (m, 2H), 7.69 (t, 1H, J=9 Hz), 7.85 (s, 1H), 7.91 (d, 1H, J=9 Hz), 8.33 (d, 1H, J=9 Hz), 9.30 (d, 1H, J=9 Hz), 10.20 (s, 1H).

B. Preparation of 2-(3,5-di-t-Butyl-4-hydroxyphenyl)-4-(2-(4-N-methyl-N-ethylaminomethyl-1-naphthyloxy)ethyl) oxazole Hydrochloride Hemihydrate Title compound was prepared from 3.41 g (7.24 mmole) of the compound of Step A substantially in accordance with the procedure in Example 1E above using 4.74 ml (72.4 mmole) of methylethylamine, 4.14 ml (12.4 mmol) acetic acid and 480 mg (7.6 mmole) of sodium cyanoborohydride. The crude product was chromatographed eluting with a gradient of methylene chloride/methanol/1% concentrated ammonia 100:0:00 to 90:10:1 over 10 minutes. Crude product was dissolved in methylene chloride/isopropyl ether, treated with hydrogen chloride gas and the resulting oil triturated with isopropyl ether to give 1.84 g (46%) white foam. FDMS-$M^+$ 514; Elemental analysis for $C_{33}H_{42}N_2O_3$.HCl.0.5 $H_2O$; Calculated: C, 70.76; H, 7.92; N, 5.00. Found: C, 70.52; H, 8.22; N, 4.72. NMR ($CDCl_3$), δ 1.13 (t, 3H, J=6 Hz), 1.49 (s, 18H), 2.65 (d, 2H, J=5 Hz), 2.96 (m, 1H), 3.24 (m, 1H), 3.58 (m, 2H), 4.07–4.27 (m, 3H), 6.01 (s, 1H), 6.97 (d, 1H, J=9 Hz), 7.56 (t, H, J=9H), 7.69 (t, 1H, J=9 Hz), 7.82 (m, 2H), 8.14 (d, 1H, J=9 Hz), 8.24 (m, 3H).

EXAMPLE 26

2-(3,5-di-t-Butyl-4-hydroxyphenyl)-4-(2-(4-(morpholin-4-yl-methyl)phenyloxy)ethyl)oxazole Hydrochloride Title compound was prepared from the compound of Example 1D (4.21 g, 10 mmole) substantially in accordance with the procedure in Example 1E using morpholine (8.72 ml, 100 mmole) and sodium cyanoborohydride (0.63 g, 10 mmole). The methanol was evaporated and the residue was dissolved in ethyl acetate and saturated sodium bicarbonate. The organic layer was extracted with brine, dried with sodium sulfate, evaporated to dryness, and chromatographed on silica gel using a hexane-isopropanol gradient to give the free base (3.68 g, 75%). The free base was dissolved in methylene chloride, treated with hydrogen chloride gas, and evaporated to give desired product (3.68 g, 93%).

$^1$H NMR ($CDCl_3$) δ 10.95 (bs, 1H), 7.9 (s, 2H), 7.6 (s, 1H), 7.5 (d, J=9 Hz, 2H), 6.95 (d, J=9 Hz, 2H), 5.5 (s, 1H), 4.25 (m, 4H), 4.1 (d, J=5 Hz, 2H), 3.9 (dd, J=10, 3 Hz, 2H), 3.25 (d, J=10 Hz, 2H), 3.05 (t, J=7 Hz, 2H), 2.9 (m, 2H), 1.5 (s, 18H); FDMS 492 ($M^+$-HCl); Elemental analysis for $C_{30}H_{41}ClN_2O_4$: Calculated: C, 68.10; H, 7.81; N, 5.29. Found: C, 67.93; H, 7.73; N, 5.17.

EXAMPLE 27

2-(3,5-di-t-Butyl-4-hydroxyphenyl)-4-(2-(4-(4-methylpiperazin-1-yl-methyl)phenyloxy)ethyl) oxazole Dihydrochloride Title compound was prepared from 5.05 g (12 mmole) of the compound of Example 1D substantially in accordance with the procedure in Example 1E above using N-methylpiperazine (13.3 ml, 120 mmole) and sodium cyanoborohydride (0.75 g, 12 mmole). The methanol was evaporated and the residue was dissolved in ethyl acetate and saturated sodium bicarbonate. The organic layer was extracted with brine, dried with sodium sulfate, evaporated to dryness, and chromatographed on silica gel using a methylene chloride/methanol gradient to give the free base (4.53 g, 75%). The free base was dissolved in methylene chloride, treated with hydrogen chloride gas, and evaporated to give desired product (4.53 g, 87%).

$^1$H NMR ($CDCl_3$) δ 7.95 (s, 2H), 7.55 (d, J=9 Hz, 2H), 7.5 (s, 1H), 6.95 (d, J=9 Hz, 2H), 5.5 (s, 1H), 4.3 (t, J=7 Hz, 2H), 4.15 (s, 2H), 3.9 (m, 2H), 3.75 (m, 2H), 3.45 (m, 4H), 3.05 (t, J=7 Hz, 2H), 2.9 (s, 3H), 1.5 (s, 18H); FDMS 505 ($M^+$-HCl); Elemental analysis for $C_{31}H_{45}Cl_2N_3O_3$: Calculated: C, 64.35; H, 7.84; N, 7.26. Found: C, 64.07; H, 7.67; N, 7.32.

EXAMPLE 28

2-(3,5-di-t-Butyl-4-hydroxyvphenyl)-4-(2-(4-(4-acetylpiperazin-1-yl-methyl)phenyloxy)ethyl) oxazole Hydrochloride Title compound was prepared from the compound of Example 1D (4.21 g, 10 mmole) substantially in accordance with the procedure in Example 1E using N-acetylpiperazine (12.82 g, 100 mmole) and sodium cyanoborohydride (0.63 g, 10 mmole). The methanol was evaporated and the residue was dissolved in ethyl acetate and saturated sodium bicarbonate. The organic layer was extracted with brine, dried with sodium sulfate, evaporated to dryness, and chromatographed on silica gel using a methylene chloride/methanol gradient to give the free base (3.96 g, 74%). The free base was dissolved in methylene chloride, treated with hydrogen chloride gas, and evaporated to give desired product (3.94 g, 93%).

1H NMR ($CDCl_3$) δ 10.8 (bs, 1H), 7.95 (s, 2H), 7.55 (d, J=9 Hz, 2H), 7.5 (s, 1H), 6.95 (d, J=9 Hz, 2H), 5.6 (s, 1H), 4.7 (d, J=13 Hz, 1H), 4.35 (t, J=7 Hz, 2H), 4.15 (m, 2H), 3.85 (d, J=13 Hz, 1H), 3.45 (m, 4H), 3.15 (t, J=7 Hz, 2H), 2.65 (m, 2H), 2.1 (s, 3H), 1.5 (s, 18H); FDMS 533 ($M^+$-HCl); Elemental analysis for $C_{32}H_{44}ClN_3O_4$.1.2 $H_2O$: Calculated: C, 64.95; H, 7.90; N, 7.10. Found: C, 64.67; H, 7.51; N, 6.97.

EXAMPLE 29

2-(3,5-di-t-Butyl-4-hydroxyphenyl)-4-(2-(4-thiomorpholinylmethylphenoxy)ethyl)oxazole Title product was prepared from the compound of example 1D substantially in accordance with the procedure in Example 11, except using thiomorpholine, and conducting the reaction at room temperature. The material was eluted with 0 to 3% (1% ammonium hydroxide:methanol) :chloroform gradient over a thirty minute period. Fractions containing desired product were concentrated in vacuo to an oil. The oil was treated with chloroform and saturated with hydrogen chloride gas. This solution was concentrated in vacuo to afford 3.64 g of the title compound. 1.50 g of this material was taken up into solution with tetrahydrofuran (20 ml), the solution was boiled down to approximately 10 ml, additional tetrahydrofuran (20 ml) was added and the crystals were collected by filtration. Crystals were dried in a vacuum oven overnight at 60° C. to afford 1.27 g of the title compound.

Mass Spectrum (FDMS): m/z 508 (M-HCl). $^1$H NMR ($CDCl_3$): δ 8.24 (s, 2H), 7.71 (s, 1H), 7.53 (d, J=8.6 Hz, 2H), 6.96 (d, J=8.6 Hz, 2H), 6.07 (s, 1H), 4.46 (t, J=5.7 Hz, 2H), 4.08 (t, J=5.7 Hz, 2H), 3.66 (m, 4H), 3.39 (t, J=5.7 Hz, 2H), 2.87 (m, 2H), 2.58 (m, 2H), 1.50 (s, 18H). Elemental analysis for $C_{30}H_{41}ClN_2O_3S$: Calculated: C, 66.09; H, 7.58; N, 5.14. Found: C, 66.36; H, 7.82; N, 4.85.

EXAMPLE 30

2-(3,5-di-t-Butyl-4-hydroxyphenyl)-4-(2-(4-(piperazin-1-yl-methyl)phenoxy)ethyl)oxazole Dihydrochloride Hydrate 2-(3,5-di-t-butyl-4-hydroxyphenyl)-4-(2-(4-(4-acetylpiperazin-1-yl-methyl)phenoxy)ethyl)oxazole hydrochloride prepared as described in Example 28 above (0.97 g, 1.82 mmole) was dissolved in 4N hydrochloric acid and stirred for 1.5 hours at 80° C. The reaction was then diluted with ethyl acetate and neutralized with saturated sodium bicarbonate. The organic layer was extracted with brine, dried over sodium sulfate, evaporated to dryness, and chromatographed on silica gel using a methylene chloride/methanol/ammonium hydroxide gradient to give the free base (0.67 g, 75%). The free base (1.29 g, 2.62 mmol) was dissolved in methylene chloride, treated with hydrogen chloride gas, and evaporated to give desired product (1.35 g, 91%).

$^1$H NMR (CDCl$_3$) δ 10.15 (bs, 1H), 9.95 (bs, 1H), 7.95 (s, 2H), 7.55 (m, 3H), 6.95 (m, 2H), 5.7 (s, 1H), 4.4 (bs, 2H), 4.25 (bs, 2H), 4.0–3.8 (m, 8H), 3.1 (bs, 2H), 1.5 (s, 18H); FDMS 491 (M$^+$-HCl); Elemental analysis for C$_{30}$H$_{43}$Cl$_2$N$_3$O$_3$.1.4 H$_2$O: Calculated: C, 61.09; H, 7.83; N, 7.12. Found: C, 60.71; H, 7.43; N, 7.02.

EXAMPLE 31

2-(3,5-di-t-Butyl-4-hydroxyphenyl)-4-(2-(4-(imidazol-1-yl-methyl)phenoxy)ethyl)oxazole Hydrochloride Monohydrate A. Preparation of N-p-Methoxybenzylimidazole To a stirred solution of imidazole (25.53 g, 375 mmole) in acetonitrile (625 ml) was added p-methoxybenzyl chloride (16.95 ml, 125 mmole). The reaction was refluxed for 16 hours, evaporated to dryness, and redissolved in methylene chloride and saturated sodium bicarbonate. The organic layer was extracted with water twice. Standard acid/base workup gave N-p-methoxybenzylimidazole (16.3 g, 69%) which was used without further purification:

$^1$H NMR (CDCl$_3$) δ 7.5 (bs, 1H), 7.1 (m, 3H), 6.9 (m, 3H), 5.0 (s, 2H), 3.8 (s, 3H).

B. Preparation of N-p-Hydroxybenzylimidazole

To a stirred solution of the compound of Step A (16.3 g, 86.1 mmole) in methylene chloride (860 ml) cooled to 5° C., was added boron tribromide (32.6 ml, 344.4 mmole) dropwise over 15 minutes. After 2 hours at 5° C., the reaction was quenched with methanol dropwise, evaporated to dryness, and redissolved in methanol, water, and methylene chloride. The pH was adjusted to 8.4 with sodium hydroxide. The organic layer was dried over sod4um sulfate and evaporated to dryness to give N-p-hydroxybenzylimidazole (13.6 g, 91%) which was used without further purification:

$^1$H NMR (DMSO-d$_6$) δ 9.5 (bs, 1H), 7.7 (bs, 1H), 7.1 (m, 3H), 6.9 (bs, 1H), 6.75 (d, J=9 Hz, 2H), 5.05 (s, 2H); FDMS 174 (M$^+$).

C. Preparation of 2-(3,5-di-t-Butyl-4-hydroxyphenyl)-4-(2-(4-(imidazol-1-ylmethyl)phenoxy)ethyl)oxazole Hydrochloride Monohydrate Title compound was prepared from the compound of Example 1C (24.75 g, 78.1 mmole) substantially in accordance with the procedure in Example 4A using the compound of Step B, (13.6 g, 78.1 mmole), and triphenylphosphine (22.5 g, 85.9 mmole). The filtrate was extracted with water and brine and the organic layer was dried over sodium sulfate, evaporated to dryness, chromatographed on silica gel using a methylene chloride-isopropanol gradient, and triturated with hot diethyl ether to give the free base (2.51 g, 7%). The free base was dissolved in methylene chloride (65 ml), treated with hydrogen chloride gas, and evaporated to give desired product (2.6,3 g, 97%):

$^1$H NMR (CDCl$_3$) δ 9.5 (s, 1H), 8.0 (s, 2H), 7.6 (s, 1H), 7.3 (m, 3H), 7.1 (s, 1H), 6.95 (d, J=9 Hz, 2H), 5.8 (s, 1H), 5.4 (s, 2H), 4.35 (t, J=7 Hz, 2H), 3.2 (d, J=7 Hz, 2H), 1.5 (s, 18H); FDMS 473 (M$^+$-HCl); Elemental analysis for C$_{29}$H$_{36}$ClN$_3$O$_3$.H$_2$O: Calculated: C, 65.96; H, 7.25; N, 7.96. Found: C, 65.75; H, 7.07; N, 8.09.

EXAMPLE 32

2-(3,5-di-t-Butyl-4-hydroxyphenyl)-4-(2-(4,5-dihydro-1H-iamidazol-2-ylmethyl)phenox) ethyloxazole Hydrochloride A. Preparation of 2-(3,5-di-t-Butyl-4-hydroxyphenyl)-4-(2-(4-cyanomethylphenoxy)ethyl)oxazole To a suspension of the compound of Example 1C, 4-hydroxybenzyl cyanide, triphenyiphosphine and 0.7M (mmole alcohol/ml tetrahydofuran) reaction solution was added diethylazodicarboxylate. After stirring at 24° C. for approximately 24 hours, the reaction was concentrated in vacuo to a brown oil. Material was treated with chloroform (30 ml), triturated and the insolubles were filtered and washed with chloroform (20 ml). The filtrate was concentrated in vacuo to an oil, treated with toluene and subjected to preparatory chromatography. The material was eluted with 0 to 10% methanol/toluene gradient over a thirty minute period. Fractions containing the desired product were concentrated in vacuo to afford 12.18 g (88%) of the subtitled compound.

Mass Spectrum (FDMS): m/z 432 (M). $^1$H NMR (DMSOd$_6$): δ 7.91 (s, 1H), 7.72 (s, 2H), 7.52 (bs, 1H), 7.25 (d, J=8.6 Hz, 2H), 6.98 (d, J=8.6 Hz, 2H), 4.24 (t, J=6.5 Hz, 2H), 3.93 (s, 2H), 2.97 (t, J=6.5 Hz, 2H), 1.41 (s, 18H). Elemental analysis for C$_{27}$H$_{32}$N$_2$O$_3$: Calculated: C, 74.97; H, 7.46; N, 6.48. Found: C, 75.17; H, 7.41; N, 6.21.

B. Preparation of 2-(3,5-di-t-Butyl-4-hydroxyphenyl)-4-(2-(4,5-dihydro-1H-imidazol-2-ylmethyl)phenoxy) ethyloxazole Hydrochloride To a solution of the compound of Step A (24 mmole, 10.39 g) in ethanol (2 ml) and diethyl ether (50 ml) at −10° C. hydrogen chloride gas was bubbled through over a thirty minute period. Reaction was maintained at 0° C. After four days, the supernatant was decanted off then absolute ethanol (50 ml) and diethyl ether (50 ml) were added. The reaction was cooled to 0° C. then hydrogen chloride gas was passed through the solution for approximately four hours. After stirring at 0° C. for four hours, the reaction was concentrated in vacuo to a foam. Next, the foam was taken up into absolute ethanol (50 ml) then treated with ethylene diamine (48 mmole, 2.88 g). The resulting suspension was refluxed for approximately 32 hours, filtered hot and the insolubles washed with ethanol (20 ml). The filtrate was concentrated in vacua to an oil. The oil was treated with chloroform (100 ml) and washed with saturated sodium bicarbonate (2×50 ml) and brine (1×50 ml). Organics were dried over sodium sulfate, filtered and concentrated in vacua, to afford 8.38 g of a foam. Material was taken up into chloroform and chromatographed. The material was eluted with 10% (1% ammonium hydroxide/methanol) chloroform gradient over a thirty minute period. Remainder of the material was eluted with 10% (1% ammonium hydroxide/methanol) chloroform. Fractions containing the desired product were concentrated in vacuo to a foam. Material was taken up into methylene chloride (100 ml) and washed with saturated sodium bicarbonate (2×50 ml) and (1×50 ml). Organics were dried over sodium sulfate, filtered, then hydrogen chloride gas was passed through the solution. This solution was concentrated in vacuo to afford a foam. A portion of the foam (1.26 g) was treated with methylene chloride (20 ml) and isopropyl ether (10 ml) then boiled down to approximately 20 ml total volume. The turbid solution was cooled at −10° C. for approximately one hour then decanted. The remaining oil was concentrated in vacuo to afford 1.08 g of a foam.

Mass Spectrum (FDMS): m/z 476 (M+1). $^1H$ NMR ($CdCl_3$): δ 7.85 (s, 2H), 7.55 (s, 1H), 7.47 (d, J=8.5 Hz, 2H), 6.78 (d, J=8.5 Hz, 2H), 5.59 (s, 1H), 4.19 (t, J=6.4 Hz, 2H), 3.96 (s, 2H), 3.80 (s, 4H), 3.04 (t, J=6.4 Hz, 2H), 1.46 (s, 18H). Elemental analysis for $C_{29}H_{38}ClN_3O_3.C_6H_{14}O$: Calculated: C, 74.97; H, 7.46; N, 6.48. Found: C, 75.17; H, 7.41; N, 6.21.

EXAMPLE 33

6-[2-[(3,5-di-tert-Butyl-4-hydroxyphenyl)-4-oxazolyl]ethoxy]-1,2,3,4-tetrahydroisoquinoline Hydrochloride A. Preparation of N-tert-Butoxycarbonyl-6-hydroxy-1,2,3,4-tetrahydroisoquinoline A suspension of 6-hydroxy-1,2,3,4-tetrahydroisoquinoline oxalate (0.17 mole, 40.04 g) in methanol (150 ml) and tetrahydrofuran (420 ml) was treated with diisopropylethylamine (0.38 mole, 48.50 g) then with a solution of di-tert-butyl dicarbonate (0.13 mole, 27.30 g) in tetrahydrofuran (10 ml). After stirring at room temperature for approximately 4 hours, the material was treated with methylene chloride (500 ml), brine (250 ml) and 10% aqueous sodium sulfate (250 ml). Phases were separated, the organic phase was washed with 10% aqueous sodium sulfate (3×250 ml), brine (1×250 ml) then dried over sodium sulfate, filtered and concentrated in vacuo to a solid. The material was treated with methylene chloride and chromatographed, eluting with 0 to 35% (ethyl acetate/hexane) gradient over a thirty minute period. Fractions containing the desired product were concentrated in vacuo to afford 27.63 g (66%) of the subtitled compound.

Mass Spectrum (FDMS): m/z 249 (M), 148 (M-101). $^1H$ NMR ($DMSOd_6$): δ 9.21 (s, 1H), 6.93 (d, 1H), 6.58 (dd, J=2.4, 8.1 Hz, 1H), 6.53 (d, J=2.4 Hz, 1H), 4.36 (s, 2H), 3.48 (t, J=5.9 Hz, 2H), 2.66 (t, J=5.9 Hz, 2H), 1.41 (s, 9H). Elemental analysis for $C_{14}H_{19}NO_3$: Calculated: C, 67.45; H, 7.68; N, 5.62. Found: C, 67.74; H, 7.53; N, 5.59.

B. Preparation of 6-[2-[(3,5-di-tert-Butyl-4-hydroxyphenyl)-4-oxazolyl]ethoxy]-2-tert-butoxycarbonyl-1,2,3,4-tetrahydroisoquinoline.

The title compound was prepared substantially as described in Example 4A except using the compound of Step A and 0.7M reaction solution. At approximately 3.8 hours, the reaction was concentrated in vacuo to an oil. The oil was treated with methylene chloride (10 ml) and the insolubles were collected by filtration and washed with methylene chloride (10 ml). The filtrate was then treated with methylene chloride (25 ml), washed with O.IN sodium hydroxide (3×50 ml) and 10% aqueous sodium sulfate (2×50 ml). Organics were concentrated in vacuo to a foam, treated with ethyl acetate and subjected to preparatory chromatography. The material was eluted with 10 to 40% (ethyl acetate/hexane) gradient over a thirty minute period. Fractions containing title compound were combined, concentrated in vacuo, and chromatographed. Material was eluted with 10 to 25% acetone:hexane gradient over a thirty minute period. Fractions containing desired product were concentrated in vacuo to afford 5.60 g (56%) of the subtitled compound as a foam.

Mass Spectrum (FDMS): m/z 548 (M). $^1H$ NMR ($DMSOd_6$): δ 7.89 (s, 1H), 7.70 (s, 2H), 7.50 (s, 1H), 7.04 (d, 2H), 6.77 (m, 3H), 4.39 (s, 2H), 4.21(t, 2H), 3.48 (m, 2H), 2.93 (t, 2H), 2.70 (t, 2H), 1.39 (s, 27H).

C. Preparation of 6-[2-[(3,5-di-tert-Butyl-4-hydroxyphenyl)-4-oxazolyl]ethoxy]-1,2,3,4-tetrahydroisoquinoline Hydrochloride A solution of the compound of Step B (9.8 mmole, 5.60 g) in methylene chloride (33 ml) was treated with thiophenol (98.1 mmole, 10.81 g). The reaction was cooled to −10° C. then treated with trifluoroacetic acid (98.1 mmole, 8.26 g). After approximately 1.5 hours, the reaction was warmed to 24° C. After stirring 5.5 hours at 24° C., the reaction was concentrated in vacuo, treated with chloroform and chromatographed. Material was eluted with 0 to 10% (1% ammonium hydroxide/methanol):chloroform gradient over a fifteen minute period. Fractions containing desired product were reduced in volume, washed with water (50 ml), dried over sodium sulfate, filtered and concentrated in vacuo to afford an oil. Material was taken up into chloroform, then saturated with hydrogen chloride gas. This solution was concentrated in vacuo to afford 2.40 g of the title compound. This material was recystallized from 3:1 diisopropyl ether methylene chloride to afford 760 mg of the title compound.

Mass Spectrum(ion spray MS): m/z 449 (M+1). $^1H$ NMR ($DMSOd_6$): δ 7.91 (s, 1H), 7.72 (s, 2H), 7.55 (s, 1H), 7.12 (d, J=8.6 Hz, 2H), 6.85 (m, 3H), 4.23 (t, J=6.5 Hz, 2H), 4.15 (m, 2H), 3.32 (m, 2H), 2.96 (m, 4H), 1.41 (s, 18H).

EXAMPLE 34

6-[2-[(3,5-di-tert-Butyl-4-hydroxyphenyl)-4-oxazolyl]ethoxy]isoquinoline Hydrochloride Monohydrate Title compound was prepared from compound of Example 1C (19.1 mmole, 6.07 g), triphenylphosphine (21.1 mmole, 5.52 g) and 6-hydroxyisoquinoline (21.1 mmole, 3.07 g) in tetrahydrofuran (43 ml) at −10° C. (ice/acetone bath) was added diethylazodicarboxylate (21.1 mmole, 3.67 g) over an eleven minute period. After the addition was complete, the reaction was stirred at room temperature. At approximately 3.8 hours the reaction was concentrated in vacuo to an oil. The oil was taken up into chloroform then chromatographed. Material was eluted with 70–85% ethyl acetate/hexane gradient over a thirty minute period. Fractions containing desired product were combined, reduced in volume and chromatographed. Material was eluted with 0–15% methanol/toluene gradient over a thirty minute period. Fractions containing desired product were combined and concentrated in vacuo to a solid. The solid was treated with chloroform (100 ml), hydrogen chloride gas was passed through the solution which was then concentrated in vacuo to a yellow foam. The foam was triturated in diisopropyl ether (100 ml) then filtered. Insolubles were treated with toluene (100 ml), heated until boiling, filtered hot, and washed with toluene (50 ml).

These insolubles were crystallized from methylene chloride. Crystals were treated with chloroform (60 ml), and then with hydrogen chloride gas and concentrated in vacuo to a foam. Material was triturated in toluene (100 ml) and filtered and the insolubles were collected by filtration to afford 1.38 g of product.

Mass Spectrum (ion spray): m/z 444 (M-HCl). $^1H$ NMR ($DMSOd_6$): δ 9.71 (s, 1H); 8.56 (d, 1H), 8.44 (d, 1H), 8.28 (d, 1H), 7.99 (s, 1H), 7.84 (d, 1H), 7.73 (s, 2H), 7.64 (dd, 1H), 7.56 (bs, 1H), 4.56 (t, 2H), 3.13 (t, 2H), 1.41 g (s, 18H). Elemental analysis for $C_{28}H_{33}ClN_2O_3.1.0\ H_2O$: Calculated: C, 67.38; H, 7.07; N, 5.61. Found: C, 67.60; H, 6.87; N, 5.35.

EXAMPLE 35

2-(3,5-di-t-Butyl-4-hydroxyphenyl)-4-(2-(5-N-ethyl-N-methylaminomethylpyrid-2-yl-oxy)ethyl)oxazole Dihydrochloride A. Preparation of 2-(3,5-di-t-Butyl-4-hydroxyphenyl)-4-(2-(5-formylpyrid-2-yl-oxy)ethyl)oxazole The title compound was prepared substantially as described in Example 4 except using 2-pyridone-5-carboxaldehyde. After stirring at 22° C. for approximately 15.5 hours, the reaction was treated with water (2.1 eq., 870 51), stirred 10 minutes then concentrated in vacuo to afford a foam. The foam chromatographed, eluting with a gradient of 50 to 65% ethyl acetate hexane over a thirty minute period. Fractions containing title compound were combined and concentrated in vacuo to afford a purple solid. The solid was treated with diethyl ether, triturated, stirred approximately 4 hours then filtered. The filtrate was concentrated in vacuc to afford a purple foam. The foam was chromatographed, eluting with a gradient of 20 to 35% acetone:hexane over a thirty minute period. Fractions containing the title compound were combined and concentrated in vacuo to afford 2.28 g of the subtitled compound as a foam. This material was taken on to the next step without further purification.

Mass Spectrum (FDMS): m/z 422. (M). 1H NMR ($CDCl_3$): δ 9.43 (s, 1H), 7.82 (s, 2H), 7.78 (m, 2H), 7.34 (s, 1H), 6.59(d, J=10.3 Hz, 1H), 5.54 (s, 1H), 4.39 (t, J=6.4 Hz, 2H), 3.07 (t, J=6.4 Hz, 2H), 1.49 (s, 18H).

B. Preparation of 2-(3,5-di-t-Butyl-4-hydroxyphenyl)-4-(2-(5-N-ethyl-N-methylaminomethyl-pyrid-2-yl-oxy)ethyl) oxazole Dihydrochloride.

Title compound was prepared from the compound of Step A substantially in accordance with the procedure in Example 11. The material was chromatographed, eluting with a gradient of 0 to 5% (1% ammonium hydroxide:methanol) :chloroform over a thirty minute period. Remaining fractions were eluted with 5% (1% ammonium hydroxide:methanol):chloroform. Fractions containing the title compound were combined and concentrated in vacuo to afford an oil. The oil was treated with chloroform then hydrogen chloride gas resulting in crystalline formation. Crystals were collected by filtration and washed with chloroform affording 1.44 g. Material was recrystallized from methanol:tetrahydrofuran to afford 1.25 g of the title compound.

Mp (C): 237–239 Mass Spectrum (FDMS): m/z 465. (M-2HCl). 1H NCR ($DMSOd_6$): δ 10.73 (bs, 1H), 7.88 (s, 1H), 7.78 (d, J=2.3 Hz, 1H), 7.64(dd, J=2.3, 9.4 Hz, 1H), 6.45 (d, J=9.4 Hz, 1H), 4.12 (t, J=6.9 Hz, 2H), 3.97 (m, 4H), 2.76–3.02 (m, 4H), 2.50 (s, 3H), 1.41 (s, 18H), 1.16 (t, J=7.2 Hz, 3H). Elemental analysis for $C_{28}H_{41}Cl_2N_3O_3$: Calculated: C, 62.45; H. 7.67; N, 7.80. Found: C, 62.46; H, 7.71; N, 7.79.

EXAMPLE 36

2-(3,5-di-t-Butyl-4-hydroxyphenyl)-4-(2-(4-N-methyl-N-ethylaminomethylphenylthio)ethyl) oxazole Hydrochloride Monohydrate A. Preparation of 2-(3,5-di-t-Butyl-4-hydroxyphenyl)-4-(2-(4-formylphenylthio)ethyl)oxazole Subtitled compound was prepared by dissolving 3.84 g (14.6 mmole) triphenylphosphine, in 45 ml of tetrahydrofuran, chilling to −9° C. then adding under nitrogen, 2.3 ml (14.6 mmole) diethylazodicarboxylate. The reaction exothermed to −1° C. and was chilled again to −6° C. 4.64 g (14.6 mmole) of the compound of Example 1C was added. The deep red solution was stirred 15 minutes when 2.22 g (16.1 mmole) 4-mercaptobenzaldehyde (*Tet.Lett.* 25, (17), 1753–1756, 1984) was added and the reaction was allowed to stir for 18 hours. The reaction was stripped and chromatographed eluting with 10% to 50% ethyl acetate/hexane gradient over 30 minutes. The appropriate fractions were bulked and stripped to give 3.48 g (54%) product which was used without further purification.

NMR ($CDCl_3$), δ 1.46 (t, 3H, J=9 Hz), 1.50 (s, 18H), 2.64 (d, 2H, J=5 Hz), 2.88–2.97 (m, 1H), 3.17 (t, 2H, J=9 Hz), 3.51 (t, 2H, J=9 Hz), 3.97–32 (m, 2H), 6.05 (s, 1H), 7.46 (d, 2H, J=9 Hz), 7.56 (d, 2H, J=9 Hz), 7.65 (s, 1H), 8.21 (s, 2H).

B. Preparation of 2-(3,5-di-t-Butyl-4-hydroxyphenyl)-4-(2-(4-N-methyl-N-ethylaminomethylphenylthio)ethyl)oxazole Hydrochloride Monohydrate Methylethylamine 1.72 ml (20 mmole) and 5.92 ml (20 mmole) of titanium tetraisopropoxide were dissolved in 45 ml of punctilious ethanol, with stirring, under nitrogen and stirred 1 hour. Compound of Step A (4.38 g, 10 mmole), was added and the reaction was stirred for 3.5 hours. Sodium borohydride (570 mg, 15 mmole) was added and the reaction was stirred an additional 18 hours. ammonia (16.3 ml, 2N) was added to give a thick suspension followed by 104 ml of methylene chloride. Diatomaceous earth (13 g) was added and the mixture was stirred and filtered through diatomaceous earth. The filtrate was washed one time with brine and dried, stripped and chromatographed, eluting with methylene chloride/methanol/concentrated ammonia 90:5:0.5. The fractions were combined, stripped of solvent, and dissolved in methylene chloride/isopropyl ether. Hydrogen chloride gas was bubbled in and the solution was concentrated and triturated with isopropyl ether to give 2.86 g (55%) of title product as a white foam.

FDMS-$M^+$ 480; Elemental analysis for $C_{29}H_{40}N_2O_2S.HCl.H_2O$; Calculated: C, 64.86; H, 8.11; N, 5.21. Found: C, 64.56; H, 8.37; N, 4.93. NMR ($CDCl_3$), δ 1.46 (t, 3H, J=9 Hz), 1.50 (s, 18H), 2.64 (d, 2H, J=5 Hz), 2.88–2.97 (m, 1H), 3.17 (t, 2H, J=9 Hz), 3.51 (t, 2H, J=9 Hz), 3.97–32 (m, 2H), 6.05 (s, 1H), 7.46 (d, 2H, J=9 Hz), 7.56 (d, 2H, J=9 Hz), 7.65 (s, 1H), 8.21 (s, 2H).

EXAMPLE 37

2-(3,5-di-t-Butyl-4-hydroxyphenyl)-4-(2-(4-N-methyl-N-ethylaminomethylphenoxy)ethyl)-5-methyloxazole Hydrochloride Monohydrate A. Preparation of Ethyl 4-Chloro-3-oxopentanoate Potassium ethyl malonate, 34 g (200 mmole) (Organic Synthesis Coll. Vol. IV, p. 417), 23.75 g (250 mmole) magnesium chloride, and 44.5 ml (320 mmole) triethylamine were suspended in 1.0 L acetonitrile, with stirring, under nitrogen. 2-Chloro-propionyl chloride, 9.7 ml (100 mmole), was added and the mixture was stirred under nitrogen for 18 hours. 100 ml of 5N hydrochloric acid, was added and the reaction was stirred for 2 hours. Layers were separated and organics stripped to give 21.09 g of crude product which was filtered through 300 ml silica, eluting with 20% ethyl acetate/hexane to give 10.37 g (58%) product.

NMR ($CDCl_3$), δ 1.27 (t, 3H, J=4 Hz), 1.62 (d, 3H, J=4 Hz), 3.72 (dd, 2H, J=42 Hz), 4.52 (q, 2H, J=4 Hz).

B. Preparation of 2-(3,5-di-t-Butyl-4-hydroxyphenyl)-4-carbethoxymethyl-5-methyloxazole Compound of example 1A, 6.6 g (26.5 mmole) and 10.3 g (57.7 mmole) of the compound of Step A were stirred together neat, at 140° C., under nitrogen, for a total of 6.5 hours. The reaction was cooled and chromatographed on 300 ml silica, eluting with 20%, then 50% ethyl acetate/hexane to give 4.48 g (45%) product.

FDMS-M+=373 NMR (CDCl3), δ 1.27 (t, 3H, J=4 Hz), 1.47 (s, 18H), 2.34 (s, 3H), 3.54 (s, 2H), 4.18 (q, 2H, J=4 Hz), 5.46 (s, 1H), 7.78 (m, 2H).

C. Preparation of 2-(3,5-di-t-Butyl-4-hydroxyphenyl)-4-(2-hydroxyethyl)-5-methyloxazole Starting ester, the compound of Step B 4.43 g (11.88 mmole), was dissolved in 83 ml tetrahydrofuran with stirring, under nitrogen. Solid lithium aluminum hydride (LAH), 450 mg (11.88 mmole), was cautiously added. There was much bubbling. The mixture was stirred 30 minutes and another 225 mg (5.94 mmole) lithium aluminum hydride was added and the reaction stirred under nitrogen overnight. Water (0.675 ml) was cautiously added followed by 0.675 ml 15% sodium hydroxide, followed by 2.0 ml water. The inorganics were filtered off and the filtrate was stripped, dissolved in ethyl acetate, washed once with 1 N hydrochloric acid, twice with brine, and stripped to give 3.61 g (92%) of product which was used without further purification.

FDMS-M+=331 NMR (CDCl3), δ 1.48 (s, 18H), 2.32 (s, 3H), 2.73 (t, 2H, J=4 Hz), 3.91 (t, 2H, J=4 Hz), 5.51 (s, 1H), 7.81 (s, 2H).

D. Preparation of 2-(3,5-di-t-Butyl-4-hydroxyphenyl)-4-(2-(4-formylphenoxy)ethyl)-5-methyloxazole The compound of Step C 3.61 g (10.9 mmole), 1.53 g (12.5 mmole) 4-hydroxybenzaldehyde, and 3.29 g (12.5 mmol) triphenylphosphine were dissolved in 30 ml tetrahydrofuran with stirring, under nitrogen. The solution was chilled to −5° C. and a solution of 1.97 ml (12.5 mmole) diethyldiazodicarboxylate in 10 ml. tetrahydrofuran was added over 10 minutes, with stirring. The reaction exothermed to +3° C. The bath was removed and the reaction stirred under nitrogen for 3 days. The reaction was stripped, dissolved in methylene chloride and placed in the freezer. The diethoxycarbonylhydrazine was then filtered off and the filtrate was chromatographed on 400 ml silica, eluting with a 5% isopropyl alcohol/hexane. The appropriate fractions were bulked and stripped to give 3.52 g (74%) product which was used without further purification.

FDMS-M+=435. NMR (CDCl3), δ 1.48 (s, 18H), 2.37 (s, 3H), 3.01 (t, 2H, J=4 Hz), 4.34 (t, 2H, J=4 Hz), 5.48 (s, 1H), 7.00 (d, 2H, J=7 Hz), 7.80 (s, 2H), 7.82 (d, 2H, J=7 Hz), 9.87 (s, 1H).

E. Preparation of 2-(3,5-di-t-Butyl-4-hydroxyphenyl)-4-(2-(4-methylethylaoivnomethylphenoxy)ethyl)-5-methyloxazole Hydrochloride Hydrate Methylethylamine, 0.71 ml (8.32 mmole) and 2.46 ml (8.32 mmole) Ti(OPr)4 were dissolved in 17 ml of ethanol and stirred f or 10 minutes under nitrogen. Compound of step D, 1.75 g (4.16 mmole), was added and t he mixture was stirred for 4 hours. Sodium borohydride, 240 mg (6.23 mmole) was added and the reaction was stirred for 3 days. Ammonia, 5.8 ml 2N, was added to give a thick suspension. Methylene chloride (40 ml) was added then 5.3 g diatomaceous earth and the mixture was stirred, and filtered through diatomaceous earth. The filtrate was washed 2 times with brine then dried. The organics were stripped and chromatographed, eluting with methylene chloride/methanol/concentrated ammonia 90:10:1. Fractions were bulked, stripped, dissolved in methylene chloride/isopropyl ether. Hydrogen chloride gas was bubbled in. Product was evaporate to dryness to give 1.36 g (63%) of a white foam.

FDMS-M+478; Elemental Analysis for $C_{30}H_{42}N_2O_3$.HCl.$H_2O$; Calculated: C, 67.58; H, 8.51; N, 5.25. Found: C, 67.21; H, 8.61; N, 5.06. NMR ($CDCl_3$), δ 1.44 (t, 3H, J=4 Hz), 1.49 (m, 18H), 2.51 (s, 3H), 2.60 (d, 2H, J=4 Hz), 2.88–3.23 (m, 4H), 3.99–4.14 (m, 2H), 4.43 (t, 2H, J=6 Hz), 5.99 (s, 1H), 6.92 (d, 2H, J=7 Hz), 7.49 (d, 2H, J=7 Hz), 8.16 (s, 2H).

EXAMPLE 38

2-(3,5-di-t-Butyl-4-hydroxyphenyl)-4-(2-(4-N-methyl-N-ethylaminomethylphenoxy)ethyl)thiazole Hydrochloride Hydrate A. Preparation of N-Methyl-(3,5-di-t-butyl-4-hydroxy)benzamide (3,5-di-t-butyl-4-hydroxy)benzoic acid, 75 g (300 mmole) and 53.46 g (330 mmole) carbonyldiimidazole were refluxed in 900 ml tetrahydrofuran, with stirring, under nitrogen, for 2 hours. The reaction was cooled and 300 ml 40% aqueous methylamine was added and stirred under nitrogen at room temperature for 18 hours. The mixture was stripped to a wet solid and 500 ml of water was added. The mixture was stirred, and filtered to give 88.5 g (100%) product, which contained approximately 30 mole % imidazole. The product was used without further purification. NMR (CDCl3), δ 1.44 (s, 18H), 2.98 (d, 3H, J=4 Hz), 6.2 (bs, 1H), 7.58 (s, 2H).

B. Preparation of N-Methyl-(3,5-di-t-butyl-4-hydroxy)thiobenzamide

The compound of Step A 88.5 g (ca. 300 mmole), and 60.6 g (150 mmole) Lawesson's reagent was dissolved in 300 g hexamethylphosporamide at 100° C. and stirred under nitrogen at 100° C. for 1 hour. The mixture was cooled, water was added, and the mixture was extracted twice with diethyl ether. The combined organic layers were washed three times with water, and the organic layer was stripped to give 91.3 g of crude product which was triturated with 250 ml methylene chloride to give 43.7 g product. Hexane, 350 ml, was added to the filtrate with stirring to give a second crop of 26.7 g product. The filtrate was boiled down to 400 ml to give a third crop of 7.2 g product. The total yield was 77.6 g (93%)

NMR (CDCl3), δ 1.44 (s, 18H), 3.33 (d, 3H, J=4 Hz), 5.52 (bs, 1H), 7.60 (s, 2H).

C. Preparation of 3,5-di-t-Butyl-4-hydroxythiobenzoic acid, (3-ethoxycarbonyl-2-oxo-1-propionyl)ester The compound of Step B 42.0 g (150 mmole), 27 ml (200 mmole) ethyl 3-chloroacetoacetate and 24.9 g (150 mmole) potassium iodide was stirred in 1.0 1 tetrahydrofuran, under nitrogen, and refluxed for 4.5 hours. The reaction was cooled and 75 ml water was added and the mixture stirred for 18 hours. The organics were stripped, and the crude product was dissolved in chloroform, washed once with water, and once with brine, then chromatographed, eluting with a gradient of methylene chloride to methylene chloride/methanol/concentrated ammonia, 90:10:1 over 10 minutes. The partially purified product was then chromatographed on 600 ml silica, eluting with 10% ethyl acetate/hexane to give 28 g (44%) product.

FDMS-M+=394 NMR (CDCl3), δ 1.25 (t, 3H, J=4 Hz), 1.45 (s, 18H), 3.66 (s, 2H), 3.98 (s, 2H), 4.18 (q, 2H, J=4 Hz), 5.80 (s, 1H), 7.83 (s, 2H).

D. Preparation of 2-(3,5-di-t-Butyl-4-hydroxyphenyl)-4-carbethoxymethylthiazole

The compound of Step C 25.1 g (63.7 mmole), and 19.6 g (255 mmole)of ammonium acetate was refluxed in 320 ml glacial acetic acid, with stirring, under nitrogen, for 3.25 hours. The reaction was cooled and ethyl acetate and water were added. Layers were separated and the aqueous layer was washed once with ethyl acetate. The combined organic layers were washed once with water and 8 times with saturated sodium bicarbonate solution to achieve a final wash of pH 9. The organic layer was stripped and the crude product chromatographed on 600 ml silica, eluting with 10% ethyl acetate/hexane to give 14.96 g (57%) product.

FDMS-M+=375. NMR (CDCl3), δ 1.29 (t, 3H, J=4 Hz), 1.48 (s, 18H), 3.87 (s, 2H), 4.21 (q, 2H, J=4 Hz), 5.45 (s, 1H), 7.09 (s, 1H), 7.72 (s, 2H).

E. Preparation of 2-(3,5-di-t-Butyl-4-hydroxyphenyl)-4-(2-hydroxyethyl)thiazole

The compound of Step D 5.0 g (13.33 mmole), was dissolved in 95 ml tetrahydrofuran with stirring, under nitrogen. Solid lithium aluminum hydride, 760 mg (20 mmole), was cautiously added. There was much bubbling. The mixture was stirred under nitrogen for 1 hour. Water, 0.76 ml H₂O, was cautiously added followed by 0.76 ml 15% sodium hydroxide, followed by 2.3 ml water. The inorganics were filtered off and the filtrate was stripped, dissolved in ethyl acetate, washed once with 1 N hydrochloric acid, twice with brine, and stripped to give 4.42 g (99%) product which was used without further purification.

FDMS-M+=333 NMR (CDCl3), δ 1.48 (s, 18H), 3.02 (t, 2H, J=4 Hz), 3.98 (t, 2H, J=4 Hz), 5.50 (s, 1H), 6.87 (s, 1H), 7.73 (s, 2H).

F. Preparation of 2-(3,5-di-t-Butyl-4-hydroxyphenyl)-4-(2-(4-formylphenoxy)ethyl)thiazole The compound of Step E 4.20 g (12.6 mmole), 1.76 g (14.44 mmole) 4-hydroxybenzaldehyde, and 3.79 g (14.44 mmole) triphenyl phosphine were dissolved in 37 ml tetrahydrofuran with stirring, under nitrogen. The solution was chilled to −10° C. and a solution of 2.27 ml (14.44 mmole) diethylazodicarboxylate in 12.5 ml. tetrahydrofuran was added over 10 minutes, with stirring. The reaction exothermed to −1° C. The bath was removed and the reaction stirred under nitrogen overnight. The reaction was stripped, dissolved in methylene chloride and placed in the freezer. The diethoxycarbonylhydrazine was then filtered off and the filtrate was chromatographed on 400 ml silica, eluting with a 15 then 20% ethyl acetate/hexane. The appropriate fractions were bulked and stripped to give 3.98 g (72%) product which was used without further purification.

NMR (CDCl3), δ 1.48 (s, 18H), 3.31 (t, 2H, J=4 Hz), 4.45 (t, 2H, J=4 Hz), 5.47 (s, 1H), 6.96 (s, 1H), 7.03 (d, 2H, J=7 Hz), 7.73 (s, 2H), 7.83 (d, 2H, J=7 Hz), 9.88 (s, 1H).

G. Preparation of 2-(3,5-di-t-Butyl-4-hydroxyphenyl)-4-(2-(4-N-methyl-N-ethylaminomethylphenoxy)ethyl)thiazole Hydrochloride Hydrate N-methyl-N-ethylamine, 0.96 ml (11.26 mmole), and 3.33 ml (11.26 mmole) Ti(OPr)4 was dissolved in 20 ml of ethanol with stirring under nitrogen. The mixture was stirred for 10 minutes. The compound of Step F, 2.46 g (5.63 mmole) was added and the mixture was stirred for 2.5 hours. Sodium borohydride, 320 mg (8.44 mmole), was added and the reaction was stirred for 3.5 days. Ammonia, 7.85 ml 2N, was added to give a thick suspension then 55 ml of methylene chloride was added. Diatomaceous earth, 7.2 g, was added and the mixture was stirred and filtered through diatomaceous earth. The filtrate was washed twice with brine then dried and the organics were stripped and chromatographed, eluting with methylene chloride/methanol/concentrated ammonia 90:10:1. Fractions were combined, stripped and dissolved in methylene chloride/isopropyl ether. Hydrogen chloride gas was bubbled in and the product was concentrated and triturated with isopropyl ether to give 1.54 g (54%) white foam.

FDMS-M+480; Elemental Analysis for C₂₉H₄₀N₂O₂S.HCl.1.75 H₂O; Calculated: C, 63.48; H, 8.17; N, 5.11. Found: C, 63.55; H, 7.89; N, 4.86. NMR (CDCl3), δ 1.46 (t, 3H, J=4 Hz), 1.49 (m, 18H), 2.62 (d, 2H, J=4 Hz), 2.89 (m, 1H, J=4 Hz), 3.15 (m, 1H), 3.50 (bs, 2H), 4.10 (m, 2H), 4.41 (t, 2H, J=4 Hz), 5.75 (s, 1H), 6.96 (d, 2H, J=7 Hz), 7.12 (s, 1H), 7.50 (d, 2H, J=7 Hz), 7.90 (s, 2H).

EXAMPLE 39

E-2-(3,5-di-t-Butyl-4-hydroxyphenyl)-4-(3-(4-N-methyl-N-ethylaminomethylphenyl)-2-propenyl) oxazole Hydrochloride Hydrate A. Preparation of 4-(2-bromoethyl)-2-(3,5-di-t-butyl-4-hydroxyphenyl)oxazole To a stirred solution of triphenylphosphine (31.0 g, 118 mmole) in methylene chloride (394 ml) was added bromine (6.09 ml, 118 mmole). A small amount of additional triphenylphosphine was added to clear the solution. To this was added a mixture of the compound of Example 1C (25.0 g, 78.9 mmole) and imidazole (10.7 g, 158 mmole) dissolved in methylene chloride (315 ml) over 15 minutes. The reaction was allowed to stir at room temperature for 1 hour and was filtered. The filtrate was evaporated to dryness, triturated with methylene chloride/toluene, and filtered. This filtrate was chromatographed on silica gel using a hexane-ethyl acetate gradient to give the subtitled product (25.4 g, 85%):

1H NMR (CDCl3) δ 7.85 (s, 2H), 7.5 (s, 1H), 5.5 (s, 1H), 3.65 (t, J=6 Hz, 2H), 3.15 (t, J=6 Hz, 2H), 1.5 (s, 18H); FDMS 381 (M+).

B. Preparation of 2-(3,5-di-t-Butyl-4-hydroxyphenyl)-4-(2-triphenylphosphoniumethyl)oxazole Bromide To a stirred solution of 4-(2-bromoethyl)-2-(3,5-di-t-butyl-4-hydroxyphenyl)oxazole (25.4 g, 66.8 mmole) in xylenes (135 ml) was added triphenylphosphine (17.5 g, 66.81 mmole). The reaction was heated to reflux for 22 hours, and the xylene decanted from the precipitated product. The product was triturated in diethyl ether, filtered, and then triturated with ethyl acetate and filtered to give the intermediate phosphonium salt 2-(3,5-di-t-butyl-4-hydroxyphenyl)-4-(2-triphenylphosphonium ethyl)oxazole bromide (30.7 g, 72%):

1H NMR (CDCl3) δ 8.2 (bs, 1H), 7.8 (m, 17H), 5.5 (bs, 1H), 4.2 (bs, 2H), 3.1 (bs, 2H), 1.5 (s, 18H); FDMS 562 (M-Br+).

C. Preparation of E-2-(3,5-di-t-Butyl-4-hydroxyphenyl)-4-(3-(4-formylphenyl)-2-propenyl)oxazole Diethyl Acetal To a stirred solution of 2-(3,5-di-t-butyl-4-hydroxyphenyl)-4-(2-triphenylphosphonium ethyl)oxazole bromide (28.1 g, 43.8 mmole) in tetrahydrofuran (220 ml) was added terepthaldehyde mono-diethylacetal (8.68 ml, 43.8 mmole). This mixture was cooled to −10° C. and a 1M solution of sodium hexamethyldisilazane in tetrahydrofuran (87.5 ml, 87.5 mmole) was added dropwise over 8 minutes maintaining a temperature of less than 4° C. The reaction was stirred at 0° C. for 3 hours, quenched with water, and diluted with ethyl acetate and water. The pH was adjusted to 8.5 with 1N hydrochloric acid. The organic layer was extracted with brine, dried over sodium sulfate, evaporated to dryness, and chromatographed on silica gel using a hexane/acetone gradient to give the trans isomer of the olefin intermediate E-2-(3,5-di-t-butyl-4-hydroxyphenyl)-4-(3-(4-formylphenyl)-2-propenyl)oxazole diethyl acetal (2.6 g, 12%):

1H NMR (CDCl3) 7.85 (s, 2H), 7.4 (m, 5H), 6.55 (d, J=16 Hz, 1H), 6.4 (dt, J=16 Hz, 7 Hz, 1H), 5.5 (s, 1H), 5.45 (s, 1H), 3.5–3.6 (m, 6H), 1.5 (s, 18H), 1.25 (t, J=6 Hz, 6H); FDMS 491 (M+).

D. Preparation of Z-2-(3,5-di-t-Butyl-4-hydroxyphenyl)-4-(3-(4-formylphenyl)-2-propenyl)oxazole Diethyl Acetal Impure fractions from the above chromatography were rechromatographed on silica gel using a hexane-diethylether gradient to give the subtitled product (1.6 g, 7%):

1H NMR (CDCl3) 7.85 (s, 2H), 7.45 (d, J=8 Hz, 2H), 7.4 (s, 1H), 7.3 (d, J=8 Hz, 2H), 6.35 (d, J=11 Hz, 1H), 5.95 (dt, J=11 Hz, 7 Hz, 1H), 5.5 (s, 2H), 3.5–3.7 (m, 6H), 1.5 (s, 18H), 1.25 (t, J=6 Hz, 6H).

E. Preparation of E-2-(3,5-di-t-Butyl-4-hydroxyphenyl)-4-(3-(4-formylphenyl)-2-propenyl)oxazole To a stirred solution of the E-2-(3,5-di-t-butyl-4-hydroxyphenyl)-4-(3-(4-formylphenyl)-2-propenyl)oxazole diethyl acetal (2.53 g, 5.14 mmole) in diethyl ether (51 ml) was added 1N hydrochloric acid (51 ml), then concentrated hydrochloric acid (5.1 ml). The reaction was allowed to stir 18 hours, then basidified with saturated sodium bicarbonate. The organic layer was extracted with brine, dried over sodium sulfate, evaporated to dryness, and chromatographed on silica gel using a hexane-ethyl acetate gradient to give the desired product (1.19 g, 55%):

1H NMR (CDC13) 9.95 (s, 1H), 7.9 (s, 2H), 7.85 (d, J=8 Hz, 2H), 7.5 (d, J=8 Hz, 2H), 7.45 (s, 1H), 6.6 (m, 2H), 5.5 (s, 1H), 3.6 (d, J=5 Hz, 2H), 1.5 (s, 18H); FDMS 417 (M+).

F. Preparation of E-2-(3,5-di-t-Butyl-4-hydroxyphenyl)-4-(3-(4-N-methyl-N-ethylaminomethyl-phenyl)-2-propenyl) oxazole Hydrochloride To a stirred solution of ethylmethylamine hydrochloride (0.54 g, 5.7 mmole) in ethanol (5.8 ml) was added triethylamine (0.79 ml, 5.7 mmole), titanium tetraisopropoxide (1.68 ml, 5.7 mmole), and finally the E-2-(3,5-di-t-butyl-4-hydroxyphenyl)-4-(3-(4-formylphenyl)-2-propenyl)oxazole (1.19 g, 2.85 mmole) in ethanol (7.1 ml). The reaction was stirred for 4.5 hours, then sodium borohydride (0.16 g, 4.28 mmole) was added. After 20 hours at room temperature, the reaction was poured into 20 ml 2N ammonium hydroxide and diluted with methylene chloride. The mixture was filtered though diatomaceous earth and the filtrate was extracted with brine. The organic layer was dried over sodium sulfate, evaporated to dryness, and chromatographed on silica gel using a methylene chloride-methanol gradient to give the free base (0.79 g, 60%). The free base (0.79 g, 1.71 mmole) was dissolved in methylene chloride (17 ml), treated with hydrogen chloride gas, and evaporated to give desired product (0.83 g, 98%):

1H NMR (CDC13) δ 7.9 (s, 2H), 7.55 (d, J=9 Hz, 2H), 7.5 (d, J=9 Hz, 2H), 7.45 (s, 1H), 6.6 (d, J=16 Hz, 1H), 6.45 (dt, J=16 Hz, 7 Hz, 1H), 5.6 (s, 1H), 4.15 (m, 2H), 3.6 (d, J=7 Hz, 2H), 3.2 (m, 1H), 2.9 (m, 1H), 2.65 (d, J=5 Hz, 3H), 1.5 (m, 21H); FDMS 460 ($M^+$-HCl); Elemental Analysis for $C_{30}H_{41}ClN_2O_2$.1.5$H_2O$: Calculated: 68.75; H, 8.46; N, 5.34. Found: C, 69.06; H, 8.30; N, 5.49.

EXAMPLE 40

Z-2-(3,5-di-t-Butyl-4-hydroxyphenyl)-4-(3-(4-N-methyl-N-ethylaminomethylphenyl)-2-propenyl) oxazole Hydrochloride Monohydrate A. Preparation of Z-2-(3,5-di-t-Butyl-4-hydroxyphenyl)-4-(3-(4-formylphenyl)-2-propenyl)oxazole To a stirred solution of the compound of Example 39D (1.59 g, 3.23 mmole) in diethyl ether (32 ml) was added 1N hydrochloric acid (32 ml), then concentrated hydrochloric acid (3.2 ml). The reaction was allowed to stir 30 minutes, then basidified with saturated sodium bicarbonate. The organic layer was extracted with brine, dried over sodium sulfate, evaporated to dryness, and chromatographed on silica gel using a hexane-ethyl acetate gradient to give the desired subtitled product (8.15 g, 85%):

1H NMR (CDC13) 10.0 (s, 1H), 7.9 (d, J=8 Hz, 2H), 7.85 (s, 2H), 7.5 (d, J=8 Hz, 2H), 7.45 (s, 1H), 6.65 (d, J=11 Hz, 1H), 6.1 (dt, J=11 Hz, 7 Hz, 1H), 5.5 (s, 1H), 3.65 (d, J=7 Hz, 2H), 1.5 (s, 18H); FDMS 417 (M+).

B. Preparation of Z-2-(3,5-di-t-Butyl-4-hydroxyphenyl)-4 ((3-(4-N-methyl-N-ethylamninomethyl-phenyl)-2-propenyl)oxazole Hydrochloride To a stirred solution of ethylmethylaenine hydrochloride (0.78 g, 8.148 mmole) in ethanol (4.1 ml) was added triethylamine (1.14 ml, 8.18 mmole), titanium tetraisopropoxide (2.42 ml, 8.18 mmole), and finally the Z-2-(3,5-di-t-butyl-4-hydroxyphenyl)-4(3-(4-formylphenyl)-2-propenyl)oxazole (1.71 g, 4.09 mmole) in ethanol (10 ml). The reaction was stirred for 3.5 hours, then sodium borohydride (0.23 g, 6.14 mmole) was added. After 18 hours at room temperature, the reaction was poured into 30 ml 2N ammonium hydroxide and diluted with methylene chloride. The mixture was filtered though diatomaceous earth and the filtrate was extracted with brine. The organic layer was dried over sodium sulfate, evaporated to dryness, and chromatographed on silica gel using a methylene chloride-methanol gradient to give the free base (1.63 g, 86%). The free base (1.3 g, 2.82 mmole) was dissolved in methylene chloride (28 ml), treated with hydrogen chloride gas, and evaporated to give desired product (1.40 g, 100%):

1H NMR (CDC13) δ 8.05 (s, 2H), 7.6 (d, J=9 Hz, 2H), 7.5 (s, 1H), 7.35 (d, J=9 Hz, 2H), 6.65 (d, J=11 Hz, 1H), 6.05 (dt, J=11 Hz, 7 Hz, 1H), 5.8 (s, 1H), 4.15 (m, 2H), 3.75 (d, J=7 Hz, 2H), 3.2 (m, 1H), 2.95 (m, 1H), 2.7 (d, J=5 Hz, 3H), 1.5 (m, 21H); FDMS 460 (M+-HCl); Elemental Analysis for $C_{30}H_{41}ClN_2O_2$ $H_2O$: Calculated: 69.95; H, 8.41; N, 5.44. Found: C, 70.08; H, 8.10; N, 5.61.

EXAMPLE 41

2-(3,5-di-t-Butyl-4-hydroxyphenyl)-4-(3-(4-N-methyl-N-ethylaminomethylphenyl)propyl)oxazole Hydrochloride Hydrate To a stirred solution of Z-2-(3,5-di-t-butyl-4-hydroxyphenyl)-4-(3-(4-N-methyl-N-ethylaminomethylphenyl)-2-propenyl)oxazole (1.2 g, 2.6 mmole) in toluene (26 ml) was added 5% palladium on carbon (0.12 g). The suspension was subjected to 1 atmosphere hydrogen for 5 hours and filtered. The filtrate was evaporated to dryness and chromatographed on silica gel using a methylene chloride-methanol gradient to give the saturated free base (0.99 g, 82%). The free base (1.05 g, 2.27 mmole) was dissolved in methylene chloride (23 ml), treated with hydrogen chloride gas, evaporated, and triturated with diisopropyl ether to give desired product (1.00 g, 88%):

1H NMR ($CDCl_3$) δ 7.9 (s, 2H), 7.5 (d, J=9 Hz, 2H), 7.4 (s, 1H), 7.3 (d, J=9 Hz, 2H), 6.65 (d, J=11 Hz, 1H), 5.6 (s, 1H), 4.1 (m, 2H), 3.1 (m, 1H), 2.9 (m, 1H), 2.7 (t, J=7 Hz, 2H), 2.65 (m, 5H), 2.05 (m, 2H), 1.5 (m, 21H); FDMS 462 (M+-HCl); Elemental Analysis for $C_{30}H_{43}ClN_2O_2$.1.5$H_2O$: Calculated: 68.48; H, 8.81; N, 5.32. Found: C, 68.40; H, 8.63; N, 5.22.

EXAMPLE 42

2-(3,5-di-tert-Butyl-4-hydroxyphenyl))-4-((4-N-methyl-N-ethylaminomethyl)phenoxymethyl) oxazole Hydrochloride A. N-Carbo(3,5-di-t-butyl-4-hydroxy)phenyl-DL-serine Methyl Ester.

To a suspension of benzoic acid in tetrahydrofuran (165 ml) was added in portions over a 20 minute period, 1,1'-carbonyldiimidazole. The resulting gold solution was stirred at 22° C. for twenty minutes then added dropwise to the solution described below.

To a suspension of DL-serine methyl ester in tetrahydrofuran (115 ml) was added diisopropyl ethyl amine followed by dimethyl formamide (70 ml). The resulting colorless solution was stirred at 22° C. for one hour then the activated benzoic acid derivative (described above) was added. The reaction was stirred at 22° C. for 5 days then concentrated in vacuo to an oil. The oil was treated with ethyl acetate (250 ml) and washed with three times with 1:1 brine:0.1N hydrochloric acid, and one time with brine. The organics were dried over sodium chloride, warmed on a steam bath, filtered hot, and the filtrate was concentrated in vacuo to an oil. The oil was then treated with 1:1 hexane:ethyl acetate, reduced in volume on a steam bath to approximately 250 ml then sonicated. The mixture was cooled to −20° C. for approximately 2 hours resulting in crystal formation. Crystals were collected by filtration, washed with 70% hexane:ethyl acetate to afford 49.13 g of the title compound. The filtrate was concentrated in vacuo to an oil. The oil was treated with 1:1 hexane:ethyl acetate then subjected to prepatory chromatography eluting with 50 to 70% hexane:ethyl acetate over a thirty-minute period. Desired fractions containing title compound were combined and concentrated in vacuo to an oil. The title compound was recrystallized from diethyl ether:hexane to afford 11.32 g of the title compound. A total of 60.45 g (56%) of the title compound was isolated.

mp (° C): 108–109 Mass Spectrum (FDMS): m/z 351 (M). 1H NMR (CdCL3): δ 7.65 (s, 2H), 6.99 (d, J=6.2 Hz, 1H), 5.60 (s, 1H), 4.85 (dt, J=3.6 Hz, 1H), 4.06 (bs, 2H), 3.83 (s, 3H), 1.45 (s, 18H). Elemental Analysis for $C_{19}H_{29}NO_5$: Calculated: C, 64.94; H, 8.32; N, 3.99. Found: C, 65.20; H, 8.42; N, 4.22.

B. 4-((RS)Carbomethoxy)-2-(3,5-di-tert-butyl-4-hydroxyphenyl))-2-oxazoline

To a suspension of N-carbo(3,5-di-t-butyl-4-hydroxy) phenyl-DL-serine methyl ester (0.17 mole, 58.81 g) and imidazole (0.18 mole, 12.53 g) in acetonitrite (890 ml) at 22° C. was added triphenylphosphine (0.18 mole, 48.28 g) followed by carbon tetrabromide (0.18 mole, 61.05 g). After stirring 2.5 hours, the reaction was concentrated in vacuo to a foam that contains crystalline material. The mixture was treated with ethyl acetate:hexane (100 ml), then cooled to −20° C. The insolubles were collected by filtration and discarded. The filtrate was subjected to preparatory chromatography, eluting with a gradient of 25 to 40% ethyl acetate:hexane over a 30-minute period. Fractions containing the title compound plus a coeluting impurity were resubjected to prepatory chromatography, eluting with 15 to 35% ethyl acetate:hexane over 30 minutes. Fractions containing the title compound were combined, concentrated in vacuo to afford 55.75 g (99%) of an oil that slowly crystallizes.

mp (° C): 102–104 Mass Spectrum (FDMS): m/z 333 (M) $^1$H NMR ($CDCl_3$): δ 7.80 (s, 2H), 5.59 (s, 1H), 4.91 (dd, J=7.6, 10.4 Hz, 1H), 4.73 (dd, J=7.6, 8.6 Hz, 1H), 4.53 (dd, J=8.6, 10.4 Hz, 1H), 3.80 (s, 3H), 1.45 (s, 18H). Elemental analysis for $C_{19}H_{27}NO_4$: Calculated: C, 68.44; H, 8.16; N, 4.20. Found: C, 68.33; H, 8.10; N. 4.34.

C. 4-(Carbomethoxy)-2-(3,5-di-tert-butyl-4-hydroxyphenyl)oxazole

A solution of ((RS)-4-carbomethyoxy)-2-(3,5-di-tert-butyl-4-hydroxypentyl))-2-oxazoline (0.66 mole, 220.15 g) in acetone (1.6 L) was treated with activated manganese oxide (6.60 mole, 574.0 g). The suspension was stirred at 22° C. for 17.5 hours then heated at 45° C. for one hour. Diatomaceous earth (250 ml) was added to the reaction, then the suspension was filtered through a pad of silica (2.5 cm×14.5 cm) and diatomaceous earth (250 g). The insolubles were rinsed with acetone until no product was observed in the filtrate by thin layer chromatography. The filtrate was concentrated in vacuo to afford 303.5 g of a black solid. The material was treated with diethyl ether (500 ml), and placed on a steam bath until the solid dissolved, then hexane was added (250 ml). The solution was boiled down until crystals formed. The mixture was cooled to 22° C., crystals were collected by filtration and washed with 2:1 hexane:diethyl ether to afford 98.1 g of the title compound that contains an impurity. This material was subjected to multi-recrystallizations as described above to afford 92.46 g of the title compound. Additional title compound was isolated by multiple recrystallizations of the filtrates to afford 36.94 g.

The filtrate from the crystallization was concentrated in vacuo to a solid then recrystallized as described above to afford 43.46 g of the title compound. The filtrate was concentrated in vacuo to a solid. The solid was treated with methylene chloride then divided into two lots. Each lot was subjected to preparatory chromatography eluting with 5 to 25% ethyl acetate:hexane over a 30-minute period. Fractions containing the title compound plus a coeluting impurity were combined and concentrated in vacuo to afford a black solid. This solid was recrystallized as described above to afford 20.74 g of a yellow/green solid. The solid was then triterated in boiling 1:4 ethyl acetate:hexane (200 ml), filtered hot and washed with 1:4 ethyl acetate:hexane to afford 17.99 g of the title compound. Additional title compound was recrystallized from the filtrate to afford 0.65 g. A total of 148.04 g (68%) of the title compound was isolated.

mp (° C): 163 Mass Spectrum (FDMS): m/z 331 (M). $^1$H NMR ($CDCl_3$): δ 8.23 (s, 1H), 7.91 (s, 2H), 5.59 (s, 1H), 3.94 (s, 3H), 1.48 (s, 18H). Elemental Analysis for $C_{19}H_{25}NO_4$: Calculated: C, 68.86; H, 7.60; N, 4.23. Found: C, 69.11; H, 7.72; N, 4.21.

D. (4-(Hydroxymethyl)-2-(3,5-di-tert-butyl-4-hydroxyphenyl))-2-oxazole.

A dark blue solution of 4-(carbomethoxy)-2-(3,5-di-tert-butyl-4-hydroxyphenyl))-2-oxazole (0.39 mole, 127.71 g) in tetrahydrofuran (2.6 L) and a 3 neck 12 L flask was treated with methanol (0.58 mole, 23.4 ml). Next, lithium borohydride. (0.58 mole, 12.59 g) was added carefully over a 60 minute period. During this addition, the reaction was cooled with an ice bath to maintain temperature between 19 and 24° C. Once the borohydride addition was complete, the orange colored reaction was slowly bought to reflux (ca. 50 minutes). After refluxing for 4.5 hours, the bright yellow colored reaction was cooled to 22° C. The reaction was then carefully treated with 5N hydrochloric acid (620 ml) over a thirty-minute period. Vigorous gas evolution was observed during the addition of the first 40 ml of hydrochloric acid. Ethyl acetate (1 L) was added and the reaction was divided into two lots. Each lot was treated with water (500 ml) and the phases were separated. The aqueous phases were combined and extracted twice with ethyl acetate. The organic phases were combined and concentrated in vacuo to an oil. Diethyl ether (500 ml) was added to the oil, reduced in volume on a steam bath to approx. 500 ml, then cooled to −78° C. (using dry ice/acetone) for one hour. After warming to 22° C. the resulting crystals were collected by filtration and washed with diethyl ether to afford 56.55 g of the title compound. Subsequent recrystallizations of the filtrate afforded an additional 52.76 g. A total of 109.31 g (94%) of the title compound was isolated.

mp (° C): 150 Mass Spectrum (FDMS): m/z 303 (M). 1H NMR (CdCL3): δ 8.33 (s, 2H), 7.68 (s, 1H), 6.12 (s, 1H), 4.80 (s, 2H), 1.51 (s, 18H). Elemental Analysis for $C_{18}H_{25}NO_3$: Calculated: C, 71.26; H, 8.31; N, 4.62. Found: C, 71.52; H, 8.26; N, 4.79.

E. 4-(bromomethyl)-2-(3,5-di-tert-butyl-4-hydroxyphenyl) oxazole.

A suspension of 4-(hydroxymethyl)-2-(3,5-di-tert-butyl-4-hydroxyphenyl) oxazole (44.2 mmole, 13.41 g) in acetonitrile (230 ml) was treated with triphenylphosphine (53.0 mmole, 13.91 g) followed by carbon tetrabromide (53.0 mmole, 17.59 g). The resulting solution was stirred at approximately 22° C. for 3 hours. Next, additional carbon tetrabromide (22.0 mmole, 13.13 g) and triphenylphosphine 22.0 mmole, 5.79 g) was added to the reaction. After stirring for an additional 40 minutes, the reaction was quenched with water (5 mL), stirred 10 minutes and concentrated in vacuo and stored at 5° C. for approximately 16 hours. The material was then taken up into chloroform and subjected to prepatory chromatography eluting with 35 to 50% chloroform-:hexane over a thirty-minute period. Fractions containing title compound were combined, dried over sodium sulfate, filtered, concentrated in vacuo to afford 9.7 g of the title compound that crystallized out upon standing at 22° C.

mp (° C): Mass Spectrum (FDMS): m/z 367 (M+1). 1H NMR (CdCL3): δ 7.84 (s, 2H), 7.65 (s, 1H), 5.53 (s, 1H), 4.44 (s, 2H), 1.48 (s, 18H). Elemental Analysis for: $C_{18}H_{24}BrNO_2$ Calculated: C, 59.02; H, 6.60; N, 3.82. Found: C, 58.83; H, 6.53; N, 3.85.

F. 4-(4-(2-Formyl)phenoxymethyl)-2-(3,5-di-tert-butyl-4-hydroxyphenyl))oxazole.

A suspension of 4-(bromomethyl)-2-(3,5-di-tert-butyl-4-hydroxyphenyl)oxazole (26.5 mmole, 9.70 g), 4-hydroxybenzaldehyde (29.1 mmole, 3.56 g), potassium carbonate (79.4 mmole, 10.97 g) and potassium iodide (26.5 mmole, 4.39 g) in methyl ethyl ketone (275 ml) was refluxed for 2 hours. The reaction was then cooled to approximately 22° C., filtered, concentrated in vacuo to an oil. The oil was treated with ethyl acetate (250 ml) then washed twice with saturated aqueous sodium bicarbonate, once with aqueous sodiumbisulfate and once with brine. The organic layer was dried over sodium sulfate, filtered, and concentrated in vacuo to an oil. The material was taken up into ethyl acetate, then subjected to prepatory chromatography eluting with 30 to 50 ethyl acetate:hexane over a thirty-minute period. Fractions containing title compound plus impurities were resubjected to prepatory chromatography eluting with 25 to 35% acetone:hexane over a thirty-minute period. Fractions containing title compound were combined and concentrated in vacuo to afford 8.9 g (82%).

mp 160 (° C): Mass Spectrum (FDMS): m/z 1H NMR (CdCL3): δ 9.90 (s, 1H), 7.85 (d, 4H), 7.69 (s, 1H), 7.12 (d, 2H), 5.54 (s, 1H), 5.14 (s, 2H), 1.49 (s, 18H). Elemental Analysis for: $C_{25}H_{29}NO_4$ Calculated: C, 73.69; H, 7.17; N, 3.44. Found: C, 73.72; H, 7.16; N, 3.45.

G. 2-(3,5-di-tert-Butyl-4-hydroxyphenyl))-4-((4-N-methylethylaminomethyl)phenoxymethyl)oxazole Hydrochloride The title compound was prepared substantially as described in Example 11, except using 4-(4-(2-formyl) phenoxymethyl)-2-(3,5-di-tert-butyl-4-hydroxyphenyl)) and N-methyl-n-ethylamine. The crude material was subjected to Prepare chromatography eluting with 0 to 10% (methanol:ammonium hydroxide):chloroform over a 30-minute period. Fractions containing title compound were combined and concentrated in vacuo to afford 6.0 g. The material was dissolved in diethyl, ether (100 ml) then saturated with hydrochloric gas. The resulting precipitate was collected by filtration and washed with diethyl ether. This material was dissolved in methylene chloride (50 ml) and washed with 0.1N ammoniumhydroxide (50 ml). The organic layer was dried over sodium sulfate then filtered. The filtrate was subjected to preparatory chromatography eluting with 0 to 10% (methanol:ammonium hydroxide) :chloroform. Fractions containing title compound combined, concentrated in vacuo to a foam. The foam was treated with diethyl ether (100 ml) and saturated aqueous sodium bicarbonate (100 ml). The phases were separated, aqueous phase extracted with diethyl ether (1×50 ml). The organic phases were combined, dried over sodium sulfate, filtered, then slowly added to a saturated solution of hydrogen chloride diethyl ether. The resulting suspension was concentrated in vacuo to afford 4.74 g of the title compound as a foam.

Mass Spectrum (FDMS): m/z 450 (M-HCl) $^1$H NMR ($CDCl_3$): δ 7.86 (s, 2H), 7.68 (s, 1H), 7.52 (d, J=8.6 Hz, 2H) 7.06 (d, J=8.6 Hz, 2H), 5.54 (s, 1H), 5.07 (s, 2H), 4.10 (M, 2H), 3.17 (m, 1H), 2.91 (m, 1H), 2.64 (d, J=5.0 Hz, 3H), 1.48 (m, 21H). Elemental Analysis for: $C_{28}H_{39}ClN_2O_3$ Calculated: C, 69.05; H, 8.07; N, 5.75. Found: C, 68.95; H, 7.98; N, 5.76.

EXAMPLE 43

2-(3,5-di-t-Butyl-4-hydroxyphenyl)-4-((4-N-ethyl-N-propylaminoethylphenoxy)methyl)oxazole Hydrochloride A. 2-(3,5-di-t-Butyl-4-hydroxyphenyl)-4-((4-N-ethyl-N-propionylaminoethylphenoxy)methyl)oxazole To a stirred solution of N-ethyl,N-propionyl tyramine (2.84 g, 12.83 mmole) in tetrahydrofuran (32.1 ml) was added 60% sodium hydride dispersion (0.56 g, 14.11 mmole). After stirring for 10 minutes, the compound of Example 42(E) (4.70 g, 12.83 mmole) was added. The reaction was allowed to stir at room temperature for 5 hours, poured into ethyl acetate, and extracted with 10% sodium sulfate, then brine. The organic layer was dried over sodium sulfate, evaporated to dryness, and chromatographed on silica gel using a hexane-ethyl acetate gradient. Further chromatography on silica gel using toluene-acetone gradients yielded the intermediate phenyl ether (2.10 g, 32%):

$^1$H NMR ($CDCl_3$) (2 rotamers) δ 7.9 (s, 2H), 7.65 (s, 1H), 7.15 (d, J=9 Hz, 1H), 7.1 (d, J=9 Hz, 1H), 6.95 (m, 2H), 5.55 (s, 1H), 5.05 (s, 2H), 3.1–3.5 (m, 4H), 2.8 (m, 2H), 2.15–2.4 (m, 2H), 1.5 (m, 18H), 1.05–1.2 (m, 6H).

B. 2-(3,5-di-t-Butyl-4-hydroxyphenyl)-4-((4-ethylpropylaminoethylphenoxy)methyl)oxazole Hydrochloride To a stirred solution of the intermediate phenyl ether prepared above (1.87 g, 3.69 mmole) in tetrahydrofuran (55 ml), was added 2M borane-dimethylsulfide in tetrahydrofuran (5.9 ml, 11.81 mmole). The reaction was heated to reflux for 3 hours, and evaporated to dryness. After redissolving in methanol, 0.99M hydrochloric acid in methanol (5.0 ml) was added. The reaction was heated to 60° C. for 18 hours. After cooling to room temperature, the pH was adjusted to 8.5 with 1N sodium hydroxide, and the solvent was evaporated. The residue was dissolved in ethyl acetate and saturated sodium bicarbonate. The organic layer was washed with brine, dried over sodium sulfate, evaporated to dryness, and chromatographed on silica gel using a methylene chloride-methanol gradient to give the free base (1.20 g, 66%). The free base (1.31 g, 2.66 mmole) was dissolved in methylene chloride (40 ml), treated with hydrochloric acid, and evaporated to give desired product (1.43 g, 100%):

$^1$H NMR ($CDCl_3$) δ 7.85 (s, 2H), 7.6 (s, 1H), 7.15 (d, J=9 Hz, 2H), 6.95 (d, J=9 Hz, 2H), 5.55 (s, 1H), 5.05 (s, 2H, 3.1 (m, 6H), 2.95 (m, 2H), 1.85 (m, 2H), 1.5 (m, 18H), 1.4 (t, J=7 Hz, 3H), 1.0 (t, J=7 Hz, 3H); FDMS 492 ($M^+$-HCl); Elemental analysis for $C_{31}H_{45}ClN_2O_3.0.6H_2O$: Calculated: C, 68.96; H, 8.62; N, 5.19. Found: C, 68.76; H, 7.40; N, 5.25.

EXAMPLE 44

2-(3,5-di-t-Butyl-4-hydroxyphenyl)-4-(3-(4-N-methyl-N-ethylaminomethylphenyloxy)propyl)oxazole A. 2-(3,5-di-t-Butyl-4-hydroxyphenyl)-4-(3-hydroxypropyl)oxazole To a stirred solution of 2-(3,5-di-t-butyl-4-hydroxyphenyl)-4-(2-formylethyl)oxazole (Example 43C) (9.01 g, 27.3 mmole) in diethylether (270 ml) was added sodium borohydride (1.03 g, 27.3 mmole) in water (90 ml). After stirring for 3 days, the reaction mixture was poured into diethylether, and extracted with 1N hydrochloric acid, then brine. The organic layer was dried over sodium sulfate and evaporated to dryness, to yield the intermediate primary alcohol (9.2 g, 100%):

$^1$H NMR ($CDCl_3$) δ 7.8 (s, 2H), 7.4 (s, 1H), 5.5 (s, 1H), 3.8 (m, 18H); FDMS 331 ($M^+$).

B. 2-(3,5-di-t-Butyl-4-hydroxyphenyl)-4-(3-(4-formylphenyloxy)propyl)oxazole

To a stirred solution of the intermediate primary alcohol prepared above (9.1 g, 27.45 mmole) in tetrahydrofuran (82 ml) was added 4-hydroxybenzaldehyde (3.68 g, 30.20 mmole) and triphenylphosphine (7.91 g, 30.20 mmole). After cooling to −20° C., a solution of diethylazodicarboxylate (4.75 ml, 30.20 mmole) in tetrahydrofuran (27 ml) was added dropwise over 30 minutes. The reaction was allowed to warm to room temperature and stir for 18 hours, at which time it was diluted with diethylester and extracted with water, 1N sodium hydroxide, and brine. The organic layer was dried over sodium sulfate, evaporated to dryness, and chromatographed on silica gel using a hexane-acetone gradient to give the intermediate aldehyde (7.7 g, 64%):

$^1$H NMR ($CDCl_3$) δ 9.9 (s, 1H), 7.85 (d, J=9 Hz, 2H), 7.85 (s, 2H), 7.4 (s, 1H), 7.0 (d, J=9 Hz, 1H), 5.55 (s, 1H), 4.15 (t, J=7 Hz, 2H), 2.8 (t, J=7 Hz, 2H), 2.2 (m, 2H), 1.5 (s, 18H); FDMS 435 ($M^+$).

C. 2-(3,5-di-t-Butyl-4-hydroxyphenyl)-4-(3-(4-methylethylaminomethyl-phenyloxy)propyl)oxazole Hydrochloride To a stirred solution of the intermediate aldehyde prepared above (2.8 g, 6.43 mmole) in dichtoroethane (22 ml), was added N-ethyl-N-methyl amine (0.55 ml, 6.43 mmole) and sodium triacetoxyborohydride (3.81 g, 18.0 mmole). After 20 hours, the reaction was quenched with saturated sodium bicarbonate and diluted with ethyl acetate. The organic layer was extracted with brine, dried over sodium carbonate, evaporated to dryness, and chromatographed on silica gel using a methylene chloride-methanol gradient to give the free base (2.38 g, 77%). The free base was dissolved in methylene chloride (70 ml), treated with hydrochloric acid, and evaporated to give desired product (2.4 g, 94%):

$^1$H NMR ($CDCl_3$) δ 7.9 (s, 2H), 7.5 (d, J=9 Hz, 2H), 7.4 (s, H), 6.95 (d, J=9 Hz, 2H), 5.6 (s, 1H), 4.1 (m, 2H), 4.05 (t, J=7 Hz, 2H), 3.2 (m, 1H), 2.9 (m, 1H), 2.8 (t, J=7 Hz, 2H), 2.6 (d, J=4 Hz, 3H), 2.2 (m, 2H), 1.5 (s, 18H); FD MS 478 ($M^+$-HCl); Elemental analysis for $C_{30}H_{43}ClN_2O_3.0.5H_2O$: Calculated: C, 68.75; H, 8.46; N, 5.34. Found: C, 68.93; H, 8.34; N, 5.17.

EXAMPLE 45

2-(3,5-Dimethoxy-4-hydroxyphenyl)-4-(2-(4-methylethylaminomethyl-phenyloxy)ethyl)oxazole A. 4-Benzyloxy-3,5-dimethyoxybenzamide To a stirred solution of 4-benzyloxy-3,5-dimethoxy benzoic acid (23.4 g, 81.2 mmole) in tetrahydrofuran (325 ml) was added carbonyldiimidazole (14.46 g, 89.3 mmole). After refluxing for 2 hours, the reaction was allowed to cool to room temperature and ammonium hydroxide (81 ml) was added. The reaction was allowed to stir at room temperature for 1.5 hours, diluted with ethyl acetate, then acidified with 1N hydrochloric acid. The organic layer was extracted with saturated sodium bicarbonate, then brine. The organic layer was dried over sodium sulfate and evaporated to dryness, to yield the intermediate benzamide (22.8 g, 98%):

$^1$H NMR ($CDCl_3$) δ 7.45 (d, J=9 Hz, 2H), 7.35 (m, 3H), 7.0 (s, 2H), 6.0 (bs, 2H), 5.05 (s, 2H), 3.85 (s, 6H); FD MS 287 ($M^+$).

B. 2-(4-Benzyloxy-3,5-dimethyoxyphenyl)-4-(ethylacetate) oxazole

A stirred suspension of the intermediate benzamide (22.8 g, 79.35 mmole) in 4-chloroacetoactetate (47.6 ml 352 mmole) was heated to 130° C. for 2 hours with azeotropic removal of water. The reaction was then poured into ethyl acetate and the resulting suspension was filtered. The filtrate was extracted with water, saturated sodium bicarbonate, 1N hydrochloric acid, then brine. The organic layer was dried over sodium sulfate, evaporated to dryness, and distilled to remove 4-chloroacetoactetate. The distillation pot was triturated with methylene chloride, filtered, and the filtrate was chromatographed on silica gel using a hexane-ethyl acetate gradient to give the intermediate ethyl ester (11.7 g, 37%):

$^1$H NMR ($CDCl_3$) δ 7.7 (s, 1H), 7.5 (d, J=9 Hz, 2H), 7.35 (m, 3H), 7.25 (s, 2H), 5.1 (s, 2H), 4.2 (q, J=7 Hz, 2H), 3.85 (s, 6H), 3.65 (s, 2H), 1.3 (t, J=7 Hz, 3H); MS 398 ($M^+$+1).

C. 2-(4-Benzyloxy-3,5-dimethoxyphenyl)-4-(2-hydroxyehtyl)oxazole

To a stirred solution of the intermediate ethyl ester (11.7 g, 29.44 mmole) in tetrahydrofuran (200 ml) was added 1M lithium aluminum hydride in tetrahydrofuran (26.5 ml, 26.5 mmole) dropwise over 10 minutes. After an additional 30 minutes, the reaction was quenched with dropwise addition of water (1.0 ml), 15% sodium hydroxide (1.0 ml), then water again (3.0 ml). The insolubles were filtered and washed with ethyl acetate. The filtrate was extracted with 1N hydrochloric acid, then brine. The organic layer was dried over sodium sulfate, evaporated to dryness, and chromatographed on silica gel using a hexane-acetone gradient to give the intermediate primary alcohol (7.9 g, 76%):

$^1$H NMR ($CDCl_3$) δ 7.5 (s, 1H), 7.45 (d, J=9 Hz, 2H), 7.35 (m, 3H), 7.25 (s, 2H), 5.1 (s, 2H), 3.95 (m, 2H), 3.9 (s, 6H), 3.85 (m, 2H); MS 355 ($M^+$).

D. 2-(4-Benzyloxy-3,5-dimethoxyphenyl)-4-(2-(4-formylphenyloxy)ethyl)oxazole

To a stirred solution of the of the intermediate primary alcohol (7.9 g, 22.22 mmole) in tetrahydrofuran (67 ml) was added 4-hydroxybenzaldehyde (2.98 g, 24.44 mmole) and triphenylphosphine (6.41 g, 24.44 mmole). After cooling to −20° C., a solution of diethylazodicarboxylate (3.85 ml, 24.44 mmole) in tetrahydrofuran (22 ml) was added dropwise over 26 min. The reaction was allowed to warm to room temperature and stir for 18 hours, at which time it was diluted with diethylether and extracted with water, 1N sodium hydroxide, and brine. The organic layer was dried over sodium sulfate, evaporated to dryness, and chromatographed on silica gel using a methylene chloride-ethyl acetate gradient to give the intermediate aldehyde (7.9 g, 77%):

$^1$H NMR ($CDCl_3$) δ 9.9 (s, 1H), 7.85 (d, J=9 Hz, 2H), 7.55 (s, 1H), 7.45 (d, J=9 Hz, 2H), 7.3 (m, 3H), 7.25 (s, 2H), 7.0 (d, J=9 Hz, 2H), 5.1 (s, 1H), 4.4 (t, J=7 Hz, 2H), 3.9 (s, 6H), 3.1 (t, J=7 Hz, 2H); MS 460 ($M^+$+1).

E. 2-(4-Benzyloxy-3,5-dimethoxyphenyl)-4-(2-(4-methylethylaminomethyl-phenyloxy)ethyl)oxazole To a stirred solution of the intermediate aldehyde (5.3 g, 11.53 mmole) in dichloroethane (40 ml) was added ethyl, methyl amine (0.99 ml, 11.53 mmole) and sodium triacetoxyborohydride (6.84 g, 32.28 mmole). After 20 hours, the reaction was quenched with saturated sodium bicarbonate and diluted with ethyl acetate. The organic layer was extracted with brine, dried over sodium sulfate, evaporated to dryness, and chromatographed un silica gel using a methylene chloride-methanol gradient to give the intermediate benzyl amine (4.9 g, 84%):

$^1$H NMR ($CDCl_3$) δ 7.65 (s, 1H), 7.5 (d, J=9 Hz, 2H), 7.35 (m, 3H), 7.25 (s, 2H), 7.2 (d, J=9 Hz, 2H), 6.85 (d, J=9 Hz, 2H), 5.05 (s, 2H), 4.25 (t, J=7 Hz, 2H), 3.9 (s, 6H), 3,4 (s, 2H), 3.1 (t, J=7 Hz, 2H), 2.45 (q, J=7 Hz, 2H), 2.2 (s, 3H), 1.1 (t, J=7 Hz, 3H); MS 502 ($M^+$).

F. 2-(3,5-Dimethoxy-4-hydroxyphenyl)-4-(2-(4-methylethylaminomethyl-phenyloxy)ethyl)oxazole Hydrochloride To a stirred solution of the intermediate benzyl amine prepared above (4.4 g, 8.75 mmole) in methanol (175 ml) was added concentrated hydrochloric acid (175 ml). The reaction was heated to 70° C. for 1 hour, allowed to cool to room temperature, neutralised with sodium bicarbonate, and extracted with ethyl acetate. The organic layer was extracted with brine, dried over sodium sulfate, evaporated to dryness, and chromatographed on silica gel using a methylene chloride-methanol gradient to give the free base (2.8 g, 70%). The free base was dissolved in methylene chloride (75 ml), treated with hydrochloric acid, and $^1$H NMR ($CDCl_3$) δ 7.6 (s, 1H), 7.55 (d, J=9 Hz, 2H), 7.4 (s, 2H), 6.95 (d, J=9 Hz, 2H), 4.35 (t, J=7 Hz, 2H), 4.1 (m, 2H), 3.95 (s, 6H), 3.15 (m, 3H), 2.9 (m, 1H), 2.65 (d, J=4 Hz, 3H), 1.5 (t, J=7 Hz, 2H); MS 413 ($M^+$-HCl+1); Elemental analysis for $C_{23}H_{29}ClN_2O_5.1.5H_2O$: Calculated: C, 57.98; H, 6.94; N, 5.62. Found: C, 58.04; H, 6.78; N, 5.89.

EXAMPLE 46

2-(3,5-di-t-Butyl-4-hydroxyphenyl)-4-(2-(4-(2-methylthioethyl)methylaminomethyl-phenyloxy)ethyl)oxazole Hydrochloride To a stirred solution of 2-(3,5-di-t-butyl-4-hydroxyphenyl)-4-2-(4-methyl)amino methylphenyloxy) ethyl)oxazole (8.06 g, 18.48 mmole) in dimethylformamide (46 ml) was added 60% sodium hydride dispersion (1.77 g, 44.35 mmole). After 20 minutes of stirring, 2-chloroethyl methyl sulfide (1.84 ml, 18.48 mmole) was added. The reaction was heated to 80° C. for 7.5 hours, with more chloroethyl methyl sulfide (1.84 ml, 18.48 mmole) added at 2.5 and 5 hours. The reaction was quenched with water and diluted with ether and saturated sodium bicarbonate. The aqueous layer was extracted with ethyl acetate and the combined organics were extracted with brine. The organic layer was dried over sodium sulfate, evaporated to dryness, and chromatographed on silica gel using a hexane-acetone gradient to give the free base (4.6 g, 46%). The free base (1.00 g, 1.96 mmole) was dissolved in methylene chloride (20 ml), treated with hydrochloric acid, and evaporated to give desired product (1.09 g, 100%):

$^1$H NMR ($CDCl_3$) δ 8.0 (s, 2H), 7.6 (s, 1H), 7.5 (d, J=9 Hz, 2H), 7.0 (d, J=9 Hz, 2H), 5.7 (s, 1H), 4.35 (t, J=7 Hz, 2H), 4.15 (m, 2H), 2.9–3.3 (m, 6H), 2.65 (s, 3H), 2.15 (s, 3H), 1.5 (s, 18H). FD MS 511 ($M^+$-HCl+1); Elemental analysis for $C_{30}H_{43}ClN_2O_3S.0.7H_2O$: Calculated: C, 64.37; H, 7.99; N, 5.00. Found: C, 64.25; H, 7.83; N, 4.74.

EXAMPLE 47

2-(3,5-di-t-Butyl-4-hydroxyphenyl)-4-(2-(4-(2-methylthioethyl)methylaminomethyl-phenyloxy)ethyl)oxazole, S-oxide Hydrochloride To a stirred solution of the free base prepared for 2-(3,5-di-t-butyl-4-hydroxyphenyl)-4-(2-(4-(2-methylthioethyl) methylaminomethyl-phenyloxy)ethyl)oxazole (1.8 g, 3.52 mmole) in methylene chloride (18 ml) was added 55% m-chloroperbenzoic acid (1.11 g, 3.52 mmole) in methylene chloride (11 ml) at 0° C. over 10 minutes. After stirring at 0° C. for 1.5 hours, the reaction was diluted with methylene chloride and extracted with saturated sodium bicarbonate. The organic layer was extracted with brine, dried over sodium sulfate, evaporated to dryness, and chromatographed on silica gel using a chloroform-ethanol gradient to give the free base (0.79 g, 43%). The free base (0.78 g, 1.46 mmole) was dissolved in methylene chloride (15 ml), treated with hydrochloric acid, and evaporated to give desired product (0.80 g, 96%):

$^1$H NMR ($CDCl_3$) δ 7.9 (s, 2H), 7.5 (m, 3H), 7.0 (d, J=9 Hz, 2H), 5.6 (s, 1H), 4.3 (t, J=7 Hz, 2H), 4.2 (m, 2H), 3.2–3.8 (m, 4H), 3.15 (t, J=7 Hz, 2H), 2.7 (m, 6H), 1.5 (s, 18H); FDMS 526 ($M^+$-HCl); Elemental analysis for $C_{30}H_{43}ClN_2O_4S.1.1H_2O$: Calculated: C, 61.80; H, 7.81; N, 4.80. Found: C, 61.55; H, 7.50; N, 4.55.

EXAMPLE 48

2-(3,5-di-t-Butyl-4-hydroxyphenyl)-4-(2-(4-ethylpropylaminoethylphenoxy)ethyl)oxazole A. N-ethyl,N-propionyl Tyramine To a stirred solution of carbonyldiimidazole (14.13 g, 87.12 mmole) in tetrahydrofuran (109 ml) at 5° C., was added dropwise a solution of propionic acid (6.5 ml, 87.12 mmole) in tetrahydrofuran (73 ml) over 30 minutes. After stirring for 20 minutes, N-ethyl tyramine (12.0 g, 72.6 mmole) in tetrahydrofuran (73 ml) was added over 20 minutes. The reaction was allowed to warm to room temperature and stir for 4 hours. Methanol (7.3 ml) was added and stirring was continued for 30 minutes. The reaction was worked up by diluting with ethyl acetate and extracting with 1N hydrochloric acid, saturated sodium bicarbonate, then brine. The organic layer was dried over sodium sulfate, evaporated to dryness, and chromatographed on silica gel using a methylene chloride-methanol gradient to give N-ethyl,N-propionyl tyramine (6.95 g, 43%):

$^1$H NMR ($CDCl_3$) (2 rotamers) δ 7.65 (bs, 0.5H), 7.25 (bs, 0.5H), 7.05 (d, J =9 Hz, 1H), 7.0 (d, J=9 Hz, 1H), 6.8 (d, J=9 Hz, 2H), 3.2–3.6 (m, 4H), 2.8 (m, 2H), 2.4 (q, J=7 Hz, 1H), 2.05 (q, J=7 Hz, 1H), 1.0–1.2 (m, 6H). FD MS 221 ($M^+$).

B. 2-(3,5-di-t-Butyl-4-hydroxyphenyl)-4-(2-(4-N-ethyl-N-propionylaminoethylphenoxy)ethyl)oxazole To a stirred solution of 2-(3,5-di-t-butyl-4-hydroxyphenyl)-4-(2-hydroxyethyl)oxazole (5.51 g, 17.38 mmole) in tetrahydrofuran (47 ml) was added N-ethyl, N-propionyl tyramine (3.5 g, 15.8 mmole) and triphenylphosphine (4.55 g, 17.38 mmole). After cooling to 0° C., a solution of diethylazodicarboxylate (2.73 ml, 17.38 mmole) in tetrahydrofuran (16 ml) was added dropwise over 10 minutes. The reaction was allowed to warm to room temperature and stir for 22 hours, evaporated, and triturated with methylene chloride (50 ml) and filtered. The filtrate was chromatographed on silica gel twice using methylene chloride-ethyl acetate and hexane-acetone gradients to give the intermediate phenyl ether (2.95 g, 36%):

$^1$H NMR ($CDCl_3$) (2 rotamers) δ 7.85 (s, 2H), 7.5 (s, 1H), 7.15 (d, J =9 Hz, 1H), 7.05 (d, J=9 Hz, 1H), 6.9 (m, 2H), 5.5 (s, 1H), 4.25 (t, J=7 Hz, 2H), 3.2–3.4 (m, 4H), 3.05 (t, J=7 Hz, 2H), 2.8 (m, 2H), 2.35 (q, J=7 Hz, 1H), 2.15 (q, J=7 Hz, 1H), 1.5 (s, 18H), 1.05–1.2 (m, 6H); FD MS 520 ($M^+$).

C. 2-(3,5-di-t-Butyl-4-hydroxyphenyl)-4-(2-(4-ethylpropylaminoethylphenoxy)ethyl)oxazole To a stirred solution of lithium aluminum hydride (0.42 g, 10.98 mmole) in tetrahydrofuran (22 ml) at 0° C. was added sulfuric acid (0.30 ml, 5.49 mmole) dropwise, maintaining temperature below 10° C. The reaction as allowed to warm to room temperature and stirred for 1 hour, before recooling to 0° C. The intermediate phenyl ether (2.86 g, 5.49 mmole) in tetrahydrofuran (5.5 ml) was added dropwise maintaining the temperature below 5° C. The reaction was stirred at 0° C. for 2.5 hours, then quenched with water (11 $\mu$l). The reaction was diluted with methylene chloride and 5N hydrochloric acid. The aqueous layer was extracted with methylene chloride twice. The combined organics were extracted with brine, then saturated sodium bicarbonate, and dried over sodium sulfate. Chromatography on silica gel using a methylene chloride-methanol gradient gave the free base (1.12 g, 40%). The free base (1.12 g, 2.21 mmole) was dissolved in methylene chloride (30 ml), treated with hydrochloric acid gas, and evaporated to give desired product (1.22 g, 100%):

$^1$H NMR ($CDCl_3$) δ 8.15 (s, 2H), 7.65 (s, 1H), 7.15 (d, J=9 Hz, 2H), 6.9 (d, J=9 Hz, 2H), 5.9 (s, 1H), 4.35 (t, J=7 Hz, 2H), 3.3 (t, J=7 Hz, 2H), 3.2 (m, 6H), 2.95 (m, 2H), 1.9 (m, 2H), 1.5 (m, 18H), 1.45 (t, J=7 Hz, 3H), 1.0 (t, J=7 Hz, 3H); FD MS 507 ($M^+$-HCl+1); Elemental analysis for $C_{32}H_{47}ClN_2O_3$.2.8$H_2O$: Calculated: C, 64.75; H, 8.93; N, 4.72. Found: C, 64.86; H, 8.55; N, 4.70.

EXAMPLE 49

2-(3,5-di-t-Butyl-4-hydroxyphenyl)-4-(2-(4-butylethylaminomethyl-phenyloxy)ethyl)oxazole To a stirred suspension of 2-(3,5-di-t-butyl-4-hydroxyphenyl)-4-(2-(4-formyl-phenyloxy)ethyl)oxazole (5.0 g, 11.88 mmole) in methanol (59 ml) was added N-ethyl-N-butyl amine (16.2 ml, 119 mmole). After 30 minutes the pH was adjusted to 7 with acetic acid. After an additional 30 minutes sodium cyanoborohydride (0.75 g, 11.88 mmole) was added and the pH was adjusted to 6 with acetic acid. The mixture was stirred for 5.5 hours and the methanol was evaporated. The resultant residue was dissolved in ethyl acetate and saturated sodium bicarbonate. The organic layer was extracted with brine, dried over sodium sulfate, evaporated to dryness, and chromatographed on silica gel using a methylene chloride-methanol gradient to give the free base (2.82 g, 47%). The free base was dissolved in methylene chloride (75 ml), treated with hydrochloric acid, and evaporated to give desired product (2.88 g, 95%):

$^1$H NMR ($CDCl_3$) δ 7.9 (s, 2H), 7.55 (s, 1H), 7.55 (d, J=9 Hz, 2H), 6.95 (d, J=9 Hz, 2H), 5.6 (s, 1H), 4.3 (t, J=7 Hz, 2H), 4.1 (d, J=5 Hz, 2H), 3.15 (m, 3H), 2.8–3.0 (m, 3H), 1.8 (m, 2H), 1.5 (s, 18H), 1.4 (t, J=7 Hz, 3H), 1.3 (m, 2H), 0.9 (t, FD MS 506 ($M^+$-HCl); Elemental analysis for $C_{32}H_{47}ClN_2O_3$.$H_2O$ Calculated: C, 68.49; H, 8.80; N, 4.99. Found: C, 68.59; H, 8.77; N, 4.99.

EXAMPLE 50

2-(3,5-di-t-Butyl-4-hydroxyphenyl)-4-(2-(4-ethyl,i-propylaminomethyl-phenyloxy)ethyl)oxazole To a stirred solution of N-ethyl,N-isopropylamine (3.31 ml, 11.88 mmole) in ethanol (24 ml) was added titanium tetraisopropoxide (7.01 ml, 23.8 mmole), then 2-(3,5-di-t-butyl-4-hydroxyphenyl)-4-(2-(4-formyl-phenyloxy)ethyl) oxazole (5.0 g, 11.88 mmole) in ethanol (24 ml). The reaction was stirred for 5 hours, then sodium borohydride (0.67 g, 17.8 mmole) was added. After 18 hours at room temperature, the reaction was poured into 100 ml 2N ammonium hydroxide and diluted with methylene chloride. The mixture was filtered though celite and the filtrate was extracted with brine. The organic layer was dried over sodium sulfate, evaporated to dryness, and chromatographed on silica gel using a methylene chloride-methanol gradient to give the free base (2.30 g, 39%). The free base was dissolved in methylene chloride (75 ml), treated with hydrochloric acid, and evaporated to give desired product (2.28 g, 92%):

$^1$H NMR ($CDCl_3$) δ 7.9 (s, 2H), 7.7 (d; J=9 Hz), 7.6 (s, 1H), 7.0 (d, J=9 Hz, 2H), 5.6 (s, 1H), 4.35 (t, J=7 Hz, 2H), 4.2 (m, 2H), 3.6 (m, 1H), 3.2 (t, J=7 Hz, 2H), 3.0 (m, 2H), 1.2–1.6 (m, 27H); FD MS 492 ($M^+$-HCl); Elemental analysis for $C_{31}H_{45}ClN_2O_3$. 0.5$H_2O$: Calculated: C, 69.19; H, 8.62; N, 5.21. Found: C, 69.05; H, 8.82; N, 5.24.

EXAMPLE 51

2-(3,5-di-t-Butyl-4-hydroxyphenyl)-4-(2-(4-(2-methyloxyethyl)methylaminomethyl-phenyloxy)ethyl)oxazole To a stirred solution of 2-methoxyethylmethylamine (1.07 ml, 10 mmole) in ethanol (5 ml) was added titanium tetraisopropoxide (2.95 ml, 10 mmole), then 2-(3,5-di-t-butyl-4-hydroxyphenyl)-4-(2-(4-formyl-phenyloxy)ethyl) oxazole (2.11 g, 5 mmole) in ethanol (7.5 ml). The reaction was stirred for 4 hours, then sodium borohydride (0.28 g, 7.5 mmole) was added. After 21 hours at room temperature, the reaction was poured into 35 ml 2N ammonium hydroxide and diluted with methylene chloride. The mixture was filtered though celite and the filtrate was extracted with brine. The organic layer was dried over sodium sulfate, evaporated to dryness, and chromatographed on silica gel using a methylene chloride-methanol gradient to give the free base (2.21 g, 89%). The free base was dissolved in methylene chloride (45 ml), treated with hydrochloric acid, and evaporated to give desired product (2.28 g, 96%): $^1$H NMR ($CDCl_3$) δ 8.0 (s, 2H), 7.6 (s, 1H), 7.55 (d, J=9 Hz, 2H), 6.95 (d, J=9 Hz, 2H), 5.75 (s, 1H), 4.35 (t, J=7 Hz, 2H), 4.2 (m, 2H), 3.85–3.95 (m, 2H), 3.4 (s, 3H), 3.0–3.3 (m, 4H), 2.7 (d, J=4 Hz, 3H), 1.5 (m, 18H); FD MS 494 ($M^+$-HCl); Elemental analysis for $C_{30}H_{43}ClN_2O_4$. $H_2O$: Calculated: C, 62.62; H, 8.26; N. 5.10. Found: C, 65.63; H. 8.01; N, 7.03.

EXAMPLE 52

2-(3,5-di-tert-Butyl-4-hydroxyphenyly)-4-((4-N-methyl-N-ethylaminoethyl)phenoxymethyl)oxazole Hydrochloride A. 2-(3,5-di-tert-Butyl-4-hydroxyphenyl))-4-((4-N-formyl-N-ethylamino ethyl)phenoxymethyl)oxazole To a solution of N-formyl-N-ethyl-p-hydroxyphenethylamine (18.9 mmole, 3.65 g) in tetrahydrofuran (47 ml), at room temperature was added 60% sodium hydride (20.8 mmole, 0.83 g). The resulting suspension was stirred at room temperature for 10 minutes then the compound of Example 42(E) (18.9 mmole, 6.92 g) was added directly. The reaction mixture was stirred at room temperature for 5 hours then poured into a 1:1 mixture of ethyl acetate (500 ml) and 10% aqueous sodium hydrogen sulfate solution (500 ml). Phases separated and the organic phase was washed with brine (500 ml). The organic layer was concentrated in vacuo to an oil. The oil was subjected to preparatory chromatography, eluting with 15 to 25% acetone : hexane over a 30 minute period then 25 to 35% acetone : hexane over a twenty minute period. Fractions containing product were combined, concentrated in vacuo to afford 3.2 g of a foam. This material was taken onto the next step without further purification.

B. 2-(3,5-di-tert-Butyl-4-hydroxyphenyl))-4-((4-N-methyl-N-ethylamino ethyl)phenoxymethyl)oxazole Hydrochloride To a suspension of lithium aluminum hydride (13.4 mmole, 0.507 g) in tetrahydrofuran (20 ml) at −10° C. (ice/acetone cooling bath), was added dropwise concentrated sulfuric acid (6.7 mmole, 0.66 g). The reaction was stirred at room temperature for 50 minutes then cooled to 0° C. and treated with a solution of the compound of part A, above, (6.7 mmole, 3.20 g) in tetrahydrofuran (5.0 ml) over a 30 minute period. The suspension was stirred at room temperature for approximately 4 hours then quenched with water (0.48 ml). The resulting heavy suspension was treated with chloroform (100 ml), 5N hydrochloric acid (50 ml) and brine (20 ml). The phases were separated and the aqueous phase was extracted with chloroform (3×50 ml). The organic layers were combined and washed with saturated aqueous sodium bicarbonate (2×50 ml) then brine (1×200 ml). The organic phase was dried over sodium sulfate, filtered and concentrated in vacuo to afford 4.28 g of an oil. Material was then subjected to preparatory chromatography eluting with 0 to 5% (methanol: 1% ammonium hydroxide ): chloroform over a thirty minute period then 5 to 10% (methanol: 1% ammonium hydroxide): chloroform over a twenty minute period. Fractions containing desired compound were combined and concentrated in vacuo to afford 1.76 g of an oil. The oil was treated with chloroform then hydrogen chloride gas was passed through the solution. The solution was concentrated in vacuo to afford 1.76 g of a foam which was dried overnight in a vacuum oven at 60° C.

Mass Spectrum (FDMS): m/z $^1$H NMR ($CDCl_3$): d8.01 (s, 2H), 7.72 (s, 1H), 7.16 (d, 2H), 6.99 (d, 2H), 5.77 (s, 1H), 3.16 (m, 7H), 2.78 (3H), 2.41 (m, 3H), 1.50 (21H) Analysis Calculated for $C_{29}H_{41}Cl\ N_2O_3$+0.3 mole $H_2O$: Calculated: C, 68.77: H, 8.23: N, 5.53. Found: C, 68.60; H, 8.15; N, 5.43.

EXAMPLE 53

2-(3,5-di-tert-Butyl-4-hydroxyphenyl)-4-((RS)-(4N-ethyl-N-methylaminomethyl)phenoxymethyl) oxazoline A. 2-(3,5-di-tert-butyl-4-hydroxyphenyl)-4-((RS)-hydroxymethyl)oxazoline A suspension of lithium aluminum hydride (48 mmole, 1.82 g) in tetrahydrofuran (121 ml) at −10° C. was added dropwise to a solution of the compound of Example 42(B) (24.0 mmole, 8.01 g) in tetrahydrofuran (15 ml). This mixture was stirred at room temperature for approximately 3.5 hours then quenched with water (3.45 ml). Filter aid was added to the reaction then the suspension was filtered through a pad of silica. The filtrate was dried over sodium sulfate, filtered and concentrated in vacuo to afford 7.41 g of crude material. This material was subjected to preparatory chromatography, eluting with 80 to 100% ethyl acetate hexane over a thirty minute period. Fractions containing title compound were combined, concentrated in vacuo to afford 3.47 g.

Mass Spectrum (FDMS): m/z 305(M). Elemental analysis for $C_{18}H_{27}NO_3$: Calculated: C, 70.79: H, 8.91: N, 4.59. Found: C,70.65; H, 9.05; N, 4.56.

B. 2-(3,5-di-tert-Butyl-4-hydroxyphenyl)-4-((RS)-(4-formyl)phenoxymethyl)oxazoline.

To a solution of the compound of part A above (10.0 mmole, 3.06 g), p-hydroxybenzaldehyde (11.0 mmole, 1.35 g) and triphenylphosphine (11.0 mmole, 2.63 g) in tetrahydrofuran (18 ml) cooled to 0° C., was added dropwise diethylazodicarboxylate (11.0 mmole, 1.74 g). The solution was stirred at room temperature for 4.5 hours then concentrated in vacuo to an oil. The oil was treated with chloroform (4 ml) and the crystals were collected by filtration. To the filtrate was added water (10 ml), the pH was adjusted to 8.65 with 0.1N sodium hydroxide, and the phases were separated. The organic phase was washed with water (2×10 ml) and brine (1×10 ml). The organic phases were dried over sodium sulfate, filtered and concentrated in; vacuo. This material was subjected to preparatory chromatography eluting with 40 to 60% ethyl acetate hexane over a 30 minute period. Fractions containing title compound were combined and concentrated in vacuo to afford 2.38 g of a white solid.

Mass Spectrum (FDMS): m/z 409(M). $^1$H NMR (CdCl3): δ 9.88 (s, 1H), 7.83 (d, J=8.7 Hz, 2H), 7.79 (s, 2H), 7.03 (d, J=8.7 Hz, 2H), 5.58 (s, 1H), 4.70 (m, 1H), 4.55 (m, 1H), 4.41 (m, 1H), 4.33 (m, 1H), 4.01 (m, 1H), 1.46 (s, 18H.

C. 2-(3,5-di-tert-Butyl-4-hydroxyphenyl)-4-((RS)-(4N-ethyl-N-methylaminomethyl)phenoxymethyl)oxazoline To a solution of N-methylethylamine (4.9 mmole, 2.00 g) in ethanol (9. ml) at room temperature was added titanium isopropoxide (9.8 mmole, 2.78 g). This mixture was stirred at room temperature for five minutes then the compound of part B, above, (4.9 mmole, 2.00 g) was added directly. The suspension was stirred at room temperature for 8.6 hours then sodium borohydride (7.3 mmole, 0.28 g) was added directly. followed by the addition of ethanol (16 ml). The reaction mixture was stirred at room temperature for approximately 96 hours then treated with aqueous saturated ammonium hydroxide solution. The resulting heavy suspension was stirred for 10 minutes, filter aid was added along with water (25 ml) then filtered through the filter aid. Insoluble material was washed with methylene chloride and brine. The filtrate phases were separated and the aqueous phases were extracted with methylene chloride (2×50 ml). The organic phases were combined, dried over sodium sulfate, filtered and concentrated in vacuo to afford 3.15 g of an oil. The oil crystallized out and was triterated in 9:1 hexane: diethyl ether. Insolubles were collected by filtration. The material was subjected to preparatory chromatography. Product was eluted with 0 to 10% methanol: chloroform over a 30 minute period. Fractions containing title compound were combine and concentrated in vacuo to afford 889 mg. This material was taken up into chloroform (25 ml) and washed with aqueous saturated sodium bicarbonate (2×10 ml) and brine (1×10 ml). The organic phase was dried over sodium sulfate, filtered and concentrated in vacuo to afford 720 mg.

This material was recrystallized from diethyl ether to afford 640 mg of the title compound. This material was dried in a vacuum oven overnight at 45° C.

Mass Spectrum (FDMS): m/z 453 (M+1). $^1$H NMR (CdCl3): d7.79 (s, 2H), 7.26 (d, J=8.5 Hz, 2H), 6.90 (d, J=8.5 Hz, 2H), 5.57(s, 1H), 4.64 (m, 1H), 4.53 (m, 1H), 4.38 (m, 1H), 4.27 (m, 1H), 3.90 (m, 1H), 3.60 (2H), 2.60 (2H), 2.30 (2H), 1.46 (s, 18H), 1.29 (3H). Elemental analysis for $C_{28}H_{41}Cl\ N_2O_3$: Calculated: C, 74.30: H, 8.91: N, 6.19. Found: C,74.45; H, 9.10; N, 6.22.

EXAMPLE 54

2-(3,5-di-tert-Butyl-4-hydroxyphenyl)-5-((4-N-methyl-N-ethylaminomethyl)phenoxymethyl) benzoxazole A. 2-(3,5-di-tert-Butyl-4-hydroxyphenyl)-5-methoxybenzoxazole A solution of 2-hydroxy-5-methoxyaniline (36.9 mmole, 5.13 g), boric acid (36.9 mmole, 2.23 g) and 3,5-di-tertbutyl-4-hydroxybenzoic acid (36.9 mmole, 9.23 g) in xylene (550 ml) was refueled using a Dien Stark trap for approximately two days. The reaction mixture was then concentrated in vacuc to an oil. The oil was treated with ethyl acetate (200 ml) and washed with saturated aqueous sodium bicarbonate (3×200 ml). The organic phase was dried over sodium sulfate, filtered, and concentrated in vacuo to afford 15.96 g of a black oil. The material was subjected to preparatory chromatography eluting with 15 to 30% ethyl acetate: hexane over a 30 minute period. Fractions containing title compound were combined and concentrated in vacuo to afford 5.18 g of a solid.

Mass Spectrum (FDMS): m/z 353 (M). $^1$H NMR ($CdCl_3$): d8.07 (s, 2H), 7.44 (d, J=8.8 Hz, 1H), 7.25 (d, J=2.5 Hz, 1H), 6.90 (dd. J=8.8,2.5 Hz, 1H), 5.64 (s, 1H), 3.86 (s, 3H), 1.52 (s, 18H). Elemental analysis for $C_{22}H_{27}NO_3$ Calculated: C, 74.76: H, 7.70: N, 3.96. Found: C,74.62; H, 7.57; N, 4.01.

B. 2-(3,5-di-tert-Butyl-4-hydroxyphenyl)-5-hydroxybenzoxazole

A solution of the compound of part A, above, (14.7 mmole, 5.18 g) in methylene chloride (26 ml) at −78° C. was treated with boron tribromide over a 5 minute period. The reaction was stirred at −78° C. for 45 minutes then at −10 C. for one hour then recooled back down to −78° C. At this point, the reaction was quenched with acetone (3 ml), warmed to 0° C. and saturated aqueous sodium bicarbonate (25 ml) was added. Additional saturated aqueous sodium bicarbonate (25 ml) was added followed by ethyl acetate (250 ml). Phases were separated and the aqueous phase was extracted with ethyl acetate (100 ml). The combined organic phases were dried over sodium imitate, filtered and concentrated in vacuo to afford 2.2 g of a solid. A solid precipitate developed while drying with sodium sulfate. This material was carefully separated from the sodium sulfate providing an additional 3.23 g of the title compound.

Mass Spectrum (FDMS): m/z 340 (M+1). $^1$H NMR (DMSOd6): d7.94 (s, 2H), 7.75 (s, 1H), 7.52 (d, J=8.7 Hz, 1H), 7.05 (d, J=2.4 Hz, 1H), 6.78 (dd. J=8.7,2.4 Hz, 1H), 1.44 (s, 18H). Elemental analysis for C21H25NO3 0.3 mole H2O: Calculated: C, 73.14: H, 7.48: N. 4.06. Found: C,73.04; H, 7.35; N, 4.00.

C. 2-(3,5-di-tert-Butyl-4-hydroxyphenyl)-5-(4-formylphenoxy)benzoxazole.

A suspension of the compound of part B, above, (14.6 mmole, 4.97 g), powdered potassium carbonate (29.3 mmole, 4.05 g), 4-bromobenzaldehyde (29.3 mmole, 5.42 g) and copper (I) iodide (0.7 mmole, 0.139 g) in pyridine (25 ml) was sonicated for approximately 4 hours then concentrated in vacuo and heated at 140° C. for approximately 17 hours. The reaction was then cooled to room temperature, ethyl acetate (100 ml) was added and the reaction was washed with water (3×100 ml) and 10% aqueous sodium hydrogen sulfate (2×100 ml). The organic phase was dried over sodium sulfate, filtered and concentrated in vacuo to afford 7.64 g of an oil. The material Bras subjected to preparatory chromatography eluting with 10 to 25% acetone: hexane over a 30 minute period. Fractions containing title compound were combined, concentrated in vacuo and set aside. Fractions containing title compound plus impurity were rechromatographed eluting with 2 to 5% ethyl acetate hexane for the first 12 fractions (fraction size approximately 250 ml) then the remainder was eluted with 10% acetone hexane. Fractions containing title compound were combined along with fractions from the prior run and concentrated in vacuo to afford 2.18 g of a solid. This material was taken on to the next step without further purification.

Mass Spectrum (FDMS): m/z 443 (M). $^1$H NMR (DMSOd6): δ 9.93 (s, 1H), 7.99 (s, 2H), 7.93 (d, J=8.7 Hz, 2H), 7.85 (d, J=7.8 Hz, 2H), 7.60(d, J=2.4 Hz, 1H), 7.17 (dd, J=8.7,2.4 Hz, 1H), 7.13 (d, J=8.7 Hz, 2H), 1.46 (s, 18H).

D. 2-(3,5-di-tert-Butyl-4-hydroxyphenyl)-5-((4-N-methyl-n-ethylaminomethyl)phenoxymethyl)benzoxazole To a suspension of the compound of Part C, above (4.6 mmole, 2.06 g) in ethanol (27.6 ml) was added N-ethyl-N-methylamine (9.3 mmole, 0.549 g) followed by titanium (IV)isopropoxide. After stirring at room temperature for 4 hours, sodium borohydride (7.0 mmole, 0.263 g) was added. This suspension was stirred at room temperature for approximately 15.5 hours then quenched with 2N ammonium hydroxide (31 ml). The suspension was stirred for 15 minutes then filter aid was added and filtered through a pad of filter aid. Insolubles were washed with chloroform (100 ml) and brine (100 ml). The phases separated, and the aqueous phase was extracted with chloroform (3×50 ml). The combined organic phases were concentrated in vacuo to an oil. The material was then subjected to preparatory chromatography eluting with 0 to 10% (methanol: 1% ammonium hydroxide): chloroform over a thirty minute period. Fractions containing title compound were combined, dried over sodium sulfate and filtered. The filtrate was saturated with hydrogen chloride gas. The solution was then concentrated in vacuo to a foam. The foam was dried in a vacuum oven at 60° C. overnight to afford 0.766 g of the title compound.

Mass Spectrum (FDMS): m/z 486 (M-HCl). $^1$H NMR (CdCl3) δ 8.07 (s, 2H), 7.55 (dd, J=8.75, 2.4 Hz, 3H), 7.38 (d, J=2.5 Hz, 1H), 7.03 (m, 3H), 5.69(s, 1H), 4.12 (m, 2H), 3.20 (m, 1H), 2.94 (m, 1H), 2.67 (d, J=5.0 Hz, 3H), 1.52 (s, 21H).

EXAMPLE 55

2-(3,5-di-tert-Butyl-4-hydroxyphenyl))-4-((4-N-ethyl-N-methylamino methyl)phenoxyethyl)-1,3,5-oxadiazole A. 2-(3,5-di-tert-butyl-4-hydroxyphenyl))-4-(methoxyethyl)-1,3,5-oxadiazole To a suspension of 3,5-di-tert-butyl-4-hydroxybenzoic acid (13.6 mmole, 3.41 g) in xylene (3.3 ml) at room temperature was added thionyl chloride. The suspension was heated at 45° C. for 140 minutes to remove excess thionyl chloride. At this point the acid chloride derivative was transferred to a drop addition funnel. This material was added over a five minute period to a solution of methoxyethylamidoxime (15.0 mmole, 1.78 g) in pyridine (6.7 ml). After the addition was complete, the reaction was heated at 100° C. for one hour. The suspension was concentrated to an oil then heated at 130° C. for 1.5 hours. The reaction was cooled to room temperature, methylene chloride and water were added and the phases were separated. The aqueous phase was extracted with methylene chloride. The combined organic phases were washed with saturated aqueous sodium bicarbonate (2×50 ml) and brine (1×50 ml). The organic phase was dried over sodium sulfate, filtered, and concentrated in vacuc to afford 4.4 g of an oil. The material was subjected to preparatory chromatography eluting with 15% acetone: hexane. Fractions containing title compound were combined, concentrated Ir; vacuo: to afford 2.12 g. This material was taken onto the next step without further purification.

$^1$H NMR (CdCl3) δ 7.94 (s, 2H), 5.71(s, 1H), 3.83 (t, J=6.8 Hz, 2H), 3.39 (s, 3H), 3.06 (t, J=6.8 Hz, 2H), 1.49 (s, 18H).

B. 2-(3,5-di-tert-Butyl-4-hydroxyphenyl))-4-(hydroxyethyl)-1,3,5-oxadiazole

To a solution of the compound of part A, above, (6.4 mmole, 2.12 g) in methylene chloride (11.3 ml) cooled to 0° C., was added borontribromide (19.1 mmole, 4.79 g). The reaction was stirred 2.7 hours at 0° C. then quenched with saturated aqueous sodium bicarbonate (10 ml). Water (10 ml) and methylene chloride (10 ml) were added, phases were separated and the aqueous phase was extracted with methylene chloride (1×25 ml). The combined organic phases were dried over sodium sulfate, filtered, and concentrated in vacuo to afford 2.27 g of an oil. The material was subjected to preparatory chromatography eluting with 20 to 35% ethyl acetate:hexane over a 30 minute period. Fractions containing title compound were combined and concentrated in vacuo to afford 1.63 g of the title compound.

Mass Spectrum (ion spray MS): m/z 318 (M) $^1$H NMR (CdCl3): d7.94 (s, 2H) 5.74(s, 1H), 405 (t, J=5.8 Hz, 2H), 3.04 (t, J=5.8 Hz, 2H), 2.73 (t, J=6.4 Hz, 1H), 1.48 (s, 18H). Elemental analysis for $C_{18}H_{26}N_2O_3$: Calculated: C, 67.90: H, 8.23: N, 8.80. Found: C,68.03; H, 8.27; N, 8.67.

C. 2-(3,5-di-tert-Butyl-4-hydroxy,phenyl))-4-!(4-formylphenoxy ethyl)-1,3,5-oxadiazole To a solution of the compound of part B, above, (4.8 mmole, 1.49 g), triphenylphosphine (5.1 mmole, 1.35 g) and p-hydroxybenzaldehyde (5.1 mmole, 0.629 g) in tetrahydrofuran (8.6 ml) at 0° C. was added diethylazodicarboxylate (5.1 mmole, 0.895 g). The reaction was stirred at room temperature for four days then concentrated in vacuo to an oil. The material was subjected to preparatory chromatography eluting with 20 to 35% ethyl acetate: hexane over a 30 minute period. Fractions containing title compound plus p-hydroxybenzaldehyde were combined and concentrated in vacuo to an oil. The oil was treated with ethyl acetate (50 ml) then washed with 10% aqueous potassium carbonate (3×50 ml) then 10% aqueous sodium bisulfate (1×50 ml). The organic phase was dried over sodium sulfate, filtered, and concentrated in vacuo to afford 520 mg of a foam. The material taken on to the next step without further purification.

$^1$H NMR (CdCl3): δ 9.88 (s, 1H), 7.94 (s, 2H), 7.83 (d, J=8.7 Hz, 2H), 7.07 (d, J=8.7 Hz, 2H), 5.74(s, 1H), 4.51 (t, 2H), 3.31 (t, 2H), 1.48 (s, 18H).

D. 2-(3,5-di-tert-Butyl-4-hydroxyphenyl))-4-((4-N-ethyl-N-methylamino methyl)phenoxyethyl)-1,3,5-oxadiazole To a solution of the compound of part B above, (3.5 mmole, 0.450 g) in 1,2-dichloroethane (5 ml) was treated with sodium triacetoxyborane (1.1 mmole, 0.063 g) followed by N-methyl-N-ethyl amine (1.1 mmole, 0.063 g). The reaction was stirred at room temperature for approximately 24 hours then quenched with aqueous sodium bicarbonate (25 ml). Ethyl acetate was added, stirred 15 minutes then the phases were separated. The organics were washed with aqueous sodium bicarbonate (3×25 ml). The organic phase was concentrated in vacuo to an oil. The material was then subjected to preparatory chromatography, eluting with 0 to 10% (methanol: 1% ammonium hydroxide): chloroform over a thirty minute period. Fractions containing title compound were combined, dried over sodium sulfate and filtered. The filtrate was saturated with hydrogen chloride gas. The solution was then concentrated in vacuo to a foam. The foam was dried in a vacuum oven at 60° C. overnight to afford the title compound.

Mass Spectrum (FDMS): m/z $^1$H NMR (CdCl3): δ 7.94 (s, 2H), 7.49 (d, 2H), 7.00 (d, 2H), 5.73 (s, 1H), 4.44 (t, 2H), 4.10 (m, 2H), 3.28 (t, 2H), 3.18 (m, 1H), 2.86 (m, 1H), 2.63 (m, 3H), 1.58 (3H), 1.49 (s, 18H). Elemental analysis for C28H40ClN3O3: Calculated: C, 66.98: H, 8.03: N, 8.37. Found: C, 66.86; H, 7.91; N, 8.27.

EXAMPLE 56

2-(3,5-di-tert-Butyl-4-hydroxyphenyl))-4-((4-N-methyl-N-ethylamino methyl)-1,2,3,4-tetrahydronaphthyl-6-oxyethyl)oxazole Hydrochloride A. 2-(3,5-di-tert-Butyl-4-hydroxyphenyl))-4-((4-carbomethoxymethyl)phenoxy)oxazole To a solution of the compound of Example 1, part C, above, (31.2 mmole, 10.14 g), 4-hydroxyphenyl acetate (35.1 mmole, 5.85 g) and triphenylphosphine (35.1 mmole, 9.23 g) in tetrahydrofuran (56 ml) at room temperature was added diethylazodicarboxylate (35.1 mmole, 6.13 g). The reaction was stirred overnight at room temperature before being concentrated in vacuo to an oil. The oil was treated with methylene chloride and filtered, and the filtrate was concentrated in vacuo to an oil. The material was subjected to preparatory chromatography, eluting with 20 to 35% acetone: hexane over a 30 minute period. Fractions containing title compound were resubjected to chromatography, eluting with 15 to 30% ethyl acetate hexane over a 30 minute period. Fractions containing title compound were combined, and concentrated in vacuo to afford 12.07 g of an oil.

Mass Spectrum (FDMS): m/z 465 (M). $^1$H NMR (DMSOd6): d7.92 (s, 1H), 7.73 (s, 2H), 7.52(s, 1H), 7.16 (d, J=8.7 Hz, 2H), 6.90 (d, J=8.7 Hz, 2H), 4.22 (t, J=6.6 Hz, 2H), 3.59 (s, 5H), 2.96 (t, J=6.6 Hz, 2H), 1.41 (s, 18H). Elemental analysis for $C_{28}H_{35}NO_5$: Calculated: C, 72.23: H, 7.58: N, 3.01. Found: C, 72.47; H, 7.65; N, 3.10.

B. 2-(3,5-di-tert-Butyl-4-hydroxyphenyl))-4-((4-ethanoate) phenoxy)oxazole

A suspension of the compound of part A, above (26 mmole, 12.07 g) and lithium hydroxide (78 mmole, 1.86 g) in tetrahydrofuran (87 ml) and water (28 ml) was heated at 65° C. for 4.5 hours. The reaction was then cooled to room temperature and brine (25 ml) and ethyl acetate (25 ml) and hexane (25 ml) were added. The phases were separated and the organic phase was washed with 10% aqueous sodium hydrogen sulfate (1×50 ml) and brine (1×50 ml). The organic phase was concentrated in vacuo then subjected to preparatory chromatography, eluting with 0 to 10% methanol: methylene chloride over a 30 minute period. Fractions containing title compound were rechromtatographed eluting with 0 to 3% methanol: methylene chloride over a 30 minute period. Fractions containing title compound were combined, and concentrated, in vacucl to afford 1.60 g of a foam.

Mass Spectrum (FDMS): m/z 452 (M+1). $^1$H NMR (CdCl3) d7.82 (s, 2H), 7.40 (s, 1H), 7.17(d, 2H), 6.85 (d, 2H), 5.50 (s, 1H), 4.16 (t, 2H), 3.56 (s,. 2H), 3.06 (t, 2H), 1.48 (s, 18H). Elemental analysis for C27H33NO5: Calculated: C, 71.82: H, 7.37: N, 3.10. Found: C, 71.82; H, 7.46; N, 3.03.

C. 6-[2-[(3,5-di-tert-Butyl-4-hydroxyphenyl)-4-oxazolyl]-ethoxy]-tetralone

To a solution of the compound of part B, above (3.5 mmole, 1.59 g) in methylene chloride (5 ml) and 1 drop dimethylformamide at room temperature, was added thionyl chloride (4.2 mmole, 0.50 g). This solution was heated at 45° C. for 2 hours then cooled to room temperature and concentrated in vacuo to a foam. To a suspension of aluminum chloride (10.6 mmole, 1.41 g) in methylene chloride (24 ml) at −10° C. was added a solution of the acid chloride in methylene chloride (3 ml) over a three minute period. Next, ethylene gas was bubbled through the suspension for approximately 105 minutes. The reaction was then poured into ice/water (50 ml) with stirring. Phases were separated, and the organic phase was washed with 1N hydrochloric acid (2×50 ml) and brine (1×100 ml). The organic phase was dried over sodium sulfate, filtered and concentrated in vacuo to afford 1.46 g of a foam. The material was subjected to preparatory chromatography eluting with 20 to 35% ethyl acetate: hexane over a 30 minute period. Fractions containing title compound were combined, and concentrated in vacuo to afford 680 mg of an oil.

Mass Spectrum (ion spray MS): m/z 462(M+1). $^1$H NMR (CdCl3): d7.83 (s, 2H), 7.50 (s, 1H), 7.04 (d, 1H), 6.82 (2H), 5.49(s, 1H), 4.28 (2H), 3.51 (2H), 3.03 (m, 4H), 2.55 (2H), 1.48 (s, 18H). Elemental analysis for $C_{29}H_{35}NO_4$: Calculated: C, 75.46: H, 7.64: N, 3.03. Found: C, 75.41; H, 7.39; N, 3.02.

D. 2-(3,5-di-tert-Butyl-4-hydroxyphenyl))-4-((4-N-methyl-N-ethylamino methyl)1,2,3,4-tetrahydronaphthyl-6-oxyethyl)oxazole Hydrochloride This compound was substantially prepared as described for in Example 55, part D.

Mass Spectrum (ion spray MS): m/z 505 (M+1). $^1$H NMR (CdCl3): δ 8.25 (s, 2H), 7.71 (s, 1H), 7.00 (1H), 6.71 (1H), 6.64 (1H), 5.30 (s, 1H), 4.39 (2H), 3.57 (m, 1H), 3.39 (2H), 3.11 (m, 6H), 2.79 (3H), 1.53 (s, 18H)

EXAMPLE 57

2-(3,5-di-t-Butyl-4-hydroxyphenyl)-4-(3-keto-3-(4-methylethylaminomethyl-phenyl)propyl)oxazole A. 2-(3,5-di-tert-Butyl-4-hydroxyphenyl)-4-(2-iodoethyl)oxazole.

A solution of triphenylphosphine (118.8 mmole, 31.12 g), in methylene chloride (460 ml) was treated with iodine (approximately 30.17 g) until a dull yellow color persisted. The reaction stirred fifteen minutes, then a solution of 2-(3,5-di-tert-butyl-4-hydroxyphenyl)-4-(2-hydroxyethyl)oxazole (79.2 mmole, 25.10 g) and imidazole (158.3 g, 10.77 g) in methylene chloride (300 ml) was added over a ten minute period. At 3.0 hours the reaction was concentrated in vacuo then taken up into methylene chloride and subjected to flash silica gel filtration. Desired product was eluted with 1:1 ethyl acetate:hexane, collecting 500 ml fractions. Desired fractions were combined, washed with 1×250 ml 1N sodium thiosulfate and 1×250 ml brine, dried over magnesium sulfate, filtered, and concentrated in vacuo to afford 32.53 g (96%) of the title compound.

Mass Spectrum(FDMS): m/z 427(M). $^1$H NMR (CdCl3): d 7.90 (s, 2H), 7.52 (s, 1H), 5.60 (s, 1H), 3.50 (t, J=7.1 Hz, 2H), 3.18 (t, J=7.1 Hz, 2H), 1.49 (s, 18H). Elemental analysis calculated for $Cl_{19}H_{26}INO_2$: Calculated: C, 53.40; H, 6.13; N, 3.28. Found: C, 53.64; H, 6.06; N, 3.30.

B. 2-(3,5-di-tert-Butyl-4-hydroxyphenyl)-4-(2-cyanoethyl)oxazole

To a solution of sodium cyanide (84.5 mmole, 5.50 g) in dimethylsulfoxide (120 ml) at 92° C. was added 2-(3,5-di-tert-butyl-4-hydroxyphenyl)-4-(2-iodoethyl)oxazole (70.4 mmole, 30.08 g) via a powder addition funnel over an eightyfive minute period. Approximately 1.5 hours later, the reaction was cooled to room temperature and treated with 1:1 ethyl acetate: hexane (250 ml) and 10% aqueous potassium carbonate (250 ml). Three distinct phases result. The lowest phase was separated and discarded. The remaining phases were separated. The aqueous phase was extracted with 1:1 ethyl acetate:hexane (2×200 ml). Combined organic phases were dried over sodium chloride, filtered, reduced in volume and subjected to preparatory chromotography. The material was eluted with 10 to 30% ethyl acetate: hexane. Fractions containing the desired product were combined, dried over $MgSO_4$, filtered and concentrated in vacuo to afford 18.25 g (79%)

Mass Spectrum(FDMS): m/z 326 (M). $^1$H NMR (CDCl$_3$): d 7.84 (s, 2H), 7.53 (s, 1H), 5.54 (s, 1H), 2.94 (t, J=7.1 Hz, 2H), 2.78 (t, J=7.1 Hz, 2H), 1.49 (s, 18H). Elemental analysis calculated for $C_{20}H_{26}N_2O_2$: Calculated: C, 73.59; H. 8.03; N, 8.58. Found: C, 73.37; H, 8.05; N, 8.53.

C. 2-(3,5-di-tert-Butyl-4-hydroxyphenyl-4-(2-formylethyl)oxazole

A solution of 2-(3,5-di-tert-butyl-4-hydroxyphenyl)-4-(2-cyanoethyl)oxazole (52 mmole, 16.99 g) in toluene (167 ml) at −60° C. was treated with a 1.0 molar solution of diisobutylaluminum hydride in toluene (67.7 mmole, 67.7 ml) over an eight minute period. After stirring 15 minutes at −78° C., the dry ice/acetone bath was removed and the reaction was stirred at room temperature for 1.75 hours. Next, the reaction was treated with methanol (6.5 ml) then a saturated solution of ammonium chloride (650 ml). After stirring at room temperature for 1.5 hours, the reaction was treated with 50% sulfuric acid (v/v) until a biphasic solution resulted. Crystals that developed in biphasic solution were removed by filtration. Phases were separated, and the aqueous phase was extracted with ethyl acetate (2×250 ml). The combined organics were washed with aqueous saturated solution of sodium bicarbonate (1×250 ml) then brine (1×500 ml). The organic phase was reduced to approximately 50 ml total volume and subjected to preparatory chromatography. The material was eluted with 0 to 10% methanol: toluene gradient. Fractions containing the desired product were combined, dried over magnesium sulfate, filtered and concentrated in vacuo to afford 15.13 g (88%).

Mass Spectrum(FDMS): m/z 329 (M). $^1$H NMR (DMSOd6): d 9.74 (s, 1H), 7.82 (s, 1H), 7.71 (s, 2H), 7.52 (s, 1H), 2.78 (s, 4H), 1.41 (s, 18H). Elemental analysis calculated for $C_{20}H_{27}NO_3$: Calculated: C, 72.92; H, 8.26; N, 4.28. Found: C, 71.40; H, 8.27; N, 4.23.

D. 2-(3,5-di-t-Butyl-4-hydroxyphenyl)-4-(3-hydroxy-3-(4-(1,3-dioxolan-2-yl-)phenyl)propyl)oxazole To a −70° C. solution of 2-(4-bromophenyl)-1,3-dioxolane (21.67 g, 94.6 mmole) in tetrahydrofuran (142 ml), was added 1.6M n-butyl lithium in hexane (59.1 ml, 94.6 mmole) dropwise over 25 min. The resulting suspension was stirred for 2 hours at −70° C., at which time 2-(3,5-di-tert-butyl-4-hydroxyphenyl)-4-(2-formylethyl)oxazole (10.39 g, 31.53 mmole) in tetrahydrofuran (43 ml) was added dropwise over 30 min. After 1.75 hours, the cooling bath was removed. At −35° C., the reaction was quenched with saturated ammonium chloride and diluted with ethyl acetate and 10% sodium bisulfate. The organic layer was extracted with brine, dried (sodium sulfate), evaporated to dryness, and chromatographed on silica gel using a methylene chloride: ethyl acetate gradient to give the protected aldehyde/alcohol (7.84 g, 51%): $^1$H NMR (CDCl$_3$) δ 7.85 (s, 2H), 7.4 (m, 4H), 7.35 (s, 1H), 5.8 (s, 1H), 5.5 (s, 1H), 4.85 (m, 1H), 4.1 (m, 4H), 3.7 (d, J=4 Hz, 1H), 2.65 (t, J=7 Hz, 2H), 2.1 (m, 2H), 1.45 (s, 18H); FD MS 479 (M$^+$).

E. 2-(3,5-di-t-Butyl-4-hydroxyphenyl)-4-(3-hydroxy-3-(4-formyl)phenyl)propyl)oxazole To a stirred solution of 2-(3,5-di-t-butyl-4-hydroxyphenyl)-4-(3-hydroxy-3-(4-(1,3-dioxolan-2-yl-)phenyl)propyl)oxazole(7.84 g, 16.34 mmole) in acetone (82 ml) and water (25 ml), was added pyridinium p-toluene sulfonate (0.21 g, 0.82 mmole). The reaction was refluxed for 1.5 hours before the acetone was evaporated. The remaining aqueous suspension was extracted with ethyl acetate. The organic layer was extracted with brine, dried (sodium sulfate), and evaporated to dryness to give the aldehyde/alcohol intermediate (6.82 g, 96%):

Mass Spectrum(FDMS): m/z 435 (M). $^1$H NMR (CdCl$_3$): d 9.98 (s, 1H), 7.87 (d, J=8.0 Hz, 2H), 7.82 (s, 1H), 7.70 (s, 2H), 7.59 (d, J=8.0 Hz, 2H), 7.50 (s, 1H), 5.53 (d, J=4.6 Hz, 1H), 4.72 (m, 1H), 2.53 (m, 2H), 1.92 (m, 2H), 1.41 (s, 18H). Elemental analysis calculated for $C_{27}H_{33}NO_4$: Calculated: C, 74.46; H, 7.64; N, 3.22. Found: C, 74.22; H, 7.64; N, 2.96.

F. 2-(3,5-di-t-Butyl-4-hydroxyphenyl)-4-(3-hydroxy-3-(4-methylethylaminomethyl-phenyl)propyl)oxazole To a solution of 2-(3,5-di-t-butyl-4-hydroxyphenyl)-4-(3-hydroxy-3-(4-formyl)phenyl)propyl)oxazole (11.9 mmole, 5.18 g) in methanol (50 ml) cooled to −10° C., was added N-methylethylamine (118.9 mmole, 7.03 g) followed by acetic acid (118.9 mmole, 7.14 g) while maintaining the temperature below 4° C. during the additions. Next, sodium cyanoborohydride (12.5 mmole, 0.78 g) was added then stirred at room temperature for two days. The reaction was then concentrated in vacuc, treated with 1:1 ethyl acetate hexane (50 ml), phases were separated, and the organics were washed with aqueous saturated sodium bicarbonate (25 ml) followed by 10% aqueous sodium bisulfate and finally with brine (25 ml). The organics were concentrated in vacuo, treated with chloroform and subjected to preparatory chromatography. The material was eluted with 0 to 10% (methanol: 1% ammonium hydroxide): toluene gradient over a twenty minute period. Fractions containing desired product were concentrated in vacuc, treated with chloroform, then hydrogen chloride gas. The solution was concentrated in vacuo to a foam. The foam was taken up into methylene chloride (20 ml), filtered through talc and washed with methylene chloride (10 ml). The filtrate was treated with diisopropyl ether (10 ml). The solution was boiled down to approximately 10 ml resulting in material gumming out of solution. The solvent was decanted off and the gummy material was concentrated in vacuo to afford the title compound as a foam (1.78 g, 29%).

Mass Spectrum(ion spray): m/z 479 (M-HCl+1). $^1$H NMR ($CdCl_3$): d 8.12 (s, 2H), 7.62 (s, 1H), 7.53 (d, J=8.1 Hz, 2H), 7.46 (d, J=8.1 Hz, 2H), 5.93 (s, 1H), 4.88 (m, 1H), 4.14(m, 2H), 3.18 (m, 1H), 2.95 (m, 2H), 2.88 (m, 1H), 2.63 (d, J=4.8 Hz, 2H), 2.20 (m, 2H), 1.41 (m, 21H). Elemental analysis calculated for $C_{30}H_{43}ClN_2O_3$. $1.5H_2O$: Calculated: C, 66.46; H, 8.55; N, 5.17. Found: C, 66.38; H, 8.57; N, 5.22.

G. 2-(3,5-di-t-Butyl-4-hydroxyphenyl)-4-(3-keto-3-(4-methylethylaminomethyl-phenyl)propyl)oxazole To a stirred solution of oxalyl chloride (0.23 ml, 2.68 mmole) in methylene chloride (6.1 ml) at 60° C., was added dropwise a solution of dimethylsulfoxide (0.38 ml, 5.37 mmole) in methylene chloride (1.2 ml). After warming to −20° C., a solution of the compound of part F, above (1.17 g, 2.44 mmole) in methylene chloride (2.4 ml) was added while the temperature was maintained between −20 and −25° C. After 30 minutes at this temperature, triethylamine (1.7 ml, 12.2 mmole) was added dropwise. The reaction was allowed to warm to room temperature and diluted with water. The aqueous layer was extracted with methylene chloride. The combined organic layers were extracted with brine, dried over sodium sulfate, evaporated to dryness, and chromatographed on silica gel using a methylene chloride-methanol gradient to give the free base (1.37 g, 85%). The free base (0.67 g, 1.41 mmole) was dissolved in methylene chloride (20 ml), treated with hydrochloric acid, and evaporated to give the desired product (0.71 g, 99%):

$^1$H NMR ($CDCl_3$) δ 8.1 (m, 4H), 7.8 (d, J=9 Hz, 2H), 7.6 (s, 1H), 5.8 (s, 1H), 4.2 (m, 2H), 3.65 (t, J=7 Hz, 2H), 3.2 (m, 3H), 2.95 (m, 1H), 2.65 (s, 3H), 1.5 (m, 21H); FD MS 476 ($M^+$-HCl+1); Elemental analysis for $C_{30}H_{41}ClN_2O_3$. $1.3H_2O$: Calculated: C, 67.16; H, 8.19; N, 5.22. Found: C, 66.90; H, 7.75; N, 5.24.

EXAMPLE 58

2-(3,5-di-tert-Butyl-4-hydroxyphenyl))-4-((4-N-methyl-N-ethylaminoethyl)phenoxymethyl)oxazole Hydrochloride A. N-Carbo(3,5-di-t-butyl-4-hydroxy)phenyl-DL-serine Methyl Ester In a 250 ml flask d,l-serine methyl ester hydrochloride( 5 g, 20 mmole) was slurried in 50 ml methylene chloride at room temperature. Triethylamine (11.15 ml, 80 mmole) was added all at once, and the resulting solution was stirred at room temperature for 1 hour. In a separate 250 ml flask 3,5-di-tert-butyl-4-hydroxybenzoic acid was combined with 2-chloro-4,6-dimethoxy-1,3,5-triazine in 100 ml methylene chloride. The resulting solution was cooled to −10° C. and 4-methylmorpholine was added dropwise, and stirred at −10° C. for 1 hour. This solution was added to the free base solution of d,l-serine methyl ester dropwise at −10° C. After the addition was complete, the cooling bath was removed and the resulting solution was stirred to room temperature for 2 hours and quenched with 1N hydrochloric acid (50 ml). The organics were separated and washed with 50 ml of saturated brine solution, dried over magnesium sulfate, and filtered. The filtrate was concentrated under vacuum to a white foam which was dissolved in 40 ml ether and tituated with 40 ml of hexane. The resulting white solid w as filtered to provide 5.23 g of the desired product in 74.5% yield.

$^1$H NMR ($CDCl_3$) δ 7.65 (2H, s); 7.05 (1H, d); 4.85 (1H, m); 4.05 (2H, d); 3.8 (3H, s); 1.5 (18H, t). MS-FD, 351.

B. 4-((RS)Carbomethoxy)-2-(3,5-di-tert-butyl-4-hydroxyphenyl))-2-oxazoline

The compound of part A, above (1 g, 2.85 mmole) was dissolved in 10 ml of methylene chloride at room temperature followed by the dropwise addition of thionyl chloride (0.23 ml, 3.13 mmole). The resulting mixture was stirred for 2 hours at room temperature and then quenched with 10 ml of saturated sodium bicarbonate. The biphasic solution was then stirred for 30 minutes at room temperature and the organics were separated and dried over magnesium sulfate. The drying agent was filtered and concentrated under vacuum to give 0.75 g of a white foam in 79% yield.

$^1$H NMR ($CDCl_3$): δ 7.8 (2H, s); 5.6 (1H, s); 4.9 (1H, m); 4.6 (2H, m); 3.8 (3H, s); 1.5 (18H, s). MS-FD, 333.

C. 4-(Carbomethoxy)-2-(3,5-di-tert-butyl-4-hydroxyphenyl)oxazole

The compound of part B, above (5 g, 15 mmole) was dissolved in 50 ml of dry dioxane, and 2,3-dichloro-5,6-dicyano-1,4-benzoquinone (3.75 g, 16.5 mmole) was added. The resulting solution was heated to reflux for 1.5 hours, and then cooled to room temperature. The solution was filtered through a pad of silica gel and decolorized with activated carbon (20 g) for 16 hours. The dark solution was filtered through diatomaceous earth, and the filtrate was concentrated under vacuum to give 4.90 g of a tan solid in 98.7% yield.

$^1$H NMR ($CDCl_3$): δ 8.21 (1H, s); 7.9 (2H, s); 5.6 (1H, s); 3.95 (3H, s); 1.5 (18H, s). MS-FD, 331.

D. (4-(Hydroxymethyl)-2-(3,5-di-tert-butyl-4-hydroxyphenyl))-2-oxazole.

To a slurry of lithium aluminum hydride (0.043 g, 1.1 mmol) in 10 mL dry tetrahydrofuran at 0° C. was added the compound of part of C, above (0.25 g, 0.76 mmol) in one portion. The reaction was quenched after 1 hour by the sequential dropwise addition of 0.25 mL water, 0.25 mL 15% NaOH and 0.75 mL water. The resulting mixture was stirred at room temperature for 1 hour and then filtered through celite. The pH of the filtrate was adjusted to 7 by the addition of 1N hydrochloric acid. The mixture was extracted with ethyl acetate (2×50 mL). The organic solution was slurried with magnesium sulfate (0.5 g) and activated carbon (2 g) for 4 hours. The mixture was filtered through celite and concentrated by rotary evaporation to give subtitled compound (0.173 g) as an off-white solid.

E. Preparation of N-propyl-N-ethyl-4-hydroxyphenyl Acetamide

To a solution of 4-hydroxyphenyl acetic acid (88.43 g, 653 mmol) in 700 mL tetrahydrofuran at −50° C. was added a solution of 4-methylmorpholine (66.1 g, 653 mmol) in 30 mL tetrahydrofuran. iso-Butylchloroformate (89.3 g, 653 mmol) was added to the mixture and the resulting solution was stirred at −50° C. for 2 hours. A solution of ethylpropylamine (57 g, 654 mmol) in 30 mL of tetrahydrofuran was added over 15 minutes. After 3 hours, the reaction mixture was poured into a 1:1 mixture of ethyl acetate and 1N hydrochloric acid. The ethyl acetate layer was washed with sodium bicarbonate and brine, then dried over sodium sulfate, filtered and concentrated to give a clear colorless oil (135 g). Purification of the technical grade material was accomplished by crystallization from ethyl acetate.

Spectral data was collected from a 1:1 mixture of amide rotamers. $^1$H NMR ($CDCl_3$, 300 MHz) δ 8.2 (br s, 1H), 7.01 (m, 2H), 6.7 (d, 2H, J=12 Hz), 3.65 (s, 2H), 3.64 (s, 2H), 3.3 (m, 4H), 1.6 (m, 2H), 1.1 (m, 3H), 0.89 (t, 3H, J=7 Hz).

F. Preparation of N-propyl-N-ethyl-4-hydroxyphenylethyl Amine

A three neck flask fit with a condenser, addition funnel and Dean-Stark trap was charged with a solution of the compound of part E, above, (48.6, 220 mmol) in 250 mL tetrahydrofuran and heated to 50° C. Borane dimethylsulfide (10.0–10.2M, 86 mL) was added dropwise. After complete addition, the mixture was heated to reflux for 3 hours with removal of approximately 60 mL of the distillate by means of the Dean Stark trap. The reaction mixture was then concentrated by distillation to approximately 25% of the original volume. Methanol (150 mL) was slowly added to the mixture. The resulting mixture was heated to reflux for 30 minutes and then concentrated by distillation to 50 mL total volume. The solution was cooled to room temperature and a 0.77M hydrochloride acid solution in methanol (285 mL) was added. The resulting mixture was concentrated by rotary evaporation to a white solid. The residue was slurried in ethyl acetate (1% methanol) and heated to reflux. The mixture was cooled and filtered to give the hydrochloric salt of desired product (42 g) as a white solid.

$^1$H NMR (DMSO, 300 MHz) δ 10.84 (br s, 1H), 9.43 (s, 1H), 7.08 (d, 2H, J=8 Hz), 6.73 (d, 2H, J=8 Hz), 3.13 (m, 4H), 2.94 (m, 4H), 1.7 (m, 2H), 1.24 (t, 3H, J=7 Hz), 0.9 (t, 3H, 7 Hz).

A portion of this material (26 g) was free-based by partitioning between ethyl acetate and a sodium hydroxide solution to Ph 8. The organic phase was dried over sodium sulfate, filtered and concentrated to yield the desired product as a clear colorless oil (24 g).

G. 4-(Bromomethyl)-2-(3,5-di-tert-butyl-4-hydroxyphenyl) oxazole.

To a solution of the compound of part D, above, in ~3 mL dry dichloromethane at 0° C., was added phosphorus tribromide (0.089 g, 0.33 mmol) dropwise. The mixture was warmed to 23° C. for 1 hour and the reaction was quenched by the dropwise addition of 3 mL pH 7 buffer which resulted in a temperature increase to 32° C. The organic phase was diluted with dichloromethane, and brine was added to clarify the layers. The organic solution was collected and dried over magnesium sulfate, filtered and concentrated by rotary evaporation to give sub-titled compound (0.084 g) as a white foam.

$^1$H NMR ($CDCl_3$, 300 MHz) δ 7.85 (5,2H), 7.65 (s, 1H)), 5.5 (s, 1H), 4.4 (s, 2H), 1.5 (s, 9H).

H. 2-(3,5-di-tert-Butyl-4-hydroxyphenyl))-4-((4-N-formyl-N-ethylamino Ethyl)phenoxymethyl)oxazole To a solution of the compound of part F, above, (2.22 g, 10.2 mmol) in dry tetrahydrofuran was added 60% sodium hydride in mineral oil (0.513 g, 12.8 mmol). The resulting mixture was stirred overnight and the compound of part G, above, (3.75 g, 10.3 mmol) was added. The mixture was heated to reflux for 7 hours and then cooled to 23° C. The mixture was diluted with ethyl acetate and washed with saturated ammonium chloride. The organic solution was dried over magnesium sulfate, filtered and concentrated to a solid which was used in the following step without further purification.

I. 2-(3,5-di-tert-Butyl-4-hydroxyphenyl))-4-((4-N-methyl-N-ethylamino Ethyl)phenoxymethyl)oxazole Hydrochloride Borane dimethylsulfide (3.2 equiv) was added dropwise to a solution of the unpurified amide (above) in 100 mL dry tetrahydrofuran at 23° C. The resulting mixture was heated to reflux for 5 hours, then cooled to room temperature. The volatiles were removed by rotary evaporation and the residue was dissolved in methanol and heated to reflux for 1 hour. The mixture was cooled to 23° C. and hydrochloric acid in ether (10 equiv) was added. The resulting mixture was stirred overnight, then heated to reflux for 4 hours. The mixture was cooled to 23° C. and the volatiles were removed under vacuum. The residue was partitioned between ethyl acetate and saturated sodium bicarbonate. The organic phase was washed with 1 N hydrochloric acid and brine. A small amount of methanol was added to assist layer separation. The organics were dried over magnesium sulfate, filtered and concentrated by rotary evaporation to give a foam. The residue was purified by silica gel chromatography, initially by elution with 95% acetonitrile, 3% water and 2% ammonium hydroxide. A second silica gel purification followed by elution with 90% chloroform and 10% methanol with 1% ammonium hydroxide which gave a white foam.

The white foam was dissolved in methylene chloride and hydrogen chloride (g) was bubbled through the mixture for 5 minutes. The mixture was stirred overnight and the solvent was removed by rotary evaporation to give title product (2.27 g) as a white foam.

MS-FD=492.2

EXAMPLE 59

2-(3,5-di-t-Buty-4-hydroxyphenyl)-4(2-(4-methyl Ethylaminomethylphenoxy)ethyl)oxazole A. Preparation of 2-(3,5-di-t-Butyl-4-hydroxyphenyl)-4-tosyloxyether)oxazole The compound of Example 59 D (50 g, 157.5 mmole) was dissolved in 500 ml of methylene chloride at room temperature. Pyridine (51 ml, 630 mmole) and dimethylaminopropylamine (1.92 g, 15.75 mmole) were added all at once. Next tosic anhydride (64.3 g, 196.9 mmole) was added in portions. The mixture was stirred at room temperature for 30 minutes, and quenched with 200 ml of 1N hydrochloric acid. The mixture was separated and the organics were dried over magnesium sulfate. The drying agent was filtered and the filtrate was filtered through a plug of silica gel and washed with 1.5L of methylene chloride. The methylene chloride was removed under vacuum to give a solid which was slurried in 1L of petroleum ether. The solid was filtered, collected and dried in a vacuum oven at 40° C. An off-white solid was obtained (68.93 g).

Yield=92.7% Elemental Analysis: Calculated: C, 66.22; H, 7.05; N, 2.97. Found: C, 66.38; H, 7.18; N, 3.14.

B. Preparation of N-methyl-N-ethyl-4-hydroxyphenylmethylamide

To a solution of p-hydroxybenzaldehyde (20.01 g, 163.9 mmol) in 400 mL of 1,2-dichloroethane was added N-methylethylamine (11.62 g, 196.7 mmol). The reaction vessel was purged with nitrogen, and sodium triacetoxyborohydride (48.00 g, 226.0 mmol) was added as a solid. The reaction was quenched by addition of saturated sodium bicarbonate. The aqueous layer was washed with ethyl acetate and then the pH was adjusted to 10. The aqueous phase was extracted with ethyl acetate. The ethyl acetate was washed with 1N hydrochloric acid (pH 1) and the organic phase discarded. The pH of the aqueous phase was adjusted to 10 and the product was extracted with ethyl acetate. The organic solution was dried over sodium sulfate, filtered and concentrated to a white solid.

$^1$H NMR ($CDCl_3$, 300 MHz) d 9.95 (s, 1H), 7.10 (d, 2H, J=

C. Preparation of 2-(3,5-di-t-Buty-4-hydroxyphenyl)-4(2-(4-methyl Ethylaminomethylphenoxy)ethyl)oxazole The compound of part A, above, (4.72 g, 10 mmole), was combined with a compound of part B, above (1.73 g, 10.5 mmole), and solid sodium hydroxide (0.6 g, 15 mmole) in 43 ml dry tetrahydrofuran at room temperature. The resulting mixture was heated to reflux under nitrogen for 8 hours. The mixture was cooled to room temperature and the solvents were removed under vacuum to give a residue. The residue was partitioned between ethyl acetate and 1N hydrochloric acid. The organic layer was separated and washed twice with 1N sodium hydroxide and once with brine. The organics were dried over magnesium sulfate. The drying agent was filtered and the filtrate was concentrated under vacuum to give 4.59 g of an oil. The oil was dissolved in methylene chloride and filtered through a pad of silica gel. The silica gel was washed once with methylene chloride and once with methanol. The methanol wash was concentrated under vacuum to give a residue which was partitioned between methylene chloride and a saturated sodium bicarbonate solution. The organic layer was separated and dried over magnesium sulfate. The drying agent was filtered and the filtrate was concentrated to give 3.39 g of the title product as a light red oil.

MS=465.4 Elemental Analysis: Calculated: C, 74.96; H, 8.68; N 6.03. Found: C, 74.67; H, 8.44; N, 5.88.

Assays

The brain is only about 2% of the total body mass, yet it consumes approximately 20% of all the inspired oxygen. Although neurons depend on oxidative metabolism for survival, a consequence of this process is the production of reactive compounds such as hydrogen peroxide and oxy radicals (Cohen and Werner, 1994). In spite of the high vulnerability of the brain to oxygen radical attack, oxygen free-radical reactions and oxidative damage are in most cases held in check by antioxidant defense mechanisms under basal conditions. Pathological conditions of the central nervous system exist, however, where excessive amounts of oxygen free radicals are produced that impair defense mechanisms. Unchecked, these reactive oxygen species (ROS) can lead to DNA damage, peroxidation of membrane lipids and neuronal death.

Oxidative damage caused by free radical production and lipid peroxidation as well as by products of the arachidonic acid cascade are considered to be primary factors in the acute stage pathology of ischemia. Increases in the amounts of free fatty acids after ischemia and during early reperfusion can provide the substrate for lipid peroxidation and for the formation of products of the arachidonic acid cascade (Clemens, et al., Stroke, Vol. 22, No. 8, Aug. 1991).

Several reviews have been written on the role of oxygen radicals in cerebral ischemia (Braugher and Hall, 1989; Hall and Braugher 1989; Koutos, 1989, Floyd, 1990; Nelson, et al., 1992; Panetta and Clemens, 1993).

Evidence has accumulated recently suggesting that free radicals may be involved in the genesis of Parkinson's disease (Graham, 1984; Ogawa, et al., 1993, Ben-Shackar, et al., 1992; Carillo, et al., 1993). Reports have also appeared suggesting free-radical involvement in the pathogenesis of Alzheimer's disease and Down's syndrome (Zelman, et al., 1989. Ceballos-Pecot, et al., 1992; Andorn, et al., 1990; Subbarao, et al., 1990, McIntosh, et al., 1991.) In addition, recent reports suggest the involvement of free radicals in the pathogenesis of ALS (Rosen, et al., 1993; McNamara and Fridovich, 1993).

The compounds of the instant invention inhibit the formation of reactive oxygen species in a mammal and are thereby useful for treating conditions and diseases which are believed to be induced by increased free radical production such as global and cerebral ischemia, Parkinson's disease, Alzheimer's disease, Down's syndrome and ALS.

Compounds of formula I have been shown to prevent ischemia-induced neuronal cell damage as demonstrated in the following test system.

Cerebral Ischemia Model in Rats

Cerebral ischemia was produced in rats by occluding the four arteries that supply blood to the brain according to the following procedure. Male Wistar rats were anesthetized with Metofane and placed into a stereotaxic instrument. A longitudinal incision was made on the dorsal surface of the neck. The neck muscles were reflected to expose the dorsal surface of the spinal column. The two vertebral arteries were exposed where they pass through the first cervical vertebra. Both arteries were permanently occluded by the application of electrocautery. After coagulation of the vertebral arteries, the rat was removed from the stereotaxic instrument and the surgical wound was sutured. Two longitudinal incisions were then made on the ventral surface of the neck. The two common carotid arteries were exposed and dissected free from surrounding nerves and connective tissue. An atraumatic clasp, fabricated mainly from silicone rubber tubing, was placed around each carotid artery in a manner such that the vessel was not traumatized or occluded. An indwelling jugular cannula was implanted into each rat for drug delivery. The surgical wounds were then closed. The atraumatic clasps were designed in such a manner that they could be tightened to occlude the carotid arteries by pulling on a small silastic thread that was allowed to protrude from the wound. Circulation to the brain through the carotids could be restored by relieving the tension on the silastic threads. After the surgery, the rats were allowed to recover for 24 hours.

Cerebral ischeira seas induced by tightening the clasps around the carotids. During this time, rats in which ischemia had successfully been produced lost the righting reflex and became unresponsive to stimuli. The period of ischemia was 20 minutes, and immediately after the 20 minutes of ischemia, at the time of reperfusion, compounds were administered as an intravenous bolus injection of 10 mg/kg followed by a constant intravenous infusion of 5.0 mg/kg per hour for 20 hours. Five days after the ischemia, the rats were sacrificed, and the brains were perfused, fixed with formalin and processed for histological evaluation.

One of the areas of the brain that is most susceptible to ischemia induced damage both in the rat and the human is the $CA_1$ pyramidal cell layer of the hippocampus. In animals that remain unresponsive for the 20 minute period of ischemia, the $CA_1$ pyramidal cell layer is completely destroyed. This layer of cells was examined microscopically in histological sections prepared from the hippocampus. Brain damage was rated according to the following scale:

0=no damage, completely intact cell layer

1=mild damage, one-third of $CA_1$ layer dead

2=moderate damage, two-thirds of $CA_1$ layer dead

3=severe damage, greater than 90% cell death

Damage in 4 sections of the dorsal hippocampus from each brain was assessed in order to obtain an accurate estimate of damage. An average damage score was calculated for each treatment croup. Scores from treated groups were compared statistically with scores from control groups which received only the vehicle (phosphate buffered saline) that was used to suspend the compounds. The level of significance was determined using the Mann Whitney-U-test.

Compounds of the instant invention were tested in the above-described assay and were found to be useful.

The following three tests are useful in predicting the ability of a compound to inhibit free radical formation which is believed to be implicated in disease such as ischemia, Parkinson's disease, Alzheimer's disease, Down's syndrome and ALS.

Lipid Peroxidation Test

Compounds of formula I were shown to inhibit the formation of lipid peroxides in mammals using the test protocol described by Aruoma, et al., (1990), Free Rad. Res. Comm., 10:143, herein incorporated by reference. Compounds of the instant invention tested in the assay cited above were found to be active.

Superoxide $O_2$. Secretion Test

The compounds of formula I, in addition, were tested for their ability to inhibit superoxide $O_2$. secretion using the method of Lorico, et al., (1986), Biochem. Pharmacol., 35:2443, herein incorporated by reference. Compounds of the instant invention tested in the above mentioned assay were found to be useful.

$H_2O_2$ Secretion Test

Finally, using the protocol of Root, et al., (1975), J. Clin. Invet., 55:945, herein incorporated by reference, compounds of formula I were tested and found to be effective in inhibiting $H_2O_2$ secretion.

Pharmaceutical Formulations

As noted above, the compounds of formula I are capable of slowing the process of neurodegeneration associate with Parkinson's disease, Alzheimer's disease, Down's syndrome, amyotrophic lateral sclerosis and preventing ischemia induced cell damage thereby lending themselves to the valuable therapeutic methods claimed herein. This method comprises administering to a mammal in need of treatment for Parkinson's disease, Alzheimer's disease, amyotrophic lateral sclerosis or ischemia an amount of one or more compounds of formula I effective in achieving the therapeutic effect desired.

In general, the compounds of the invention are most desirably administered at a concentration that will generally afford effective results without causing any harmful or deleterious side effects and can be administered either as a single unit dose, or if desired, the dosage may be divided into convenient subunits administered at suitable times throughout the day.

The compounds utilized in the method of the present invention are effective over a wide dosage range for the treatment of Parkinson's disease, Alzheimer's disease, ALS and ischemia induced cell damage. Thus, as used herein, the term "therapeutically effective amount" refers to a dosage range of from about 0.5 to about 150 mg/kg of body weight per day. In the treatment of adult humans, the range of about 1.0 to about 50 mg/kg per day, is preferred. The compound is preferably administered as an intravenous bolus of from about 0.1 to 100 mg/kg of body weight followed by a constant intravenous infusion of about 0.1 to 50 mg/kg per hour for a period of about 24 hours. However, it will be understood that the amount of the compound actually administered will be determined by a physician, in the light of the relevant circumstances including the choice of compound to be administered, the chosen route of administration, the age, weight, and response of the individual patient, and the severity of the patient's symptoms, and therefore the above dosage ranges are not intended to limit the scope of the invention in any way.

The compositions are formulated preferably in intravenous form such that each dosage contains from about 4.5 to about 9.5 g of the active ingredient in association with one or more suitable pharmaceutical diluents or excipients.

The neurodegenerative diseases, Parkinson's disease, Alzheimer's disease, amyotrophic lateral sclerosis and Down's syndrome are chronic conditions. The term "chronic" means a deteriorating condition of slow progress and long continuance. As such, a chronic neurodegenerating condition is treated when it is diagnosed and continued throughout the course of the disease.

Ischemia represents a phenomenon in which tissue is deprived of either partial or total blood flow in conjunction with hypoxia. It may occur as an acute event or a chronic condition. The term "acute" means an exacerbated condition of short course followed by a period of remission. Thus, the treatment of ischemia induced cell damage contemplates both acute and chronic forms. In an acute event, compound is administered at the onset of symptoms and discontinued when the symptoms disappear. As described above, a chronic condition is treated throughout the course of the disease.

The compounds can be administered by a variety of routes including the oral, rectal, transdermal, subcutaneous, intravenous, intramuscular or intranasal routes. The intravenous route of administration is preferred. No matter what route of administration is chosen, such administration is accomplished by means of pharmaceutical compositions which are prepared by techniques well known in the pharmaceutical sciences.

In making the pharmaceutical compositions, one or more active ingredients will usually be mixed with a carrier, or diluted by a carrier, or enclosed within a carrier, or diluted by a carrier, or enclosed within a carrier which may be in the form of a capsule, sachet, paper or other container. When the carrier serves as a diluent, it may be a solid, semi-solid or liquid material lathich acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide rapid, sustained or delayed release of the active ingredient after administration to the patient by employing procedures well known in the art.

The following formulation examples may employ as active ingredients any of the compounds of formula III. The examples are illustrative only and are not intended to limit the scope of the invention in any way.

Formulation 1

Hard gelatin capsules are prepared using the following ingredients:

| | Quantity (mg/capsule) |
|---|---|
| 2-(3,5-di-t-butyl-4-hydroxyphenyl)-4-(2-(4-ethylaminomethyl-phenoxy) ethyl)thiazole | 500 |
| Starch dried | 200 |
| Magnesium | 10 |

The above ingredients are mixed and filled into hard gelatin capsules in 710 mg quantities.

Formulation 2

A tablet formula is prepared using the ingredients below:

| | Quantity (mg/tablet) |
|---|---|
| 2-(3,5-di-t-butyl-4-hydroxyphenyl)-4-(2-(4-dimethylaminomethyl-phenylthio)ethyl)oxazole | 100 |
| Cellulose, microcrystalline | 400 |
| Silicon dioxide, fumed | 10 |
| Stearic acid | 5 |

The components are blended and compressed to form tablets each weighing 515 mg.

Formulation 3

Tablets each containing 50 mg of active ingredient are made up as follows:

| | Quantity (mg/tablet) |
|---|---|
| 2-(3,5-di-t-butyl-4-hydroxyphenyl)-4-(2-(4-methylethylaminomethyl-phenylthio)propyl)-5-ethyl-thiazole | 50 mg |
| Starch | 50 mg |
| Microcrystalline cellulose | 40 mg |
| Polyvinylpyrrol idone (as 10% solution in water | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate and talc, previously passed through a No. 60 mesh U.S. Sieve, are then added to the granules which, after mixing, are compressed by a tablet machine to yield tablets each weighing 150 mg.

Formulation 4

Capsules each containing 25 mg of medicament are made as follows:

| | Quantity (mg/capsule) |
|---|---|
| 2-(3 5-diethyl-4-hydroxyphenyl)-4-(2-(3-dimethylaminomethyl-phenoxy)butyl)oxazole | 25 mg |
| Starch | 60 mg |
| Microcrystalline cellulose | 60 mg |
| Magnesium stearate | 5 mg |
| Total | 150 mg |

The active ingredient, cellulose, starch and magnesium stearate are blended, passed through a No. 45 mesh U.S. sieve, and filled into hard gelatin capsules in 200 mg quantities.

Formulation 5

Suppositories each containing 250 mg of active ingredient are made up as follows:

| | Quantity (mg/suppository) |
|---|---|
| 2-(3,5-di-t-butyl-4-methoxyphenyl)-4-(2-(4-n-propylaminomethyl-phenoxy)ethyl)oxazole | 250 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions each containing 100 mg of medicament per 5 ml dose are made as follows:

| | Quantity (mg/5 ml) |
|---|---|
| 2-(3, 5-di-t-butyl-4-hydroxyphenyl)-4-(2-(4-n-hexylaminomethyl-phenylthio)methyl)oxazole | 100 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 7

Capsules each containing 5 mg of medicament are made up as follows:

| | Quantity (mg/tablet) |
|---|---|
| 2-(3-isopropyl-5-t-butyl-4-hydroxyphenyl)-4-(2-(4-diethylaminomethyl-phenoxy)ethyl)oxazole | 5 mg |
| Starch | 164 mg |
| Microcrystalline cellulose | 164 mg |
| Magnesium stearate | 22 mg |
| Total | 355 mg |

The active ingredient, cellulose, starch and magnesium stearate are blended, passed through a No. 45 mesh U.S. sieve, and filled into hard gelatin capsules in 355 mg quantities.

Formulation 8

An intravenous formulation may be prepared as follows:

| | Quantity (g) |
|---|---|
| 2-(3,5-di-t-butyl-4-hydroxyphenyl)-4-(2-(4-n-butylmethylaminomethyl-phenoxy)ethyl)oxazole | 5 g |
| Isotonic Saline | 1 g |
| Total | 6 g |

The solution of the above ingredients is administered intravenously at a rate of 1 ml per minute to a subject in need of treatment.

We claim:

1. A method for treating a disease selected from the group consisting of Alzheimer's disease, Parkinson's disease, amytrophic lateral sclerosis or cerebral trauma in a mammal in need of such treatment which comprises administering to said mammal a therapeutically effective amount of a compound of formula (III)

(III)

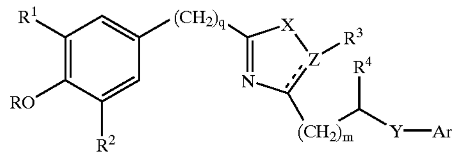

wherein:

Ar is phenyl, pyridyl, tetrahydronaphthyl, benzofuranyl or chromanyl substituted with zero to two substituents selected from the group consisting of —$(C_1–C_6)$alkyl, hydroxy and halo;

and substituted with one or two substituents selected from the group consisting of —$O(CH_2)_rR^6$,

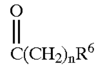

and —$(C_1–C_6$ alkyl$)R^6$;

provided that the phenyl or pyridyl group of Ar may additionally be substituted with two substituents which when taken together with the carbon atoms to which they are attached form a phenyl ring;

where $R^6$ is —$NR^7R^8$, morpholin-1-yl, imidazol-1-yl, 4,5-dihydro-1H-imidazol-2-yl, thiomorpholin-1-yl, piperazin-1-yl or piperazin-1-yl substituted with —$(C_1–C_4)$alkyl or

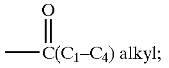

and $R^7$ and $R^8$ are each individually hydrogen, —$(C_1–C_6)$alkyl, —$(CH_2)_p$OH,

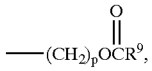

—$(CH_2)_p$-piperidyl, —$(CH_2)_pS(C_1–C_6)$alkyl, —$(CH_2)_pO(C_1–C_6)$alkyl,

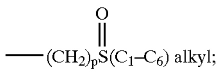

where $R^9$ is $(C_1–C_6)$alkyl;

-----

≠ represents a double or single bond;

X is —O— or —S—;

Y is —$CR^{5'}R^5$—, —O— or —S—, where $R^{5'}$ is H and $R^5$ is —H or —OH or R5 and $R^{5'}$ taken together are =O;

R is H or —$(C_1–C_6)$alkyl;

$R^1$ and $R^2$ are each individually —$(C_1–C_6)$alkyl, —$(C_1–C_6)$alkoxy or phenyl;

$R^3$ is H or —$(C_1–C_6)$alkyl;

$R^4$ is hydrogen or —OH, or when Y is —$CHR^5$, $R^4$ and $R^5$ are each individually H or when taken together form a bond;

m is an integer from 0 to 2, both inclusive;

q is 0 or 1;

n is an integer from 0 to 4 both inclusive;

p is an integer from 1 to 6 both inclusive; and t is an integer from 1 to 4 both inclusive;

or a pharmaceutically acceptable salt, hydrate or optical isomer thereof.

2. A method for treating a disease selected from the group consisting of Alzheimer's disease, Parkinson's disease, amytrophic lateral sclerosis or cerebral trauma in a mammal in need of such treatment which comprises administering to said mammal a therapeutically effective amount of a compound of formula (II)

(II)

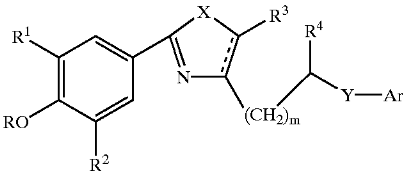

wherein:

Ar is phenyl, pyridyl, or tetrahydronaphthyl substituted with zero to two substituents selected from the group consisting of —$(C_1$–$C_6)$alkyl, hydroxy and halo; and substituted with one or two substituents selected from the group consisting of —$O(CH_2)_tR^6$,

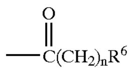

and —$(C_1$–$C_6$ alkyl)$R^6$;

provided that the phenyl or pyridyl group of Ar may additionally be substituted with two substituents which when taken together with the carbon atoms to which they are attached form a phenyl ring;

where $R^6$ is —$NR^7R^8$, morpholin-1-yl, imidazol-1-yl, 4,5-dihydro-1H-imidazol-2-yl, thiomorpholin-1-yl, piperazin-1-yl or piperazin-1-yl substituted with —$(C_1$–$C_4)$alkyl or

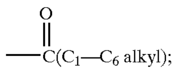

and $R^7$ and $R^8$ are each individually hydrogen, —$(C_1$–$C_6)$alkyl, —$(CH_2)_pOH$, —$(CH_2)_p$-piperidyl, —$(CH_2)_pS(C_1$–$C_6)$alkyl or

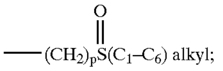

≠ represents a double or single bond;

X is —O— or —S—;

Y is —$CHR^5$—, —O— or —S—;

R is H or —$(C_1$–$C_6)$alkyl;

$R^1$ and $R^2$ are each individually —$(C_1$–$C_6)$alkyl or —$(C_1$–$C_6)$ alkoxy;

$R^3$ is H or —$(C_1$–$C_6)$alkyl;

$R^4$ is hydrogen, or when Y is —$CHR^5$, $R^4$ and $R^5$ are each individually H or when taken together form a bond;

m is an integer from 0 to 2, both inclusive;

q is 0 or 1;

n is an integer from 0 to 4 both inclusive;

p is an integer from 1 to 6 both inclusive; and t is an integer from 1 to 4 both inclusive;

or a pharmaceutically acceptable salt, hydrate or optical isomer thereof.

3. A method for treating a disease selected from the group consisting of Alzheimer's disease, Parkinson's disease, amytrophic lateral sclerosis and cerebral trauma in a mammal in need of such treatment which comprises administering to said mammal a therapeutically effective amount of a compound of formula (I)

(I)

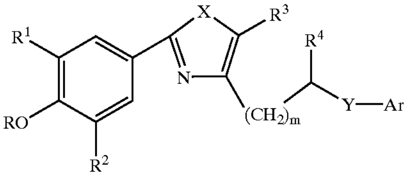

wherein

Ar is phenyl or pyridyl substituted with zero to two substituents selected from the group consisting of —$(C_1$–$C_6)$ alkyl, hydroxy and halo;

and substituted with one or two substituents selected from the group consisting of

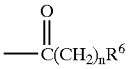

and —$(C_1$–$C_6)$ alkyl $R^6$;

provided that the phenyl or pyridyl group of Ar may additionally be substituted with two substituents which when taken together with the carbon atoms to which they are attached form a phenyl ring;

where $R^6$ is —$NR^7R^8$, morpholin-1-yl, imidazol-1-yl, 4,5-dihydro-1H-imidazol-2-yl, thiomorpholin-1-yl, piperazin-1-yl or piperazin-1-yl substituted with

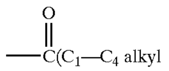

10 or —$(C_1$–$C_6)$alkyl; and $R^7$ and $R^8$ are each individually hydrogen, —$C_1$–$C_6$ alkyl, —$(CH_2)$pOH or —$(CH_2)$p-piperidyl;

X is —O— or —S—;

Y is —$CHR^5$—, —O— or —S—;

R is —H or $(C_1$–$C_6)$alkyl;

$R^1$ and $R^2$ are each individually —$(C_1$–$C_6)$alkyl;

$R^3$ is H or —$(C_1$–$C_6)$alkyl;

$R^4$ is hydrogen, or when Y is —$CHR^5$, $R^4$ and $R^5$ are each individually H or when taken together form a bond;

m is 0 or 1;

n is an integer from 0 to 4 both inclusive; and p is an integer from 1 to 6 both inclusive;

or a pharmaceutically acceptable salt, hydrate or optical isomer thereof.

4. A method for treating a disease selected from the group consisting of Alzheimer's disease, Parkinson's disease, amytrophic lateral sclerosis and cerebral trauma in a mammal in need of such treatment which comprises administering to said mammal a therapeutically effective amount of 2-(3,5-di-t-butyl-4-hydroxyphenyl)-4-(2-(4-methylethylaminomethylphenyloxy)ethyl)oxazole; 2-(3,5-di-tert-butyl-4-hydroxyphenyl))-4-((4-N-methyl-N-ethylaminomethyl)phenoxymethyl)oxazolehydrochloride; 2-(3,5-di-t-butyl-4-hydroxyphenyl)-4-((4-N-ethyl-N-propylaminoethylphenoxy)methyl)oxazole hydrochloride or 2-(3,5-di-t-butyl-4-hydroxyphenyl)-4-(2-(4-ethylpropylaminoethylphenoxy)ethyl)oxazole.

* * * * *

UNITED STATES PATENT AND TRADEMARK OFFICE

CERTIFICATE OF CORRECTION

PATENT NO. : 6,423,709 B1
DATED : July 23, 2002
INVENTOR(S) : Panetta et al.

It is certified that error appears in the above-identified patent and that said Letters Patent is hereby corrected as shown below:

Column 104,
Line 56, "# represents a double..." should read -- = represents a double... --

Column 105,
Line 61, "# represents a double..." should read -- = represents a double... --

Signed and Sealed this

Eighth Day of July, 2003

JAMES E. ROGAN
*Director of the United States Patent and Trademark Office*